(12) United States Patent
Hunter et al.

(10) Patent No.: US 11,497,964 B1
(45) Date of Patent: Nov. 15, 2022

(54) DEVICES, SYSTEMS AND METHODS FOR USING AND MONITORING SPORTS EQUIPMENT AND SPORTS ACTIVITIES

(71) Applicant: Canary Medical Switzerland AG, Baar (CH)

(72) Inventors: William L. Hunter, Vancouver (CA); Olivia F. Hunter, Vancouver (CA); Douglas R. Holberg, Wimberley, TX (US)

(73) Assignee: Canary Medical Switzerland AG, Baar (CH)

( * ) Notice: Subject to any disclaimer, the term of this patent is extended or adjusted under 35 U.S.C. 154(b) by 0 days.

(21) Appl. No.: 15/268,575

(22) Filed: Sep. 17, 2016

Related U.S. Application Data

(60) Provisional application No. 62/220,239, filed on Sep. 17, 2015.

(51) Int. Cl.
*A63B 24/00* (2006.01)
*A63B 71/00* (2006.01)

(52) U.S. Cl.
CPC ...... *A63B 24/0062* (2013.01); *A63B 71/0054* (2013.01)

(58) Field of Classification Search
CPC .................................................. A63B 24/0062
See application file for complete search history.

(56) References Cited

U.S. PATENT DOCUMENTS

| | | | |
|---|---|---|---|
| 5,672,954 A | 9/1997 | Watanabe | |
| 7,127,300 B2 | 10/2006 | Mazar et al. | |
| 8,289,185 B2 | 10/2012 | Alonso | |
| 8,477,046 B2 | 7/2013 | Alonso | |
| 9,227,128 B1* | 1/2016 | Carfagna, Jr. | ..... A63B 24/0087 |
| 9,698,841 B2* | 7/2017 | Alonso | ................. G06Q 50/20 |
| 10,499,855 B2 | 12/2019 | Hunter | |
| 2002/0060633 A1* | 5/2002 | Crisco, III | ........... A61B 5/4076 340/669 |
| 2005/0165317 A1 | 7/2005 | Turner et al. | |
| 2005/0242666 A1 | 11/2005 | Huscher et al. | |
| 2007/0234819 A1 | 10/2007 | Amirouche | |
| 2008/0018532 A1 | 1/2008 | Mackintosh et al. | |
| 2008/0065225 A1 | 3/2008 | Wasielewski | |
| 2008/0215609 A1 | 9/2008 | Cleveland et al. | |
| 2008/0284650 A1 | 11/2008 | Macintosh et al. | |
| 2008/0300659 A1 | 12/2008 | Matos | |
| 2009/0048039 A1 | 2/2009 | Holthouse et al. | |
| 2009/0048044 A1* | 2/2009 | Oleson | ............... A63B 24/0062 473/570 |
| 2009/0048070 A1* | 2/2009 | Vincent | .............. A63B 24/0021 482/8 |
| 2011/0063094 A1 | 3/2011 | Meiertoberens et al. | |
| 2012/0198593 A1* | 8/2012 | Beck | .......................... F41J 5/04 2/2.5 |
| 2013/0252610 A1 | 9/2013 | Kim | |
| 2013/0274587 A1* | 10/2013 | Coza | .................... A61B 5/6804 600/409 |
| 2014/0031063 A1 | 1/2014 | Park et al. | |

(Continued)

FOREIGN PATENT DOCUMENTS

WO 2015157808 10/2015

*Primary Examiner* — Dmitry Suhol
*Assistant Examiner* — Jeffrey K Wong

(57) ABSTRACT

Sports equipment and/or areas of play are provided, comprising a sports equipment or area of play and a sensor.

11 Claims, 50 Drawing Sheets

Football Equipment & Uniform Sensors

⬤ Position/Location/GPS/Pressure Sensor & Accelerometers & Physiology

(56) References Cited

U.S. PATENT DOCUMENTS

| | | |
|---|---|---|
| 2014/0067098 A1 | 3/2014 | Regan |
| 2014/0085102 A1 | 3/2014 | McCormick |
| 2014/0244007 A1* | 8/2014 | Kampman .......... G06F 19/3481 |
| | | 700/91 |
| 2014/0256324 A1 | 9/2014 | Mohanty |
| 2014/0328253 A1 | 11/2014 | Lee |
| 2014/0371885 A1* | 12/2014 | Ianni .................. G06K 9/00342 |
| | | 700/91 |
| 2015/0040685 A1* | 2/2015 | Nicholson ............ A61B 5/4064 |
| | | 73/862.51 |
| 2015/0057775 A1* | 2/2015 | Dong .................... A61B 5/1113 |
| | | 700/91 |
| 2015/0062440 A1* | 3/2015 | Baxter ............... G06K 9/00342 |
| | | 348/734 |
| 2015/0097700 A1 | 4/2015 | Holthouse |
| 2015/0157900 A1 | 6/2015 | Holthouse |
| 2015/0356332 A1 | 12/2015 | Turner et al. |
| 2015/0375083 A1 | 12/2015 | Stelfox et al. |
| 2015/0382076 A1* | 12/2015 | Davisson ............. H04N 21/435 |
| | | 725/62 |
| 2016/0171864 A1* | 6/2016 | Ciaramelletti ....... A61B 5/6801 |
| | | 340/539.11 |
| 2016/0204958 A1 | 7/2016 | Muetzel et al. |
| 2016/0306038 A1* | 10/2016 | Zoeke ................... G01S 13/876 |
| 2016/0328637 A1* | 11/2016 | Viikari ............... G06K 19/0717 |
| 2016/0340177 A1 | 11/2016 | Takada |
| 2017/0032693 A1 | 2/2017 | Regan et al. |
| 2017/0138986 A1 | 5/2017 | Kern |

* cited by examiner

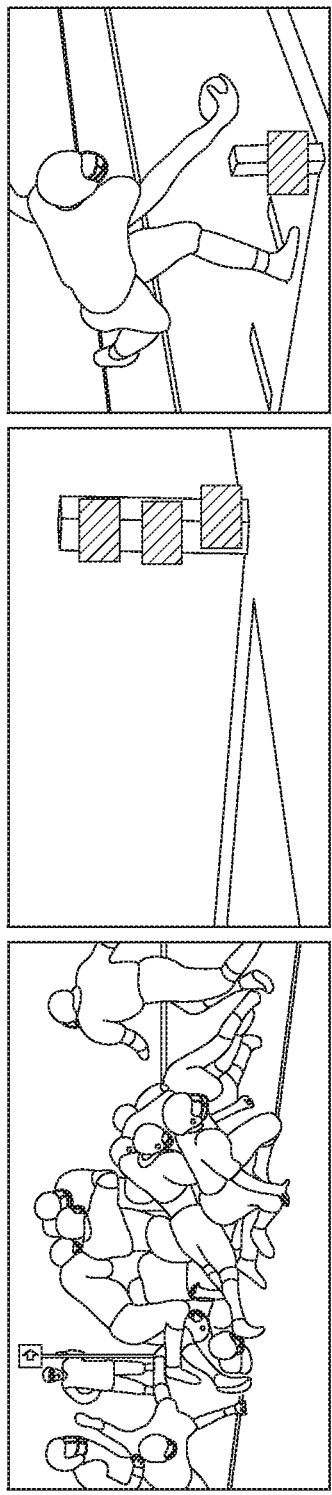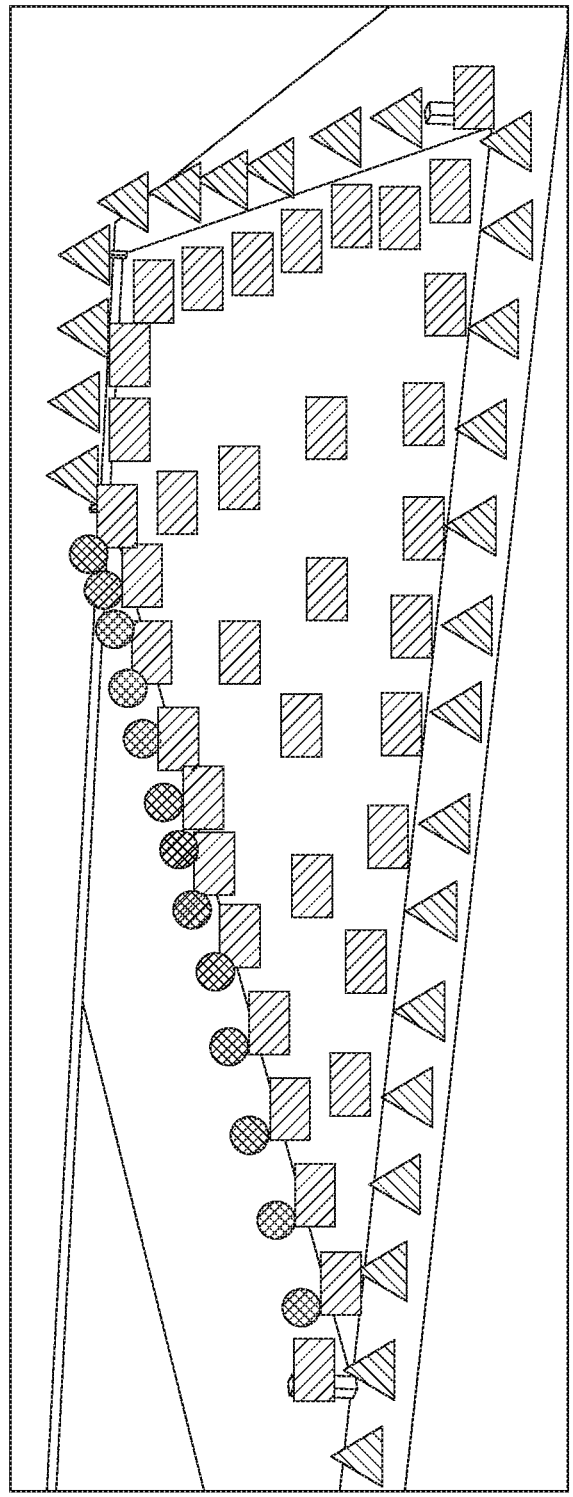
FIG. 10

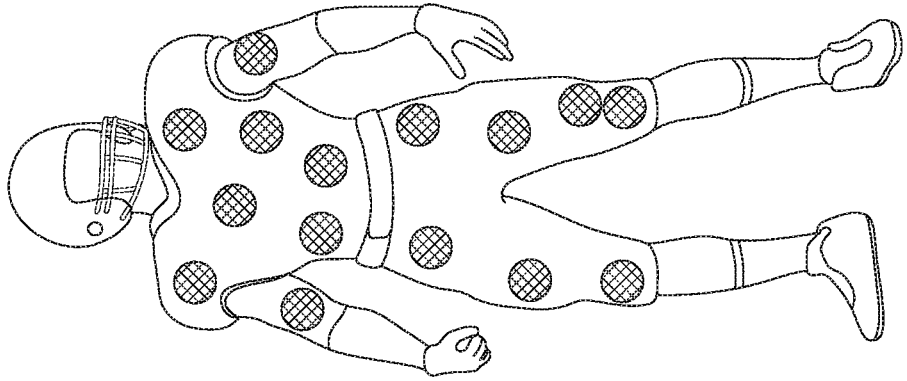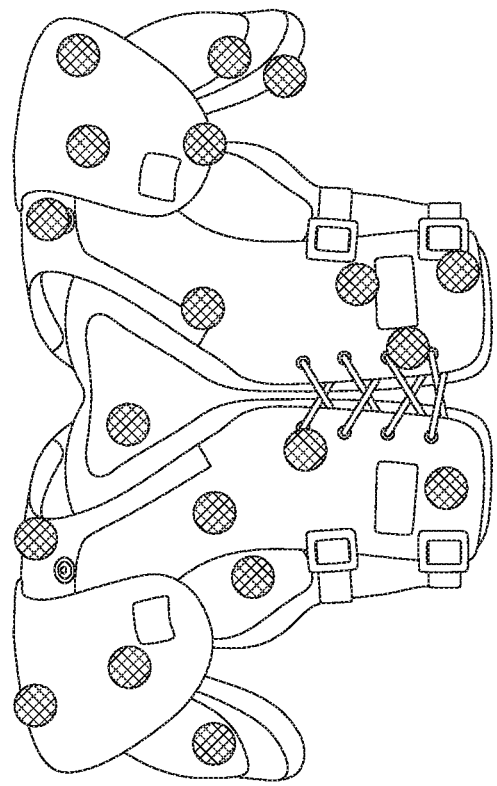
FIG. 12
Football Equipment & Uniform Sensors
● Position/Location/GPS/Pressure Sensor & Accelerometers & Physiology

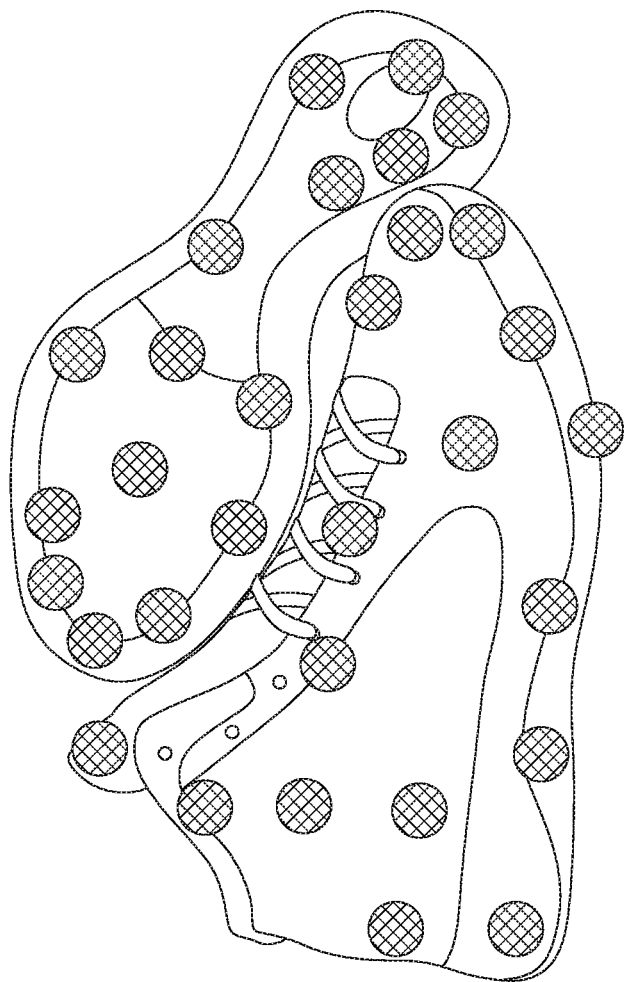
Basketball Uniform and Shoes
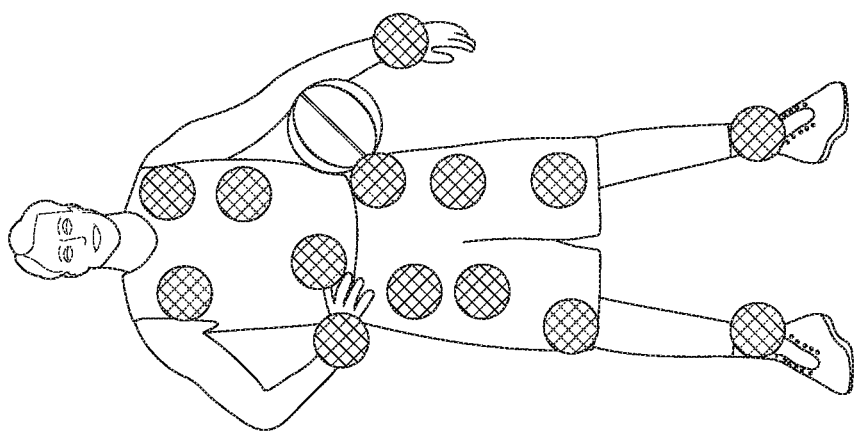
Position/Location/GPS/Pressure Sensor/Accelerometers & Physiology
FIG. 22

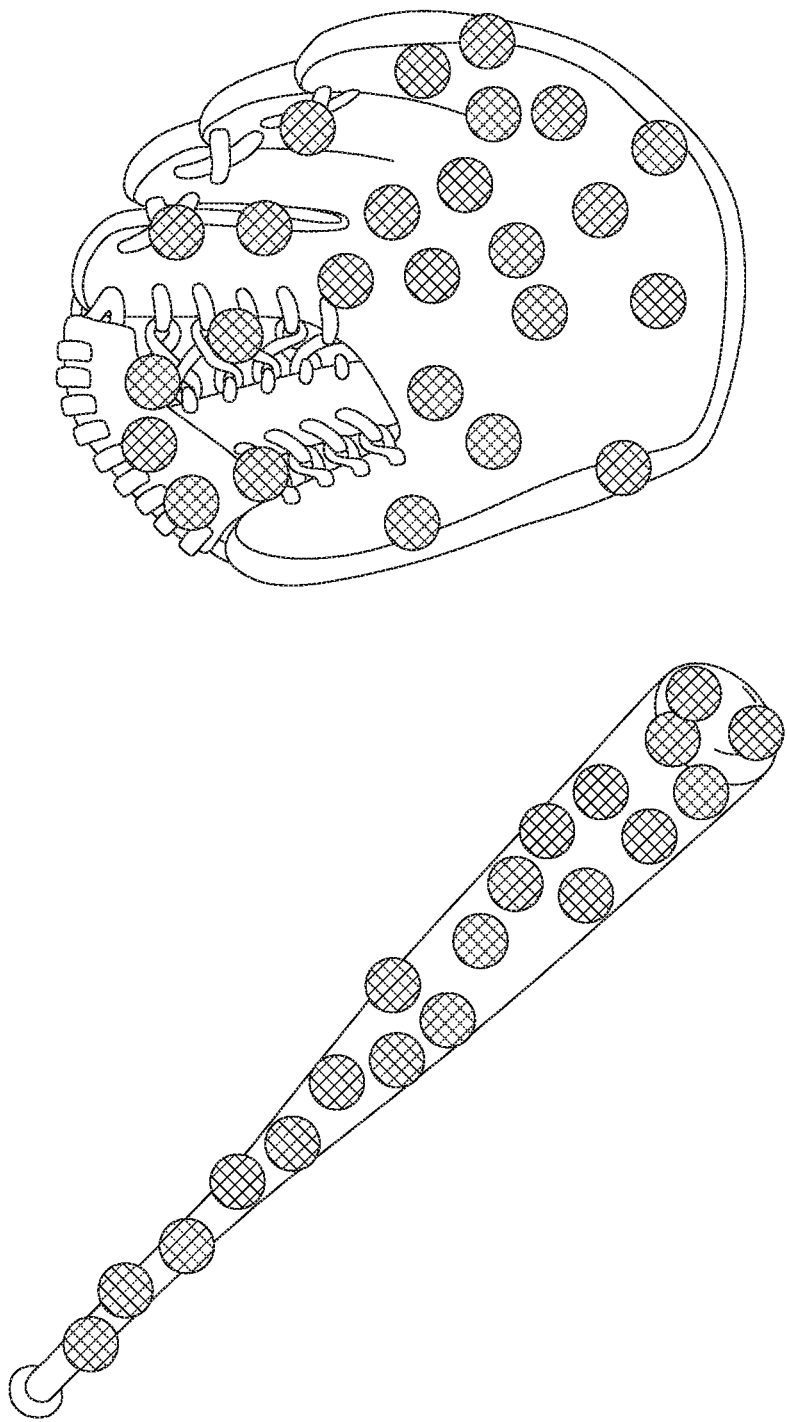
Baseball Bats and Gloves
 Position/Location/GPS/Pressure Sensor/Accelerometers
FIG. 27

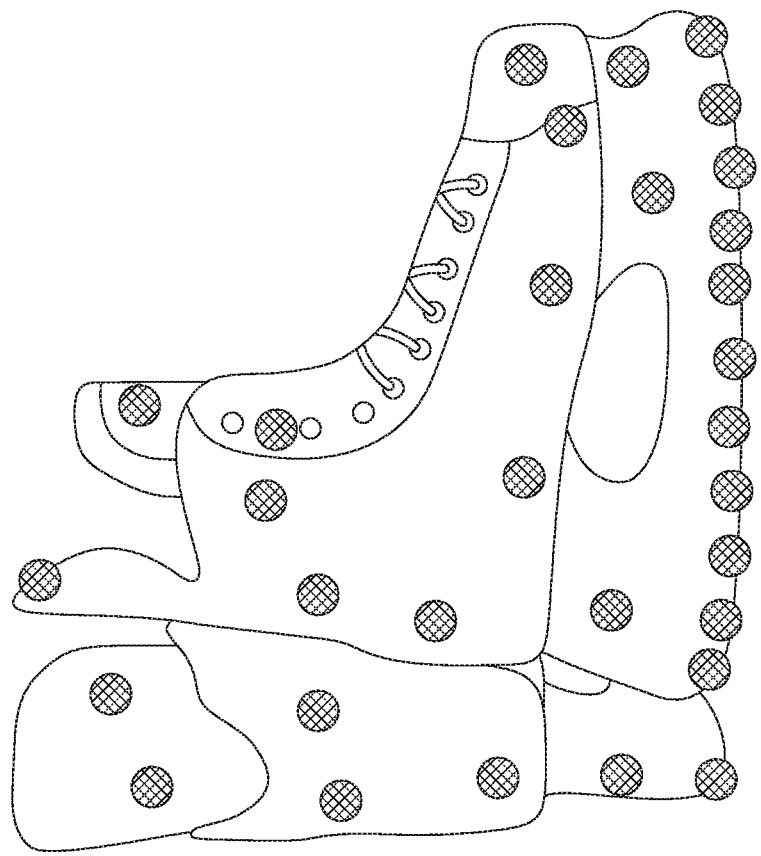
Hockey Skate Sensors
 Position/Location/GPS/Pressure Sensor/Accelerometers
FIG. 33

Hockey Helmets
Head Injuries and Concussions (Acute & Cumulative)
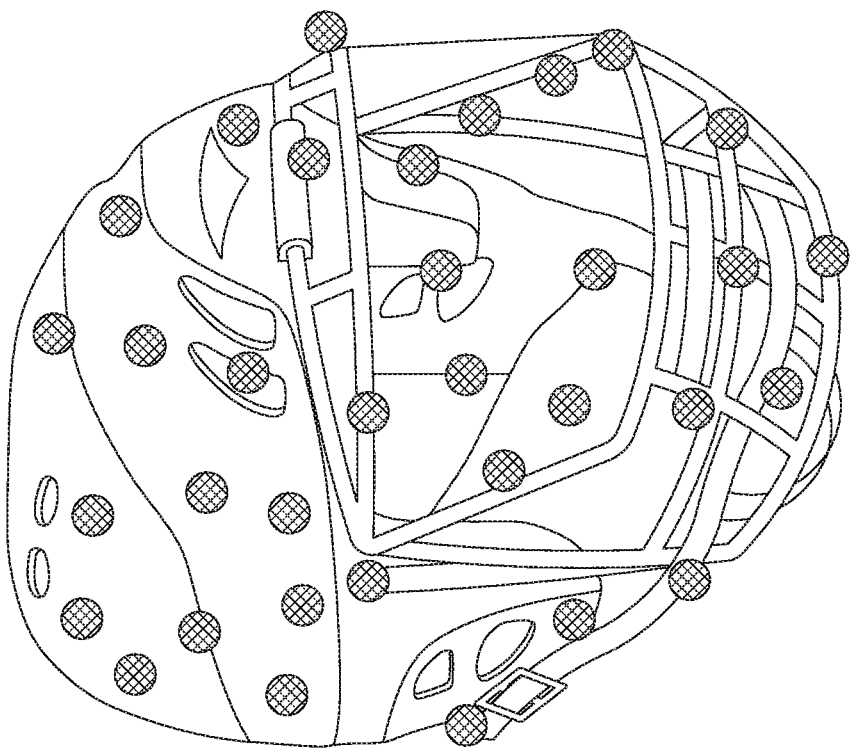
 Position/Location/GPS/Pressure Sensor/Accelerometers
FIG. 34

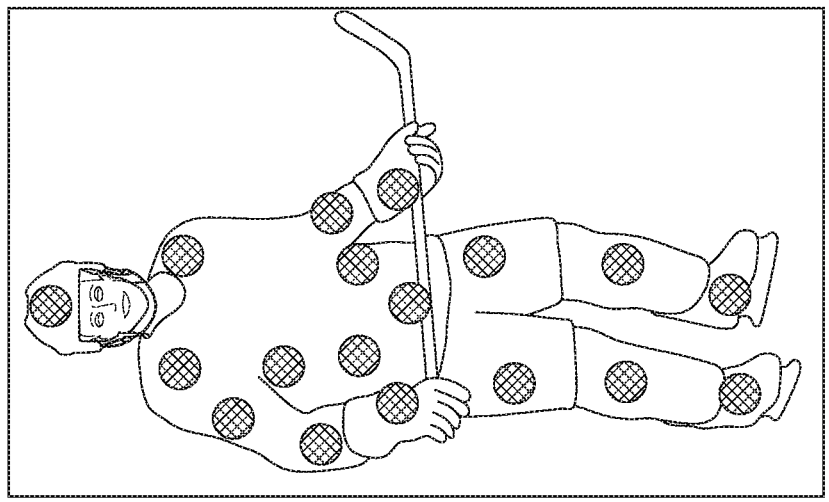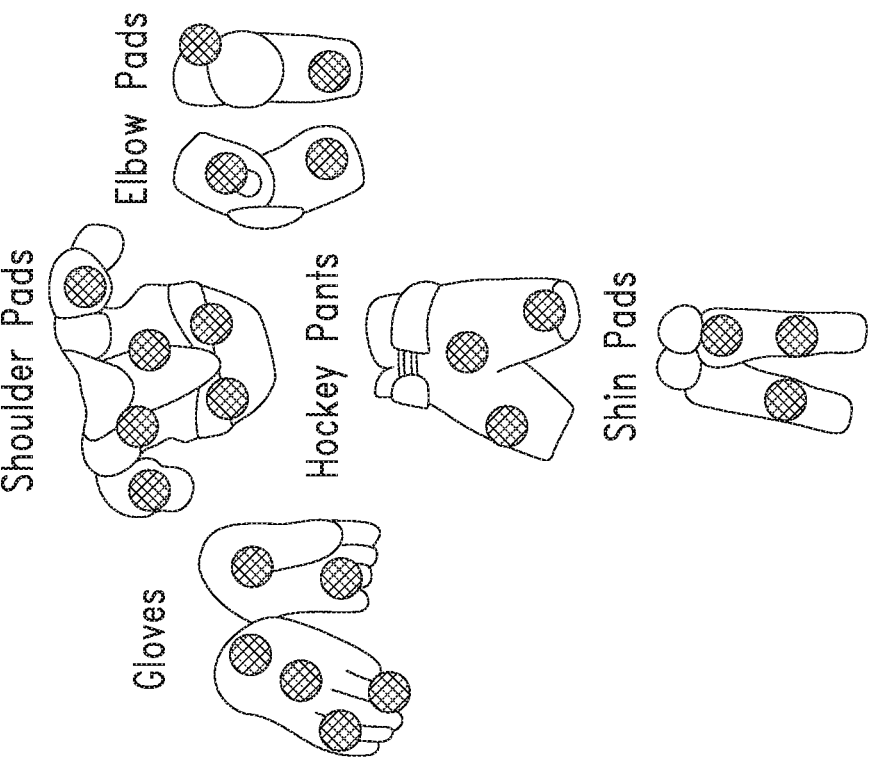
FIG. 35

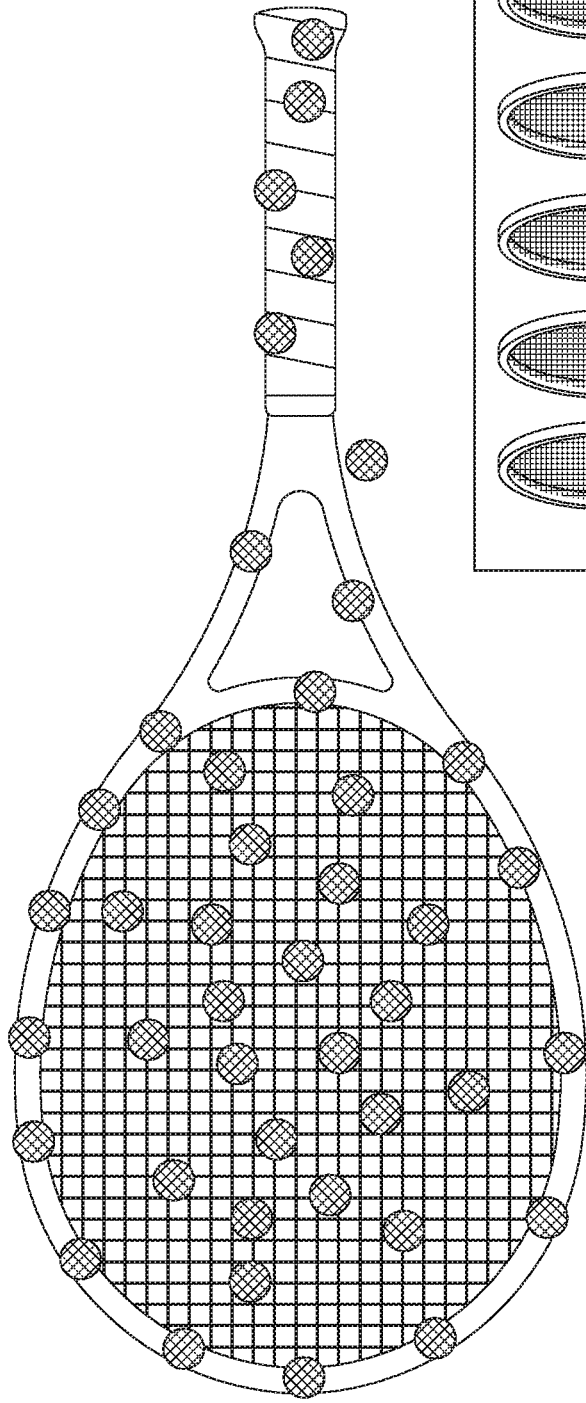
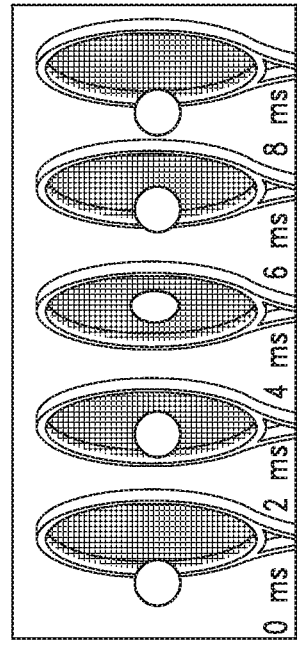
Tennis Rackets
● Position/Location/GPS/Pressure Sensor/Accelerometers
FIG. 38

Tennis Nets
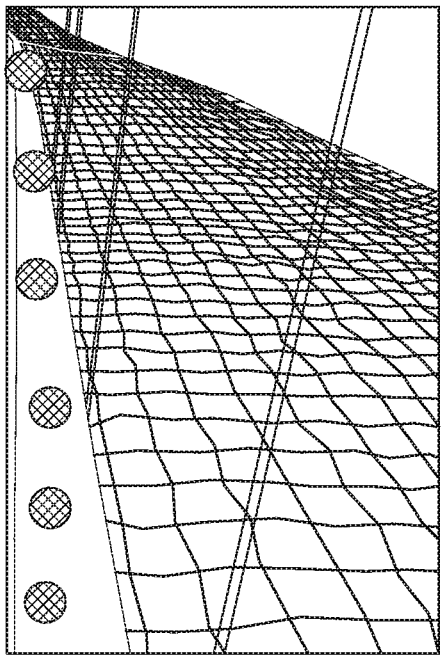
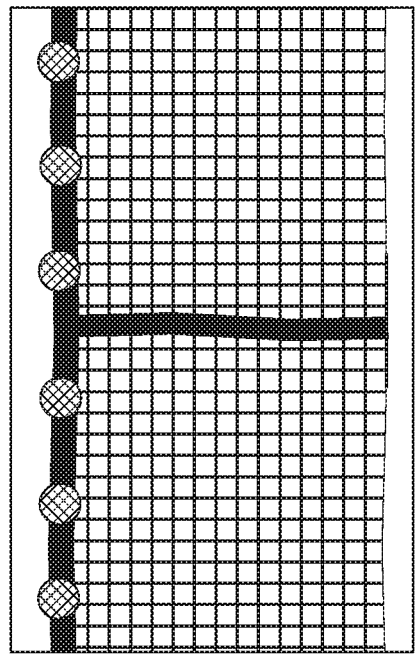
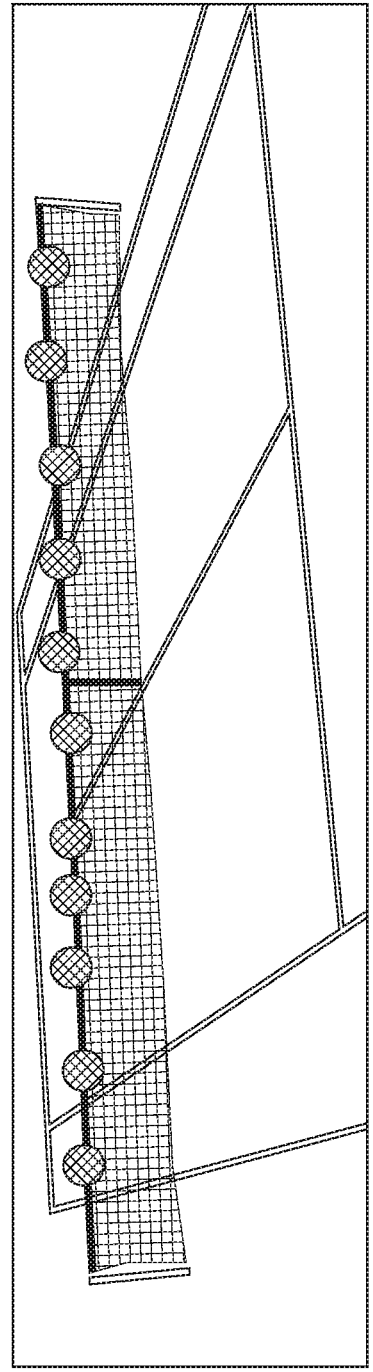
● Position/Location/GPS/Pressure Sensor/Accelerometers
FIG. 39

Golf Clothing, Gloves and Shoes
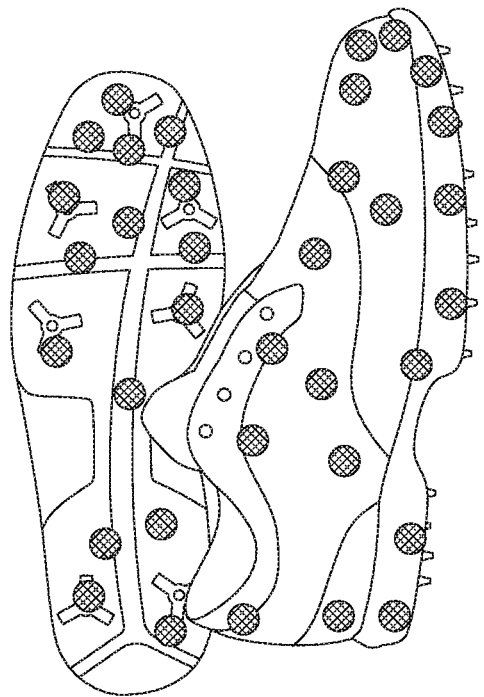
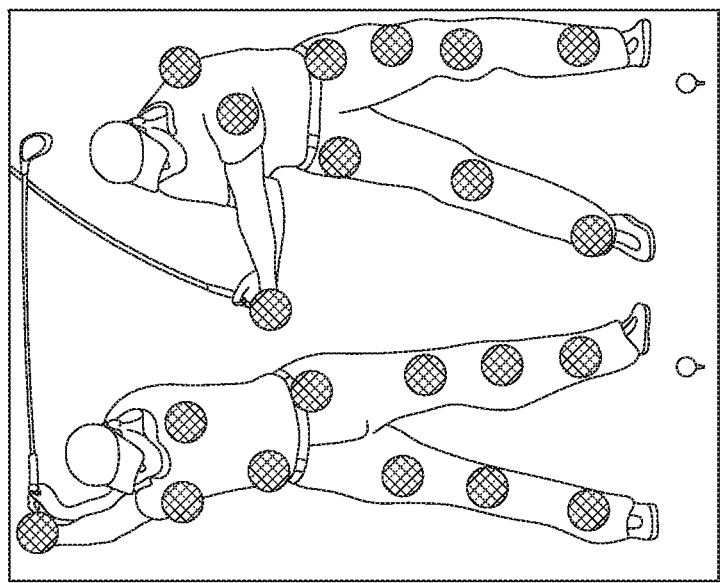
● Position/Location/GPS/Pressure Sensor/Accelerometers & Physiology
FIG. 44

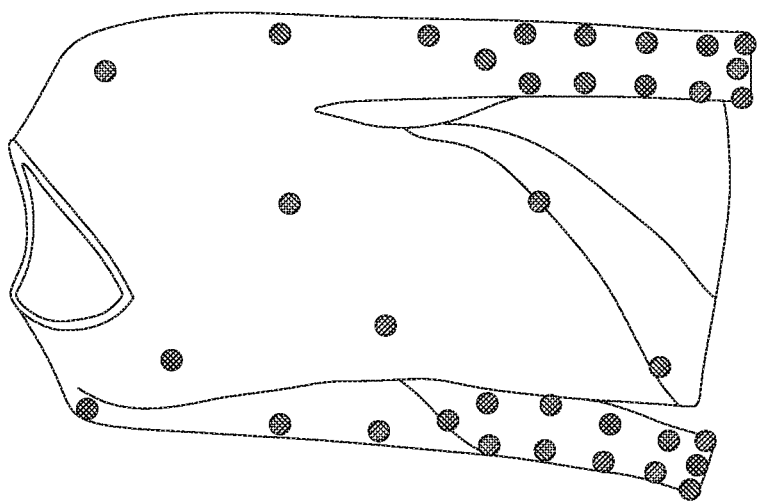
 Position/Location/GPS/Pressure Sensor/Accelerometers & Physiology
FIG. 49

DEVICES, SYSTEMS AND METHODS FOR USING AND MONITORING SPORTS EQUIPMENT AND SPORTS ACTIVITIES

CROSS-REFERENCE TO RELATED APPLICATION

This application claims the benefit under 35 U.S.C. § 119(e) of U.S. Provisional Patent Application No. 62/220,239, filed Sep. 17, 2015, which application is incorporated herein by reference in its entirety.

FIELD OF THE INVENTION

Technical Field

The present invention relates generally to sports, and more specifically, to devices and methods for monitoring and evaluating the performance of equipment and participants in a wide variety of sports

BACKGROUND

Description of the Related Art

Sport (or sports) refers to forms of competitive physical activity which are based upon physical athleticism, skill and/or dexterity, as well as intellectual ability and/or strategy. Sports most commonly are based upon rules of competition, with a common aim of sports is to improve or maintain physical ability, while at the same time providing recreation and enjoyment to participants and entertainment to spectators. Sports however, also rely on strategy, in order to be able to compete at the highest level.

Sports however can often push the limits of physical skills and abilities, and hence in some circumstances lead to significant trauma. For example, in the sport of football concussions and other play-related traumatic brain injuries have been proposed as a major cause of chronic traumatic encephalopathy (CTE) (see Schwarz, Alan (20 Dec. 2009) Retrieved 6 Jan. 2014; see also Associated Press (2007-09-29) "NFL Study Links Concussions, Depression", Washington Post, Retrieved 2013-09-03).

Sports are also often plagued with controversy involving interpretations of what happened during a game and interpretation of rules. For example, in the 1972 AFC wild card game between the Steelers and the Raiders, a pass was thrown with 22 seconds left in the game. Two players attempting to catch the pass collided and another player caught the ball before it hit the ground, ultimately running for a game-winning touchdown. Questions swirled around who had actually touched the ball, and whether the pass was illegal under the rules of the game at that time.

Hence, there is a need in the art for sports equipment that can help assess and prevent the likelihood of injury during the activity. In addition, there is a need in the art for sports equipment that can help assess compliance with the rules of the game. The present invention discloses sports equipment and areas of play containing a variety of sensors which can overcome many of the difficulties and limitations found with currently available sports equipment, and further provides other related advantages.

SUMMARY

Briefly stated, sports equipment (and related areas of play) are provided having one or more sensors (including for example 'sensor modules' or 'SMs' as described in more detail below). Such sensors can be placed on or within sports equipment and/or area of play in order to, amongst other things: a) monitor the safety and efficacy of the sports equipment and/or area of play; b) monitor wear and tear of the sports equipment and/or area of play; c) determine scoring; d) determine the applicability and/or enforcement of rules of the game; e) to monitor the safety of players, including over extended times beyond the time of the game; f) evaluate the performance, training and comparison of players; g) enhance the entertainment or viewing experience of spectators (e.g., by providing enhanced information such as the force of impacts, speeds and other physical measurements of the game, and by allowing comparisons with other known or estimated measurements from other games); h) for televised entertainment (e.g., by providing enhanced information as discussed herein); i) for providing actual measurements to be utilized for gaming purposes, and for determining statistical probabilities; j) in order to assist in the development of new and safer sports equipment and areas of play; k) to provide insight into new training methods, skills and/or techniques, and to assess the successfulness of such methods skills and/or techniques; and/or l) to be combined with other sensors on or in the equipment or area of play in order to provide a more complete picture or assessment of the game with respect to any of the above.

Within one aspect of the invention one or more sensors can be included into the area of play, including for example, boundaries associated with play, as well as markers which are associated with the play (e.g., yard lines in football or the three-point boundary in basketball). Hence, within one embodiment of the invention pressure sensors or location sensors can be placed onto the boundaries of an area of play and/or markers in the field of play (e.g., sensors on the boundaries of a football or soccer field, the bounds of baseball field, the floor of a basketball court, the ice of a hockey rink, the bounds of a tennis court, the edges of a golf course and the bounds of a volleyball court). One or more pressure or location sensors can also be placed within the bounds of play (e.g., yard markers on a football field; center markers on a soccer field;

The pitcher's mound, batter's box and catcher's box, infield lines and grass line, foul lines, baseline and running lanes, foul poles, warning track and outfield walls (including the top of the outfield walls) of a baseball field; on the center circle, three point line, free throw circle and free throw line of a basketball court; the end zone faceoff circle, center ice circle, and goal of an ice hockey rink; the baseline, singles and doubles sidelines, center service line and net of a tennis court; the traps and hazards of a golf course (e.g., sand and water traps); and the attack line which divides the front row from the back row in a volleyball court.

Within other aspects of the invention one or more sensors can be placed within in or on one or more objects that are associated with the area of play, including for example 'goal' objects which are associated with the game (e.g., a basketball hoop, the goalpost for American football, and the net for hockey). Hence, within certain embodiments of the invention pressure or location sensors can be placed on the goalposts and uprights of a football field post, and on the end zone pylons of a football field; on the goal posts and nets of a soccer field; on the bases/plates and foul poles of a baseball field; on the backboard, rim and nets of a basketball court; on the goal and nets of a hockey rink; the net of a tennis court; and the net of a volleyball court.

Within another aspect of the invention one or more sensors can be included into sports equipment, including for example, a) wearable garments associated with a sport (e.g., uniforms hats gloves and shoes); b) protective gear associated with a sport (e.g., helmets and pads); c) competitive objects of the game (e.g., balls, pucks and the like); and d) instruments and implements of the game (e.g., sticks, bats, and the like).

Hence, within one of the embodiments of the invention one or more pressure sensors, location sensors, GPS, accelerometers, gyroscopes, time measurement devices and temperature sensors can be included on wearable garments (i.e., articles of covering over a body). Examples of wearable garments include, for example, socks, cleats, football uniforms and gloves for football; on socks, cleats and soccer uniforms and headbands for soccer; on socks, tennis shoes and uniforms for basketball; on socks, cleats, baseball uniforms and gloves for baseball; on socks, skates, hockey uniforms and gloves for hockey; on socks, tennis shoes and uniforms for tennis; on socks, golf shoes, pants, dresses, shirts and hats for golf; and on socks, tennis shoes and volleyball uniforms for volleyball. Such sensors can be utilized to detect and measure, among other things: pressure experience by the wearable garment; total forces experienced by the wearable garment; rotation of the wearable garment; position of the wearable garment; acceleration and/or velocity of the wearable garment; interaction of sensors of the wearable garment with sensors described herein which are utilized in other aspects of the game (e.g., the area of play, other wearable devices etc.) and the moment and time (or duration) of any of these events.

Within other embodiments one or more pressure sensors, location sensors, GPS, accelerometers, gyroscopes, time measurement devices and temperature sensors can be included on protective gear, such as: helmets and pads for football; headbands for soccer; protective cups, gloves, catcher's mask and helmets for baseball; pads, and gloves and helmets for hockey. Such sensors can be utilized to detect and measure, among other things: pressure experience by the gear; total forces experienced by the gear; rotation of the gear; position of the gear; acceleration and/or velocity of the gear; interaction of sensors of the gear with sensors described herein which are utilized in other aspects of the game (e.g., the area of play, other wearable devices etc.) and the moment and time (or duration) of any of these events.

Within yet other embodiments of the invention one or more pressure sensors, location sensors, GPS, accelerometers, gyroscopes, time measurement devices and temperature sensors can be placed on or within competitive objects of the game (e.g., balls, pucks and the like). For example, sensors can be placed: on or within a football, soccer ball, basketball, baseball, hockey puck, tennis ball, golf ball, and/or volleyball. Such sensors can be utilized to detect and measure, among other things: pressure experience by the object; total forces experienced by the object; rotation of the object; position of the object; acceleration and/or velocity of the object; interaction of sensors of the object with sensors described herein which are utilized in other aspects of the game (e.g., the area of play, other wearable devices etc.) and the moment and time (or duration) of any of these events.

Within yet other embodiments of the invention one or more pressure sensors, location sensors, GPS, accelerometers, gyroscopes, time measurement devices and temperature sensors can be placed on or within instruments and/or implements of the game (e.g., sticks, bats, and the like). For example, one or more sensors can be placed: on or within a baseball bat, a hockey stick, a tennis racket, and/or a golf club. Such sensors can be utilized to detect and measure, among other things: pressure experience by the implement; total forces experienced by the implement; rotation of the implement; position of the implement; acceleration and/or velocity of the implement; interaction of sensors of the implement with sensors described herein which are utilized in other aspects of the game (e.g., the area of play, other wearable devices etc.) and the moment and time (or duration) of any of these events.

Within one embodiment of the invention, the sensor is a self-contained module "SM" having one or more sensors as described herein. The SM can include a sensor interface, a processor interface, battery management, and a wireless interface. Within preferred embodiments of the invention the SM will be less than 1 cubic centimeter in size, and more preferably, less than 0.9, 0.8. 0.7, 0.6, 0.5, 0.4, 0.3, 0.2, or 0.1 cubic centimeters in size. Within various embodiments the SM can be comprised of a solid outer core, or composed of flexible materials (e.g., a degradable or non-degradable outer polymeric surface). Within certain embodiments the SM may be relatively square and solid, and yet within other embodiments very thin, malleable and lengthy (as compared to its width and/or height). It can be constructed for a number of different applications provided herein.

Representative examples of sensors which can be utilized within the context of the present invention include accelerometers (acceleration, tilt, vibration, shock and rotation sensors), pressure sensors, contact sensors, position sensors, chemical sensors, tissue metabolic sensors, mechanical stress sensors, auditory sensors, time sensors and temperature sensors. Within particularly preferred embodiments the sensor is a wireless sensor, or a sensor connected to a wireless microprocessor. Within further embodiments the sports equipment or area of play can have more than one type of the above-noted sensors.

Within further embodiments, the sports equipment or area of play can contain one or more sensors at specified densities in specific locations. For example, the sports equipment or area of play can have a density of sensors of greater than one, two, three, four, five, six, seven, eight, nine, or ten sensors [e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these] per square centimeter of the device. Within other embodiments, the sports equipment or area of play can have a density of sensors of greater than one, two, three, four, five, six, seven, eight, nine, or ten sensors [e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these] per cubic centimeter of the device.

Within certain embodiments of the invention, the sports equipment or area of play is provided with a specific unique identifying number, and within further embodiments, each of the sensors which are utilized herein in, on or around the sports equipment or area of play each have either a specific unique identification number, or a group identification number [e.g., an identification number that identifies the sensor as accelerometers (acceleration, tilt, vibration, shock and rotation sensors), pressure sensors, contact sensors, position sensors, chemical sensors, tissue metabolic sensors, mechanical stress sensors and temperature sensors]. Within yet further embodiments, the specific unique identification number or group identification number is specifically associated with a position on, in or around the sports equipment or area of play.

Within various aspects of the invention the sensors provided herein can be utilized as a group or collective in order to monitor various aspects of the player and of the overall game. For example, the sensors provided herein can provide real-time kinematic data on the movement, acceleration, speed and forces of the various players, objects on the area of play. Such data can provide real-time (or delayed) imaging of the actual play.

Within other aspects of the invention methods are provided for monitoring sensors on sports equipment or an area of play as provided herein comprising the steps of transmitting a wireless electrical signal from a location on or within sports equipment or an area of play; receiving the signal; powering the sensor using the received signal; sensing data at the sensor; and outputting the sensed data from the sensor to a receiving unit.

Within other aspects of the invention methods are provided for imaging sports equipment or an area of play as provided herein, comprising the steps of (a) detecting the location of one or more SMs having sensors in or on the sports equipment or area of play; and (b) visually displaying the relative anatomical location of said one or more SMs having one or more sensors, such that an image of the sports equipment or area of play is created. Within various embodiments, the step of detecting may be done over time, and the visual display may thus show positional movement over time. Within certain preferred embodiments the image which is displayed is a three-dimensional image.

The integrity of the sports equipment or an area of play can be wirelessly interrogated and the results reported on a regular basis. This permits the status to be checked on a regular basis or at any time as desired by the subject and/or third party. Furthermore, the sports equipment or area of play can be wirelessly interrogated when signaled to do so (via an external signaling/triggering device) as part of "event recording"—e.g. when a subject experiences a particular event (e.g. pain, traumatic event, etc.) she/he signals/triggers the sensors to obtain a simultaneous reading in order to allow the comparison of subjective/symptomatic data to objective/sensor data. Matching event recording data with sensor data can be used as part of an effort to better understand and study events. Hence, within various embodiments of the invention, methods are provided for detecting and/or recording an event, comprising interrogating one of the SMs on the sports equipment and/or area of play as provided herein at a desired point in time. Within further embodiments the interrogation can be conducted over a period of time, to make a longer recording. Within related embodiments, the step of recording may be performed with one or more wired devices, or, wireless devices that can be carried, or worn (e.g., a cellphone, watch or wristband, shoe, and/or glasses).

Within yet other aspects of the invention methods, devices are provided suitable for transmitting a wireless electrical signal from one of the aforementioned sensors positioned on, in or around the sports equipment and/or area of play; powering the sensor using the received signal; sensing data at the sensor; and outputting the sensed data from the sensor to a receiving unit. Within certain embodiments the receiving unit can provide an analysis of the signal provided by the sensor.

The data collected by the sensors can be stored in a memory located within a SM, or on the sports equipment or area of play, or on an associated device (e.g., an external device such as a cellphone, watch, wristband, and/or glasses).

The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 10 is an illustration of a variety of sensors on the endzone of a football field, according to one embodiment of the invention.

FIG. 12 is an illustration of a variety of sensors on football pads and a football uniform, according to one embodiment of the invention.

FIG. 22 is an illustration of a variety of sensors on a basketball uniform and shoes, according to one embodiment of the invention.

FIG. 27 is an illustration of a variety of sensors on a baseball bat and glove, according to one embodiment of the invention.

FIG. 33 is an illustration of a variety of sensors on hockey skates, according to one embodiment of the invention.

FIG. 34 is an illustration of a variety of sensors on a hockey helmet, according to one embodiment of the invention.

FIG. 35 is an illustration of a variety of sensors on a hockey uniform (e.g., gloves, shoulder pads, elbow pads, pants and shin pads), according to one embodiment of the invention.

FIG. 38 is an illustration of a variety of sensors on a tennis racket, according to one embodiment of the invention.

FIG. 39 is an illustration of a variety of sensors on a tennis net, according to one embodiment of the invention.

FIG. 44 is an illustration of a variety of sensors on golf clothing, glove(s) and shoes, according to one embodiment of the invention.

FIG. 49 is an illustration of a variety of sensors on volley ball clothes, according to one embodiment of the invention.

DETAILED DESCRIPTION OF THE INVENTION

Figure 1:
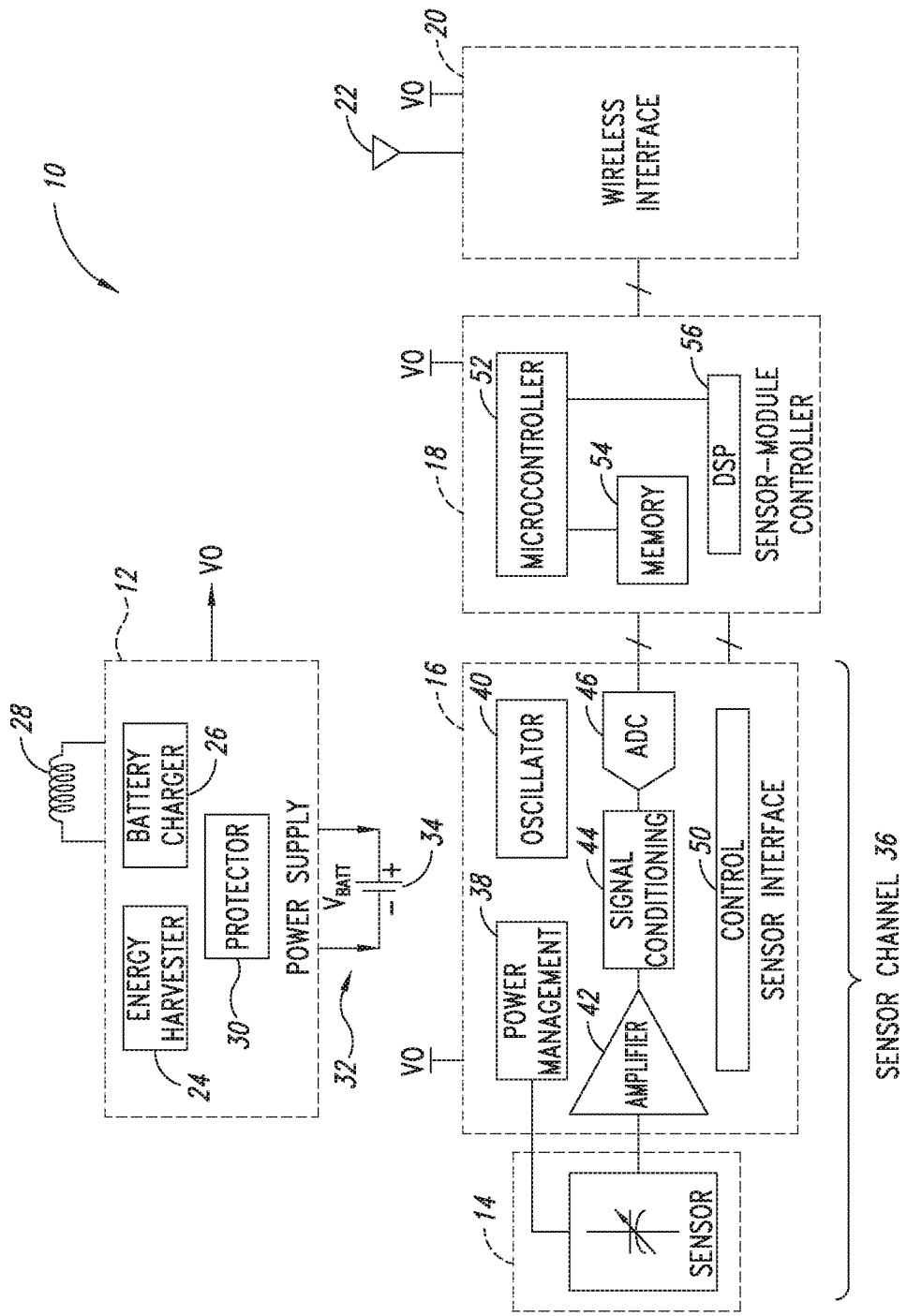
FIG. 1 is a diagram of a sensor module, according to an embodiment.

Briefly stated the present invention provides a variety of sports equipment and/or areas of play that have sensors that can perform a variety of functions. Prior to setting forth the invention however, it may be helpful to an understanding thereof to first set forth definitions of certain terms that are used hereinafter.

"Sport" or "sports" refers to forms of competitive physical activity which are based upon physical athleticism, skill and/or dexterity. According to the World Sports Encyclopedia (2003) there are over 8,000 recognized sports and sporting games. Representative examples of sports include: a) various forms of football (e.g., rugby, soccer, and American gridiron football); b) 'bat and ball' sports such as baseball and cricket; c) basketball; d) 'stick and ball' sports such as lacrosse, hockey and polo; e) racket sports such as badminton, racquetball, table tennis and tennis; f) golf; and g) ball and net sports such as volleyball.

"Sports equipment" refers to a) wearable garments and/or wearable devices associated with a sport (e.g., uniforms hats gloves and shoes); b) protective gear associated with a sport (e.g., helmets and pads); c) competitive objects of the game (e.g., balls, pucks and the like); and d) instruments of the game (e.g., sticks, bats, and the like).

"Area of play" refers to the area in which a sport is played. Typically areas of play include boundaries associated with play, as well as markers which are associated with the play (e.g., yard lines in football or the three point boundary in basketball). Representative examples of areas of play in include fields (e.g., football, soccer and baseball fields), courts (e.g., basketball, tennis, squash and volleyball courts), courses (e.g., golf courses), and rinks (e.g., ice rinks). The area of play may also include one or more objects that are associated with the area of play, including for example 'goal' objects which are associated with the game (e.g., a basketball hoop, the goalpost for American football, a plate or base for baseball, and the nets for tennis and volleyball, and the goal for hockey).

"Sensor" refers to a device that can be utilized to measure one or more different aspects of sports equipment and/or an area of play. Sensors include Microelectromechanical Systems or "MEMS", and Nanoelectromechanical Systems or "NEMS", and BioMEMS or BioNEMS, see generally https://en.wikipedia.org/wiki/MEMS). Representative examples of sensors suitable for use within the present invention include, for example, fluid pressure sensors, fluid volume sensors, contact sensors, position sensors such as GPS (global positioning system) sensors, pulse pressure sensors, blood volume sensors, blood flow sensors, chemistry (chemical) sensors (e.g., for blood and/or other fluids), metabolic sensors including tissue metabolic sensors (e.g., for blood and/or other fluids), accelerometers (including acceleration, tilt, vibration, shock and rotation sensors), mechanical stress sensors, mechanical pressure sensors, gyroscopes, strain gauges, auditory sensors, time sensors and temperature sensors. The sensor may respond to various stimuli or conditions, and/or transmit various signals including, e.g., location as by a global-positioning-system (GPS), accelerometer, Hall-effect, electrical, magnetic, thermal, pressure, radiation, optical, quantity-differential, capacitive, and time.

Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor. Representative patent documents, e.g., patents and patent publications and patent applications, which describe sensors useful in the present invention and the operation thereof, such as, for example, fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), mechanical stress sensors and/or temperature sensors include U.S. Patent Application Nos. 61/745,403; 61/787,861; 61/789,170; 61/838,317; 62/017,086; 62/017,099; 62/017,106; 62/017,116; 62/017,159; 62/017,161 and 62/301,575; PCT Application Nos. PCT/US13/77356; PCT/US14/28323; PCT/US2014/028381; PCT/US2014/043736; PCT/US2015/37823; PCT/US2015/37803; PCT/US2015/37825; PCT/US2015/37827; PCT/US2015/37828; and PCT/US2015/37810; U.S. Pat. Nos. 7,383,071, 7,450,332; 7,463,997, 7,924,267 and 8,634,928, and U.S. Publication Nos. 2010/0285082 and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 $cm^3$ Interferometric Accelerometer with Nano-g Resolution," *J. Microelectromechanical Sys.*, 11:3, June 2002, 182-187; all of the above of which are incorporated by reference in their entirety. The incorporation is for all purposes, where those purposes include but are not limited to the identification of sensors and the operation thereof, assemblies that incorporate sensors, methods for monitoring sensors, and the handling and analysis of data derived from sensors including storing and providing images from sensor data.

Within various embodiments of the invention the sensors described herein may be placed at a variety of locations and in a variety of configurations, on the inside of a sports equipment or area of play, within the body of the sports equipment or area of play, on the outer surfaces (or inner surfaces) of the sports equipment or area of play, between the sports equipment or area of play and other objects (e.g. other sports equipment or regions of the area of play). When the phrase 'placed in a sports equipment and/or area of play' is utilized, it should be understood to refer to any of the above embodiments (or any combination thereof) unless the context of the usage implies otherwise.

Within certain embodiments, the sports equipment and/or area of play comprises sensors at a density of greater than 1, 2, 3, 4, 5, 6, 7, 8, 9, 10 or greater than 10 sensors per square centimeter. Within other aspects, the sports equipment and/or area of play comprises sensors at a density of greater than 1, 2, 3, 4, 5, 6, 7, 8, 9, 10 or greater than 10 sensors per cubic centimeter. Within either of these embodiments, there can be less than 50, 75, 100, or 100 sensors per square centimeter, or per cubic centimeter. Within various embodiments, at least one or more of the sensors may be placed randomly, or at one or more specific locations within the sports equipment and/or area of plays described herein. In addition, the sensors may be placed in specific patterns (e.g., they may be arranged in the pattern of an X, as oval or concentric rings.

One type of sensors are a "Sensor Module" or "SM" is a sensing device which is configured to be placed in, within or on sports equipment and/or an area of play, and is configured to sense one or more physical quantities, to generate a signal that represents the sensed quantity, and to transmit the signal to a remote receiver. The SM may have one or more sensors as provided above. Within an embodiment, the signal may contain information encoded to represent one or more of a magnitude, phase, and type of the sensed physical quantity.

Within one embodiment of the invention, the SM is a self-contained module having one or more sensors as described herein, a sensor interface, a processor interface, battery management, and a wireless interface. Within preferred embodiments of the invention the SM will be less than 1 cubic centimeter in size, and more preferably, less than 0.9, 0.8. 0.7, 0.6, 0.5, 0.4, 0.3, 0.2, or 0.1 cubic centimeters in size. Within various embodiments the SM can be comprised of a solid outer core, or composed of flexible materials (e.g., flexible/malleable alloys, a degradable or non-degradable outer polymeric surface). Within certain embodiments the SM may be relatively square and solid, and yet with in other embodiments very thin, pliable and lengthy (as compared to its width and/or height). It can be constructed for a number of different applications. Sensor modules are also described in U.S. Provisional Patent Application No. 62/051,855 filed Sep. 17, 2014, U.S. Provisional Patent Application No. 62/184,820 filed Jun. 25, 2015, U.S. patent application Ser. No. 15/078,604, and PCT application PCT/US2015/050789 filed Sep. 17, 2015 and published on Mar. 24, 2016 as WO 2016/044651, all of which applications and publications are incorporated herein by reference in their entireties.

Additional patent documents that are incorporated herein in their entireties for all purposes are: U.S. Publication No. 20150335290, published Nov. 26, 2015; U.S. Publication No. 20160038087, published Feb. 11, 2016; U.S. Publication No. 20160029952, published Feb. 4, 2016; U.S. Publication No. 20160192878, published Jul. 7, 2016; PCT Publication No. WO2014/100795, published Jun. 26, 2014; PCT Publication No. WO2014/144070, published Sep. 18, 2014; PCT Publication No. WO2014/144107, filed Sep. 18, 2014; PCT Publication No. WO2014/209916, published Dec. 31, 2014; PCT Publication No. WO2015/200718, published Dec. 30, 2015; PCT Publication No. WO2015/200704, published Dec. 30, 2015; PCT Publication No. WO2015/200720, published Dec. 30, 2015; PCT Publication No. WO2015/200722, published Dec. 30, 2015; PCT Publication No. WO2015/200723, published Dec. 30, 2015; PCT Publication No. WO2015/200707, published Dec. 30, 2015; and PCT Publication No. WO2016/044651, published Mar. 24, 2016.

Additional sensors suitable for use in the present invention include optical systems including for example, miniaturized optics and/or optical systems (e.g., lenses, cameras, and other image capture systems) can be added into, on or within one of the can be utilized in: a sport (e.g., rugby, soccer, American gridiron football, baseball, cricket, basketball, lacrosse, hockey, polo, badminton, racquetball, table tennis, tennis and volleyball); in, or on sports equipment (e.g., wearable garments and/or wearable devices such as uniforms hats gloves and shoes; protective gear (e.g., helmets and pads); c) competitive objects of the game (e.g., balls, pucks and the like); and instruments of the game (e.g., sticks, bats, and the like); an in, on or outside of an area of play (e.g., football, soccer and baseball fields; basketball, tennis, squash and volleyball courts; golf courses), and roller or ice rinks) including associated objects of the area of play (e.g., a basketball hoop, goalpost, a plate or base for baseball, nets for tennis and volleyball, and the goal for hockey). Within preferred embodiments of the invention, the miniaturized optics and/or optical systems will be less than 2 mm, less than 1 mm, or less than 100 um in size. For example, within one embodiment of the invention 3D printed micro- and nano-optics with complex lens designs (see for example, Gissibl et al., "Two-photon direct laser writing of ultracompact mult-lens objectives", Nature Photonics 10, 554-560 (2016) can be manufactured with sizes around 100 μm. Such optics and/or optical systems provide high performance and functionality by quantitative measurements. Other examples of miniaturized optics and/or optical systems are described by, for example: Kim, J. Y. et al. Hybrid polymer microlens arrays with high numerical apertures fabricated using simple ink-jet printing technique. Opt. Mater. Express 1, 259-269 (2011); Bruckner, A. et al. Ultra-thin wafer-level camera with 720p resolution using micro-optics. In Proc. SPIE: Novel Optical Systems Design and Optimization XVII 91930 W (eds Gregory, G. G. & Davis, A. J.) (SPIE, 2014); Gissibl, T., Thiele, S., Herkommer, A. & Giessen, H. Submicrometre accurate free-form optics by three-dimensional printing on single-mode fibres. Nature Commun. 7, 11763 (2016); Blattmann, M., Ocker, M., Zappe, H. & Seifert, A. Jet printing of convex and concave polymer micro-lenses. Opt. Express 23, 24525-24536 (2015); and U.S. Pat. Nos. 9,170,371, 9,176,263, 9,176,051, 9,164,278, 9,164,276, all of which are incorporated by reference in their entirety.

Within yet other embodiments of the invention, one of the sensors provided herein may be a laser or plurality of lasers. Such lasers may be utilized to determine the breaking of a or contact with a boundary in an area of play an area of play (e.g., football, soccer and baseball boundaries and yard-markers; basketball, tennis, squash and volleyball courts boundaries; golf courses boundaries and obstacles), and roller or ice rinks perimeters or markers). Lasers can also be utilized to determine the breaking of a boundary, or contact with an object associated with area of play (e.g., a basketball hoop, goalpost, a plate or base for baseball, nets for tennis and volleyball, and the goal for hockey). Lasers can also be utilized to determine the movement, velocity, acceleration, and trajectory of a player, the player's sports equipment (e.g., wearable garments and/or wearable devices such as uniforms hats gloves and shoes; protective gear (e.g., helmets and pads), and of competitive objects of the game (e.g., balls, pucks and the like); and instruments of the game (e.g., sticks, bats, and the like). Utilizing additional knowledge with respect to the player, competitive object of the game or instrument of the game, other physical characteristics may be calculated (e.g., force and momentum). Representative examples of the use of lasers in sports include those described in U.S. Pat. Nos. 9,398,213 and 9,164,464, Representative Embodiments of Sports Equipment or Areas of Play and Uses of Sensor-Containing Sports Equipment or Areas of Play In order to further understand the various aspects of the invention provided herein, the following sections are provided below:

A. Sensors and Sensor modules;

B. Sports Equipment and Areas of Play Having Sensors (including B1—American Football; B2—Soccer; B3—Basketball; B4—Baseball; B5—Hockey; B6—Tennis; B7—Golf; and B8—Volleyball);

C. Further aspects of sports equipment and/or areas of play having sensors (including C.1 Methods for the manufacture of sports equipment and/or areas of play having sensors, and C.2 Uses of combinations of sensors.

D. Methods for Monitoring Heat Stroke and Exhaustion, as well as Hypothermia in Players of a Game.

E. Further Uses of Sensor-Containing Sports Equipment and/or Areas of Play;

F. Generation of Power from Sports Equipment and/or Areas of Play;

G. Imaging of Assemblies Comprising Sports Equipment and/or Areas of Play, Predictive Analysis and Predictive Maintenance;

H. Methods of Monitoring Assemblies Comprising Sports Equipment and/or Areas of Play; and I. Collection, Transmission, Analysis, and Distribution of Data from Assemblies Comprising Sports Equipment and/or Areas of Play.

A. Sensors and Sensor Modules

As noted above, the present invention provides a wide variety of sensors (including SM's) suitable for use in sports equipment and/or areas of play. FIG. 1 is a diagram of a sensor module 10, according to one embodiment of the invention. The sensor module 10 is configured to be placed in, within or on sports equipment and/or an area of play, and is configured to sense a physical quantity, to generate a signal that represents the sensed quantity, and to transmit the signal to a remote receiver (not shown in FIG. 1) for processing. Within an embodiment, the signal may contain information encoded to represent one or more of a magnitude, phase, and type of the sensed physical quantity.

The sensor module 10 may be suitable for applications that call for the sensing of one or more physical quantities of sports equipment, an area of play and/or a subject to which the module is attached. For example, the sensor module 10 may sense acceleration of a piece of sports equipment, and hence acceleration of a subject; the device that receives the signal may then generate a visual representation of the acceleration in response to the signal. Other applications include, but are not limited to, sensing one or more parameters (e.g., contact, pressure, position, movement, wear, stability).

The sensor module 10 includes a power supply 12, one or more sensors 14, a sensor interface 16, a sensor-module controller 18, a wireless interface 20, and an antenna 22. The supply 12, sensor(s) 14, channel 16, controller 18, interface 20, and antenna 22 may be disposed on one or more integrated-circuit dies that are respectively disposed in one or more integrated-packages to form one or more integrated circuits (ICs); and these one or more ICs may be disposed in (not shown in FIG. 1), is insertable into, or otherwise attachable to sports equipment or an area of play. Or, the sensor(s) 14 and the antenna 20, or any other of the aforementioned components, may be not be disposed on an IC die, but may be discrete components.

The power supply 12 is configured to generate a regulated supply signal (e.g., a regulated supply voltage $V_O$) to power the other components of the sensor module 10, and includes an energy harvester 24, a battery charger 26, a power coil 28, a protector 30, and a battery receptacle 32 for receiving a battery 34, according to an embodiment.

The regulated supply voltage $V_O$ may be in, for example, an approximate range of 1-24 Volts (V), according to an embodiment. Furthermore, although not shown in FIG. 1, the power supply 12 may generate more than one regulated supply signal.

The energy harvester 24 is configured to convert an environmental stimulus into an electrical current or voltage for charging the battery 34, according to an embodiment. For example, the harvester 24 may convert, into a battery-charging electrical current or voltage, one or more of body heat from the subject in which the sensor module 10 is inserted or otherwise attached, kinetic energy generated by a subject's movement, changes in pressure (e.g., barometric pressure), radio-frequency (RF) energy (e.g., ambient RF transmissions), and light.

The battery charger 26 includes the power coil 28, which is configured to generate a voltage and current in response to a near magnetic field generated by a power unit (not shown in FIG. 1), according to an embodiment; such near-magnetic-field charging may be similar to a technique for powering a smart card. For example, the battery charger 26 and coil 28 may be used to charge the battery 34 while the energy harvester 24 is unable to generate enough energy to charge the battery to a voltage level sufficient for proper operation of the sensing module 10.

The protector 30 protects the battery 34 from overcharging or other conditions that may damage the battery, and also protects the power supply 12 in case a load current drawn from the regulated voltage $V_O$ (or from another regulated supply signal that the power supply generates) exceeds a predetermined safe threshold. The protector 30 may also monitor temperature of battery 34 and make appropriate adjustments of safe thresholds. For example, the protector 30 may disable the energy harvester 24 and the battery charger 26 if the voltage across the battery 34 exceeds a predetermined safe threshold, and may also generate some type of alarm to indicate a malfunction. And, the protector 30 may limit the load current drawn from $V_O$ (or from another regulated supply signal) to a safe limit, or may otherwise disable the power supply 12 if the load current exceeds a predetermined safe threshold; for example, the protector may implement such a limit or disabling if the node carrying $V_O$ is short-circuited to ground.

And the battery 34 may be any type of rechargeable battery, such as a lithium-ion battery, that is suitable for use in an electronic device.

Still referring to FIG. 1, the one or more sensors 14 are each configured to sense a respective physical quantity to which the module is attached, and are each configured to generate a respective sensor signal that represents one or more of a magnitude, phase (if applicable), and type of the respective sensed quantity. Examples of such a physical quantity include, but are not limited to, a relative or absolute position of the sensor module 10, a movement (e.g., acceleration, velocity, rotation) of the sensor module, and the following quantities in the vicinity of the sensor module: an electric field, voltage, or current, a magnetic field, time, a temperature, a pressure (e.g., blood pressure), radiation, electrical conductivity, an optical intensity, a spatial or temporal differential in the physical quantity (e.g., a temperature differential, a pressure differential, or a voltage differential), a biological marker (e.g., a tumor marker, bacterial marker or DNA fragment), a chemical composition of a substance, and a chemical reaction or a byproduct thereof. Examples of the one or more sensors 14 include, but are not limited to, the following types of sensors: global-positioning-system (GPS), accelerometer, Hall-effect, electrical (e.g., current, voltage, and conductivity), magnetic, thermal, pressure, radiation, optical, time sensors or clocks, audio sensors, visual sensors (e.g., cameras), quantity-differential, capacitive, and microelectromechanical (MEMS). And examples of the sensor signal include an analog or digital voltage or current.

The sensor interface 16, which, together with the sensor(s) 14, forms a sensor channel 36, includes a power-management circuit 38, an oscillator 40, an amplifier 42, a signal conditioner 44, an optional analog-to-digital converter (ADC) 46, and a control circuit 50, according to an embodiment.

The power-management circuit 38 is configured to convert $V_O$ from the power supply 12 into one or more other supply voltages or supply currents for the sensor 14 and the circuits of the sensor interface 16. The power manager 38 may provide power to the sensor using a conductor or by induction using a coil. Sensor 14 may provide a signal to sensor interface 16 using one or more conductors or by induction using a coil. The coil used to provide power to sensor 14 may be the same coil that receives the signal from sensor 14. Alternatively, the coil used to provide power to sensor 14 may be separate from the coil that receives a signal from sensor 14.

The oscillator 40 generates one or more clock signals for the digital and mixed-signal circuits of the sensor interface 16, and, depending on the types of the one or more sensors 14, may generate an analog reference signal for the sensor(s) 14. For example, a sensor 14 may generate a sensor signal by modifying one or more of the frequency, amplitude, and phase of such an analog reference signal in response to a respective physical quantity. Examples of the oscillator 40 include a ring oscillator, an operational-amplifier-based oscillator, or other digital or analog oscillator.

The amplifier 42 is configured to amplify the sensor signal generated by a sensor 14, according to an embodiment. Although shown as a having a single-ended input and a single-ended output, the amplifier 42 may have one or both of a differential input and a differential output. Examples of the amplifier 42 include an operational amplifier (e.g., having a feedback configuration), a transconductance ($g_m$) amplifier (e.g., having an open-loop configuration), and a low-noise amplifier (LNA). If there are more than one sensor 14, then the sensor interface 16 may include a respective amplifier 42 for each sensor, or a mux that selects which sensor output is input to amplifier 42. The gain of amplifier 42 may be controlled by one or more of the signal conditioner 44, the ADC 46.

The signal conditioner 44 is configured to condition the amplified sensor signal from the amplifier 42 for reception by the ADC 46 if present, or for reception by the sensor-module controller 18 if the ADC is not present. For example, the conditioner 44 may be configured to adjust the amplitude and the DC offset of the amplified sensor signal so that it is compatible with the dynamic input range of the ADC 46, to remove noise from, or to otherwise filter, the amplified sensor signal, or to equalize the amplified sensor signal. In addition, the signal conditioner 44 may be configured to add error-correction coding (ECC) to the amplifier sensor signal.

If present, the ADC 46 is configured to convert the conditioned sensor signal from the analog domain to the digital domain; but if the sensor 14 is configured to generate the sensor signal in the digital domain, then the amplifier 42 and the signal conditioner 44 may be digital circuits, and the ADC 46 may be omitted as described above.

And the control circuit 50 is configured to control the operations of one or more of the power manager 38, oscillator 40, amplifier 42, signal conditioner 44, and ADC 46, and may be configured to control the operations of one or more other components of the sensor interface 16. For example, the control circuit 50 may include, or be coupled to, a memory (not shown in FIG. 1) that stores configuration data or programming instructions for the sensor(s) 14 or for the sensor interface 16, and may configure the sensor(s) 14 or the interface 16 in response to this data or these instructions upon power up of the sensor module 10. Furthermore, the control circuit 50 may be configured to control communications between the interface 16 and the sensor-module controller 18.

Still referring to FIG. 1, the sensor-module controller 18 is configured to control the operations of the power supply 12, the sensor channel 36, the wireless interface 20, and other components of the sensor module 10, according to an embodiment, and includes a microcontroller or microprocessor 52, a memory 54, and a co-controller or co-processor, such as a digital-signal processor (DSP) 56, according to an embodiment. For clarity, hereinafter the microcontroller/microprocessor 52 is referred to as a microcontroller, it being understood that the microcontroller may instead be a microprocessor.

The microcontroller 52, in cooperation with the DSP 56, is configured to process the signal from the sensor channel 36, to generate data from the processed signal, and to condition the signal for transmission by the wireless interface 20. For example, if the sensor 14 measures temperature, then the microcontroller 52 may convert the signal from the sensor interface 16 into a temperature value in units of Fahrenheit or Celsius; or, if the sensor measures pressure, then the microcontroller may convert the signal from the sensor interface into a pressure value in units of Pascal.

The memory 54 may include volatile memory and non-volatile memory, according to an embodiment. For example, the volatile memory may be configured to store the operating system and one or more applications executed by the microcontroller 52, and the non-volatile memory may be programmed to store configuration information for the sensor module 10, such configuration information including, but not limited to, the type of the sensor 14, the frequency signal generated by the oscillator, the gains of the amplifier 42 and the signal conditioner 44, and the level of the voltage $V_O$ generated by the power supply 12.

And the wireless interface 20 is configured to receive the data from the sensor-module controller 18, to modulate one or more carrier signals with the data, and to transmit, via the antenna 22, the modulated carrier signal(s) to a remote device (not shown in FIG. 1) for use by, e.g., the subject, trainer and/or coach. For example, the wireless interface 20 may be configured to operate according to a specification such as, but not limited to, one of the following specifications: Bluetooth®, near-field communication (NFC), Zig-Bee (IEEE 802.15), WiFi, wireless local area network (WLAN, IEEE 802.11).

Furthermore, the wireless interface 20 may be configured to receive a signal from a remote device (not shown in FIG. 1) via the antenna 22, and to provide this signal to the supply-module controller 18. For example, such a signal may include sensor-module configuration data or program instructions, or may include a request that the sensor-module 10 transmit specified data to the remote device. Examples of the remote device include, but are not limited to, a smart phone or tablet computer (FIG. 4), a computer system (FIG. 5), or another sensor module 10 (FIG. 6).

Still referring to FIG. 1, the operation of the sensing module 10 during a sensing mode is described, according to an embodiment.

The power supply 12 generates the regulated supply voltage $V_O$ (and perhaps one or more other regulated supply signals) from the voltage $V_{BATT}$ across the battery 34. For example, if the battery voltage $V_{BATT} > V_O$, then the power supply 12 steps down $V_{BATT}$ to $V_O$; the power supply may include a buck converter to perform such a voltage step down. Alternatively, if $V_{BATT} < V_O$, then the power supply 12 steps up $V_{BATT}$ to $V_O$; the power supply may include a boost converter to perform such a voltage step up.

The sensor 14 senses a physical quantity that the sensor is configured to sense, and provides to the sensor interface 16 a sensor signal that represents the sensed quantity.

The sensor interface 16 amplifies, conditions, and, if the sensor signal is an analog signal, converts the conditioned sensor signal to the digital domain via the amplifier 42, signal conditioner 44, and ADC 46, respectively.

The sensor-module controller 18 processes the conditioned (and possibly ADC converted) sensor signal from the interface 16, and generates data representing the sensed quantity. The controller 18 may store the generated data in the memory 54 for later retrieval, or may provide the data to the wireless interface 20.

And if the sensor-module controller 18 provides the data to the wireless interface 20, then the wireless interface modulates one or more carriers signals with the data from the sensor-module controller 18, generates a transmission signal from the one or more carriers signals, and transmits the transmission signal to a remote device (not shown in FIG. 1) via the antenna 22.

Still referring to FIG. 1, the operation of the sensing module 10 during a data-receiving mode is described, according to an embodiment.

The power supply 12 generates the regulated supply voltage $V_O$ (and perhaps one or more other regulated supply signals) from the voltage $V_{BATT}$ across the battery 34 as it does during the above-described sensing mode.

The wireless interface 20 senses a signal being received by the antenna 22 and notifies the sensor-module controller 18.

In response to the wireless interface 20 sensing the received signal, the sensor-module controller 18 instructs the wireless interface to demodulate, and, if necessary, decode, the received signal, recover the data from the signal, and provide the data to the sensor-module controller.

The sensor-module controller 18 analyzes the recovered data, and takes appropriate action. For example, if the data is configuration data, then the sensor-module controller 18 may load this data into a non-volatile portion of the memory 54, and initiate a configuration cycle so as to configure, or reconfigure, one or more portions of the sensing module 10 in response to the configuration data. Or, if this data is a command, then the sensor-module controller 18 may execute the command. For example, if the command is a request for the sensor module 10 to send specified other data to a remote device (not shown in FIG. 1), then the controller 18 sends the requested data via the wireless interface 20, which modulates one or more carrier signals with the requested data, generates a transmission signal from the one or more carriers signals, and transmits the transmission signal to a remote device via the antenna 22 as described above in conjunction with the sensing mode.

Still referring to FIG. 1, alternate embodiments of the sensor module 10 are contemplated. For example, any of the functions performed by the sensor module 10 may be performed either by dedicated hardware, configurable hardware [e.g., a field-programmable gate array (FPGA)], a microprocessor or microcontroller executing program instructions, or a combination or sub-combination of dedicated hardware, configurable hardware, and a microprocessor or microcontroller executing program instructions. Furthermore, although the sensor module 10 is described as including components disposed in a single housing, the sensor module may include multiple housings/pieces. Moreover, although described as being inserted or otherwise attachable to a subject, the sensor module 10 may be configured to be disposed with any of the sports equipment or areas of play described herein.

Figure 2:
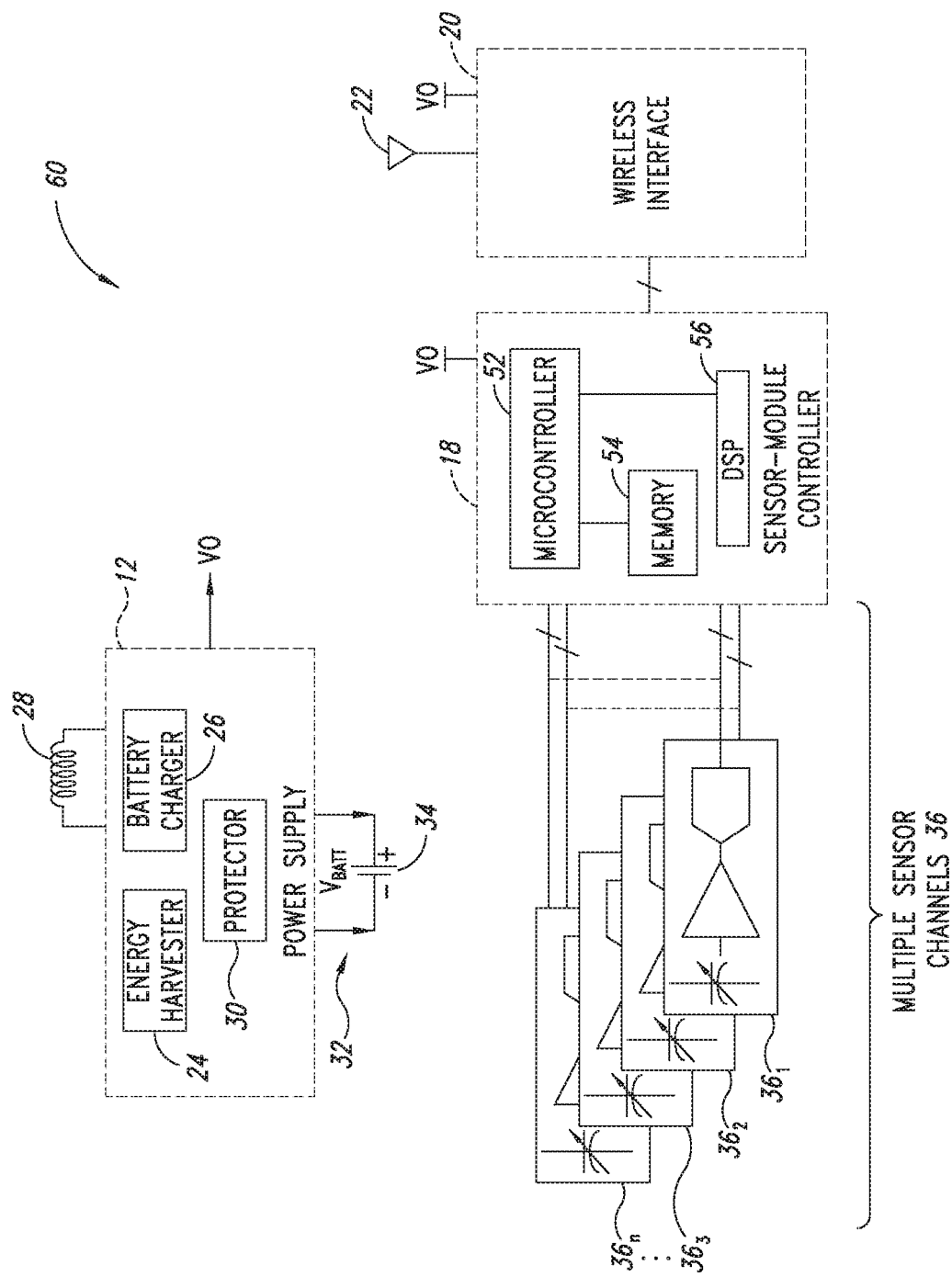
FIG. 2 is a diagram of a sensor module that includes multiple sensing channels, according to an embodiment.

FIG. 2 is a diagram of a sensor module 60, according to an embodiment. The sensor module 60 is similar to the sensor module 10 of FIG. 1, except that the sensor module 60 includes multiple sensor channels $36_1$-$36_n$, each of which may have one or more sensors 14.

Figure 3:
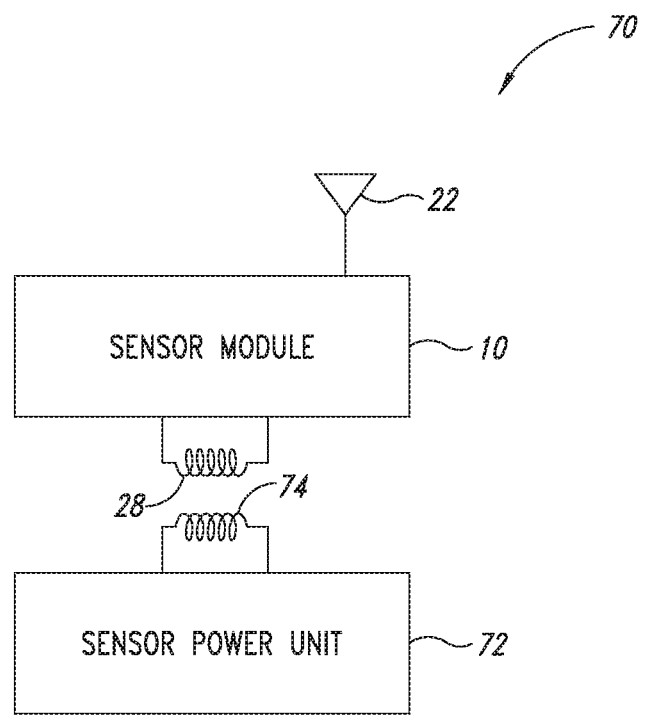
FIG. 3 is a diagram of a sensor-module power system, according to an embodiment.

FIG. 3 is a diagram of a sensor-module power-transfer system 70, according to an embodiment.

The system 70 includes the sensor module 10 of FIG. 1, and includes a sensor power unit 72 having a power coil 74. The sensor power unit 72 is configured to provide energy to the sensor module 10 in a manner similar to the manner in which a smart-card reader may power a smart card.

In operation during a power-transfer mode of the sensor module 10, one first positions the power coil 74 in near-field proximity (e.g., in an approximate range of 0-4 inches) to the power coil 28 of the sensor module.

Next, one activates the power unit 72, which generates, across the coil 74, an alternating (AC) voltage, which causes an alternating (AC) current to flow through the coil.

Because the power coil 74 is in near-field proximity to the power coil 28, the coils are magnetically (i.e., inductively) coupled such that each coil acts as a respective winding of a transformer.

Due to the inductive coupling between the coils 28 and 74, the magnetic flux generated by the AC current flowing through the coil 74 magnetically induces an AC current through, and an AC voltage across, the coil 28.

Consequently, the charger 26 of the power supply 12 (FIG. 1) is configured to use the induced AC current through, and the induced AC voltage across, the coil 28 to charge the battery 34 (FIG. 1), or the power supply 12 may include circuitry that is configured to directly power the sensor module 10 from the induced AC current and voltage.

After the power-transfer mode is complete, one deactivates the sensor power unit 72 and removes the coil 74 from near-field proximity with the coil 28.

Still referring to FIG. 3, alternate embodiments of the sensor-module power system 70 are contemplated. For example, the system 70 may include the sensor module 60 of FIG. 2 instead of the sensor module 10 of FIG. 1. Or the system 70 may include more than one sensor module (e.g., one or more of one or both sensor modules 10 and 60) or more than one power unit 72. Furthermore, as described above in conjunction with FIG. 1, while the coil 74 is not in near-field proximity with the sensor module 10, or while the power unit 72 is inactive, the power supply 12 of FIG. 1 may convert other sources of energy (e.g., kinetic energy, temperature-induced energy, pressure-induced energy) into a voltage and current suitable to charge the battery 34 (FIG. 1) or to power the sensor module 10.

Figure 4:
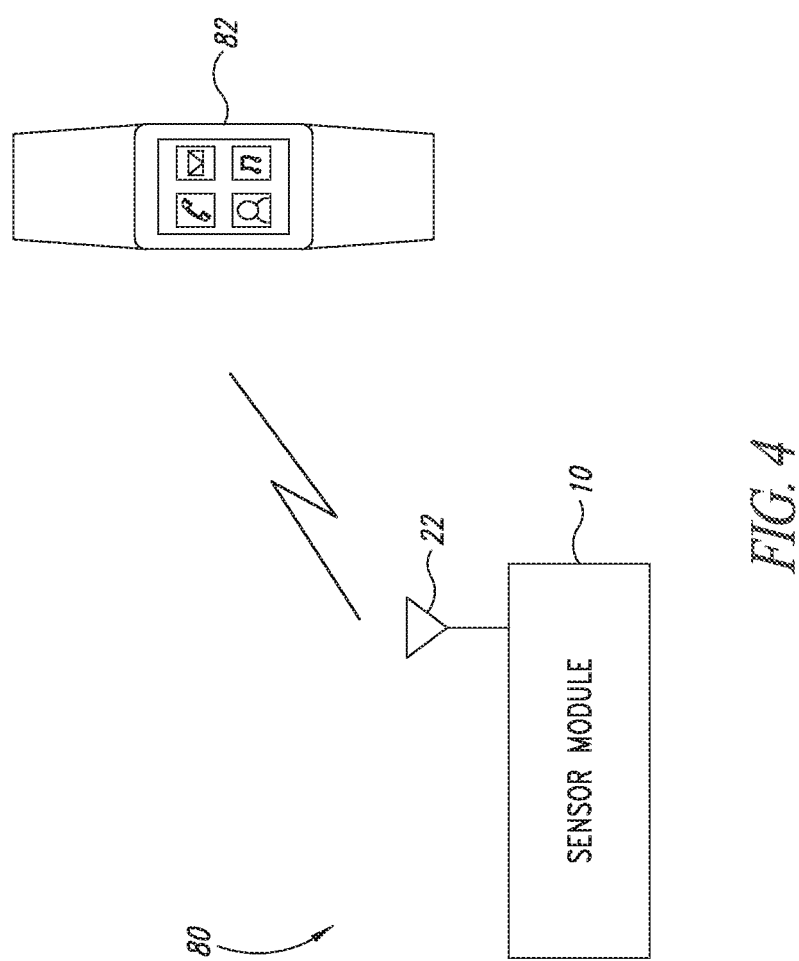
FIG. 4 is a diagram of a sensor-module data system, according to an embodiment.

FIG. 4 is a diagram of a sensor data system 80, according to an embodiment.

The sensor data system 80 includes the sensor module 10 of FIG. 1 and a remote data-receiving device 82.

The remote data-receiving device 82 may be, or include, a smart phone or tablet computer having circuitry sufficient to receive, demodulate, and recover sensor data from the wireless signal that the sensor module 10 transmits via the antenna 22. And the device 82 may also be configured to analyze, or otherwise process, the recovered sensor data. For example, the device 82 may be configured to display the recovered sensor data (e.g., acceleration), to make a recommendation or warning (e.g., "substantial concussion") in response to the sensor data, or to store the sensor data for later processing by the device 82 or by another device or for later review.

Still referring to FIG. 4, the operation of the sensor data system 80 is described, according to an embodiment.

First, the device 82 notifies the sensor module 10 that the device would like to receive sensor data, or the sensor module notifies the device that the sensor module would like to send sensor data to the device.

Next, the sensor module 10 and the device 82 establish communications using, e.g., a handshake technique.

Then, the sensor module 10 transmits a signal including the sensor data according to a communications protocol such as Bluetooth® or NFC.

Next, the device 82 receives the transmitted signal and recovers the data therefrom.

Then, the sensor module 10 notifies the device 82 when all of the data has been transmitted.

Next, the device 82 notifies the sensor module 10 that it has received all of the data, or that it needs the sensor module to resend some or all of the data (e.g., due to a communications error).

Then, the sensor module 10 notifies the device 82 if it has more data to send, or the device requests additional data from the sensor module. If the sensor module 10 sends additional data, then it does so according to the same procedure described above.

After the sensor module 10 is finished transmitting all available or requested data, it notifies the device 82, which acknowledges this notification to the sensor module.

Next, the sensor module 10 and the device 82 cease communicating with one another.

Then, the device 82 may display a representation of the recovered data, may make a recommendation or warning based on the recovered data, may transmit the data to another device, such as to a computer system at a doctor's office, via, e.g., a phone system, or may store the data for later access.

Still referring to FIG. 4, alternate embodiments of the sensor data system 80 are contemplated. For example, the system 80 may include the sensor module 60 of FIG. 2 instead of the sensor module 10 of FIG. 1. Or the system 80 may include more than one sensor module (e.g., one or more of one or both sensor modules 10 and 60) or more than one device 82. Furthermore, the data that the sensor module 10 sends to the remote device may be sensor-module-status data instead of, or in addition to, sensor data. Moreover, the remote device 82 may send data, such as configuration data or command data, to the sensor module 10.

Figure 5:
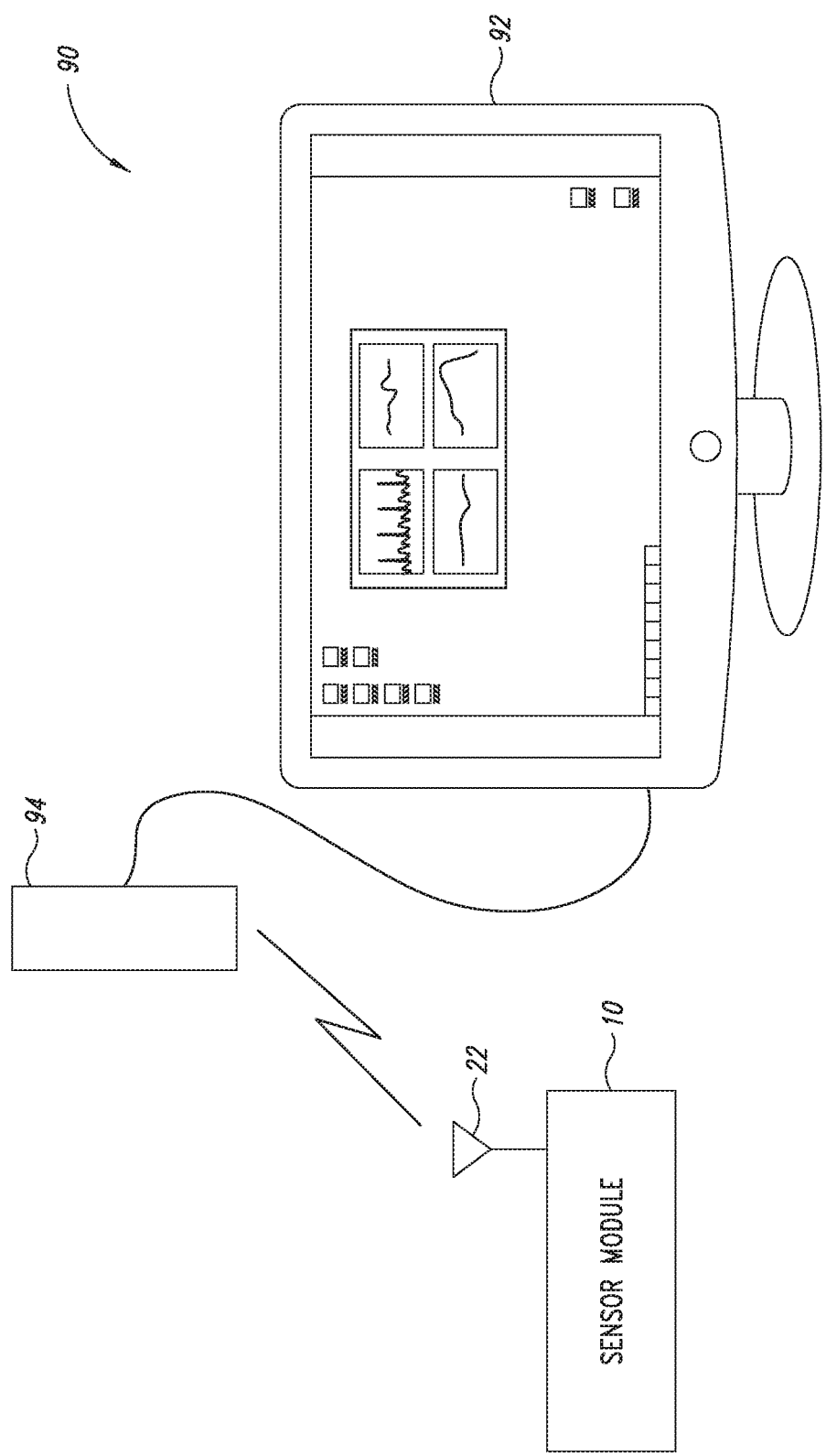
FIG. 5 is a diagram of a sensor-module data system, according to another embodiment.
Figure 6:
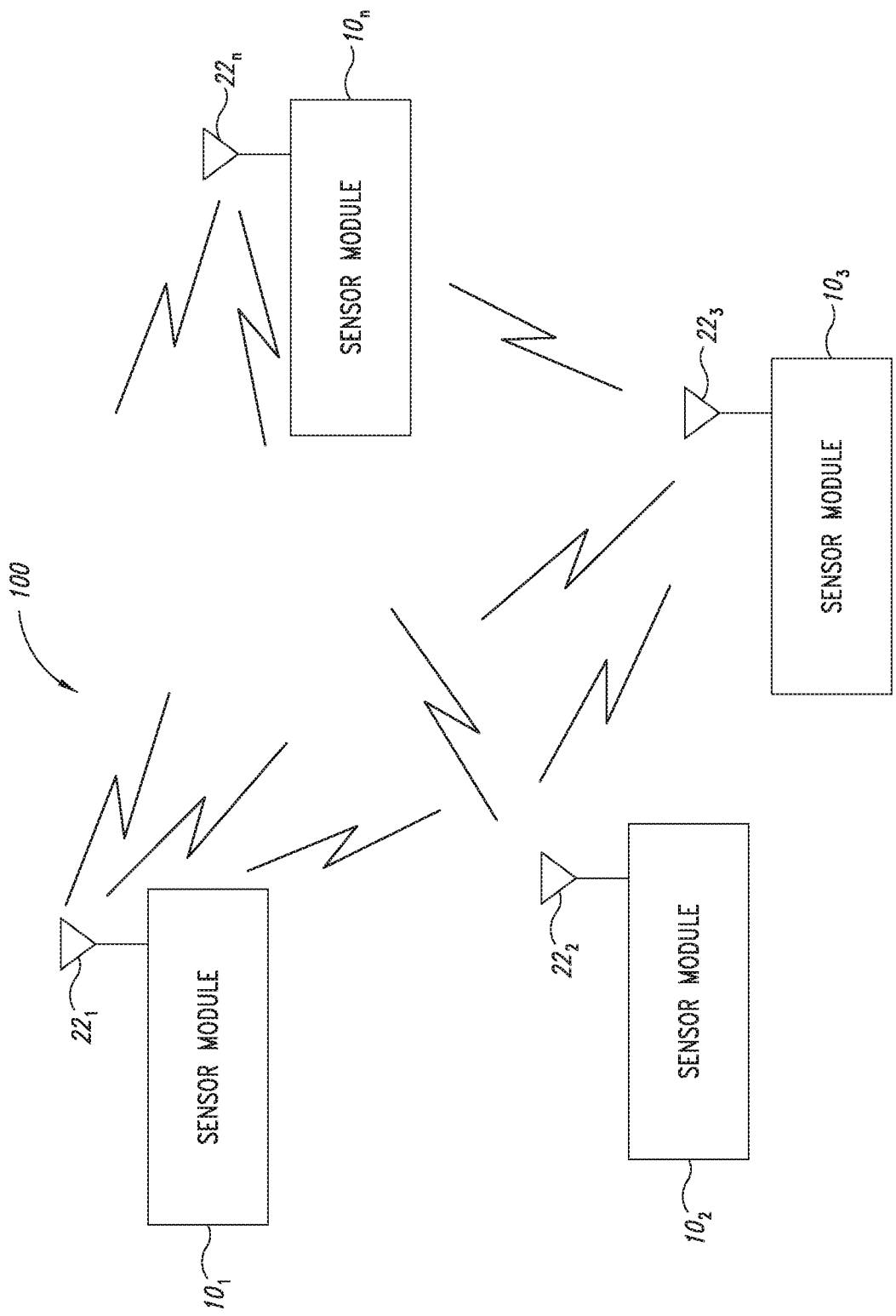
FIG. 6 is a diagram of a sensor-module network, according to an embodiment.
Figure 7:
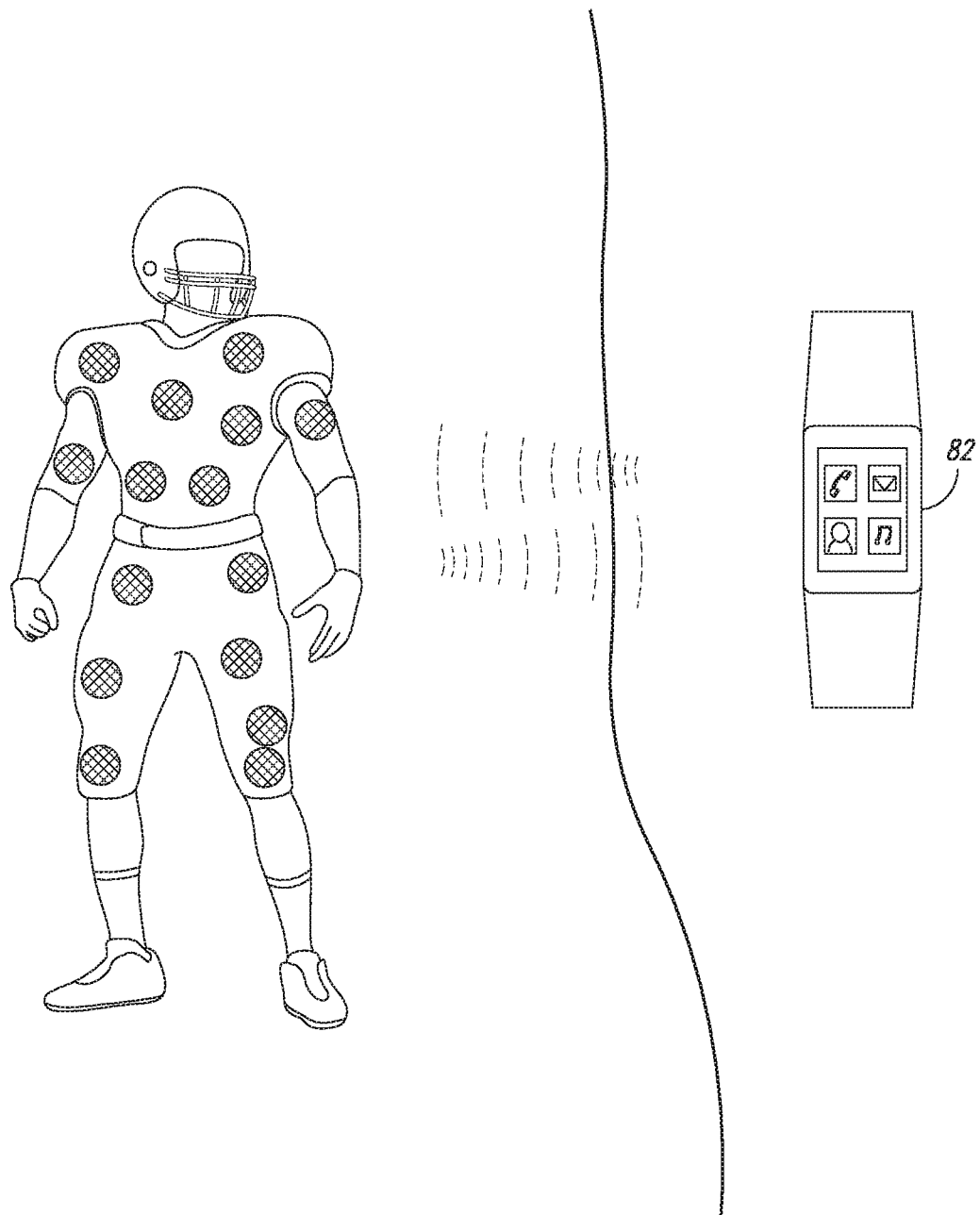
FIG. 7 is a schematic illustration of sensors positioned on sports equipment of a subject which is being probed for data and outputting data, according to one embodiment of the invention.

FIG. 5 is a diagram of a sensor data system 90, according to an embodiment.

The sensor data system 90 can be similar to the sensor data system 80 of FIG. 4, except that instead of the device 82, the system 90 includes a computer system 92 having a communication interface (e.g., a Bluetooth® interface) 94. The computer system 92 and the interface 94 can be configured to perform, together or separately, the operations that the device 82 of FIG. 4 is described as performing.

Still referring to FIG. 5, alternate embodiments of the sensor data system 90 are contemplated. For example, the system 90 may include the sensor module 60 of FIG. 2 instead of the sensor module 10 of FIG. 1. Or the system 90 may include more than one sensor module (e.g., one or more of one or both sensor modules 10 and 60) or more than one computer system 92. Furthermore, the data that the sensor module 10 sends to the computer system 92 may be sensor-module-status data instead of, or in addition to, sensor data. Moreover, the computer system 92 may send data, such as configuration data or command data, to the sensor module 10.

FIG. 6 is a diagram of a sensor-module network 100, according to an embodiment.

The network 100 includes multiple sensor modules 10 (FIG. 1), which are configured to communicate with one another using, e.g., ZigBee or another multi-node wireless-network protocol. For example, the sensor modules 10 may be inserted into, on or within sports equipment or areas of play as described herein.

Still referring to FIG. 6, the operation of the sensor-module network 100 is described, according to an embodiment.

First, when an initiating one of the modules 10 in the network 100 is ready to communicate with a responding one of the modules, the initiating module first determines if the communication channel is clear, i.e., that there are no other sensor modules currently using the channel for inter-module communications.

If the initiating module 10 determines that the communication channel is clear, then it notifies the responding sensor module that the initiating sensor module would like to receive sensor data or other data from the responding sensor module, or the initiating sensor module notifies the responding sensor module that the initiating sensor module would like to send sensor data or other data to the responding sensor module.

Next, the initiating and responding sensor modules 10 establish communications using, e.g., a handshake technique, and also inform the remaining sensor modules that the communication channel is being used.

Then, the initiating sensor module 10 transmits a signal including the sensor data; or, if the initiating sensor module is requesting data, then the responding sensor module transmits a signal to the initiating sensor module.

Next, the one of the initiating and responding sensor module 10 that is to receive the data receives the transmitted signal and recovers the data therefrom.

Then, the transmitting one of the initiating and responding sensor modules 10 notifies the receiving one of the initiating and responding sensor modules when all of the data has been transmitted.

Next, the receiving one of the initiating and responding sensor modules 10 notifies the transmitting one of the initiating and responding sensor modules that it has received all of the data, or that if needs the transmitting one of the initiating and responding sensor modules to resend some or all of the data (e.g., due to a communications error).

Then, the transmitting one of the initiating and responding sensor modules 10 notifies the receiving one of the initiating and responding sensor modules if it has more data to send, or the receiving one of the initiating and responding sensor modules requests additional data from the transmitting one of the initiating and responding sensor modules. If the transmitting one of the initiating and responding sensor modules 10 sends additional data, then it does so according to the same procedure.

After the transmitting one of the initiating and responding sensor modules 10 is finished transmitting all available or requested data, it notifies the receiving one of the initiating and responding sensor modules, which acknowledges this notification to the transmitting one of the initiating and responding sensor modules.

Next, the initiating and responding sensor modules 10 cease communicating with one another.

Then, the receiving one of the initiating and responding sensor modules 10 may use the recovered data for any suitable purpose.

Still referring to FIG. 6, alternate embodiments of the sensor-module network 100 are contemplated. For example, the network 100 may include sensor modules 60 of FIG. 2 instead of sensor modules 10 of FIG. 1. Or the network 100 may include one or more of one or both sensor modules 10 and 60.

B. Sports Equipment and Areas of Play Having Sensors

B.1. Football

As noted above, within one aspect of the invention sports equipment and areas of play are provided with sensors for the game of football. Briefly, football (sometimes referred to as American football or gridiron football) is a sport played by two opposing teams of eleven players each. The sport is played on a rectangular field with goalposts at each end. The team which has control of the oval shaped football attempts to advance the ball down the field by passing or running the ball, while the other team attempts to stop this advance.

Figure 8:
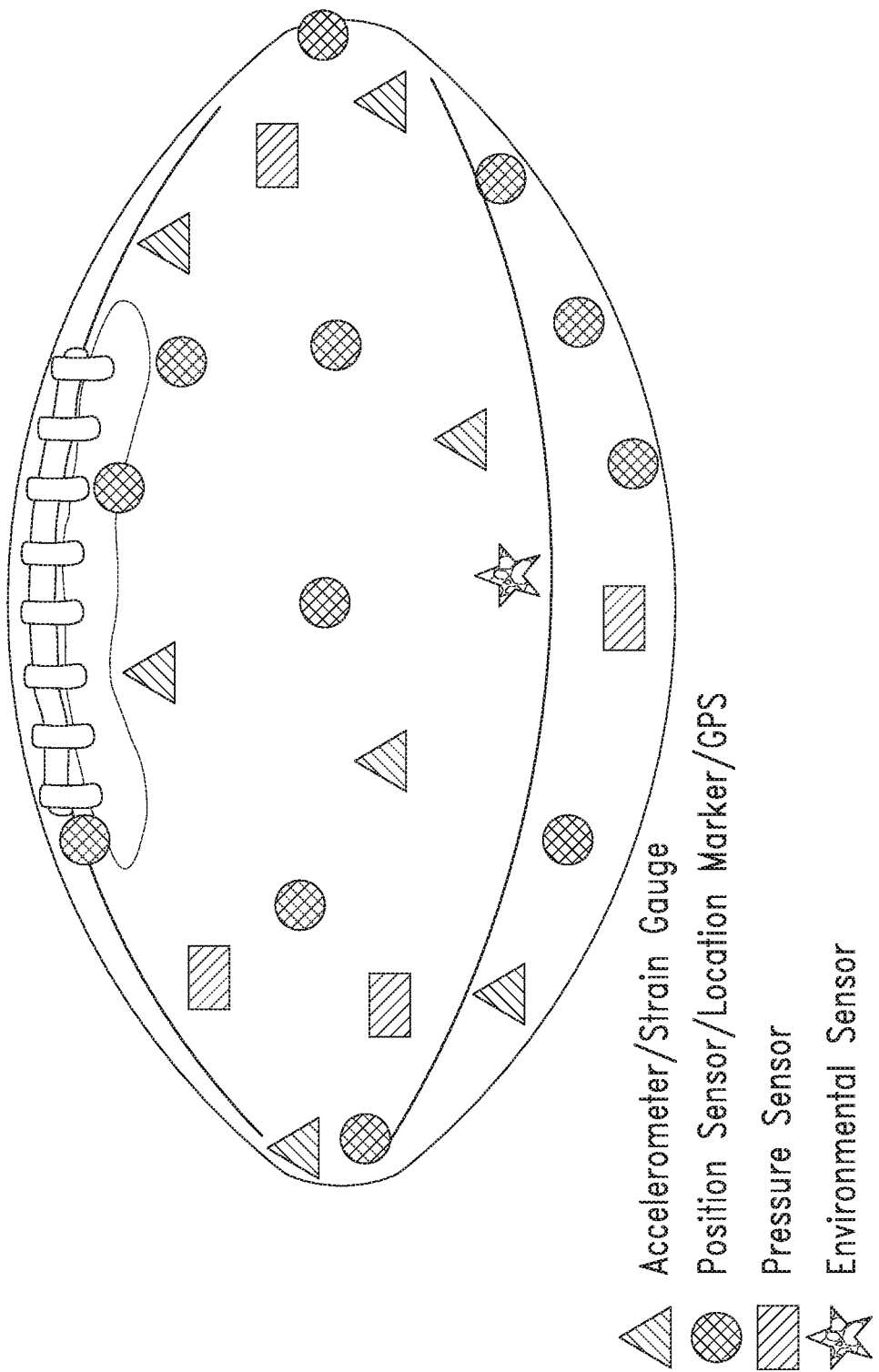
FIG. 8 is an illustration of a variety of sensors on a football, according to one embodiment of the invention.

Within one aspect of the invention a football is provided with one or more sensors (including for example sensor modules). For example, as shown in FIG. 8 one or more position sensors, location markers and/or GPS sensors may be contained on or within a football. The sensors can be distributed through the ball randomly or in an ordered manner. Such sensors can be utilized to track the ball from player to player, and/or across the area of play. The sensors can be utilized, among other things, to: a) determine the location of the ball on the field, to determine whether the ball is in-bounds or out of bounds; b) to determine the specific or relative location of the ball on the field (e.g., to determine the presence of a first down); c) to determine whether a ball has passed through the goal posts on a field goal; d) to determine if the ball has crossed the goal line and/or passed the end zone boundaries; e) to determine a forward pass and/or a backward or lateral pass; f) to determine which player has possession of the ball and/or the occurrence of a fumble; and g) to determine a catch.

Within related embodiments one or more environmental sensors can be placed on or within a football. Environmental sensors can be utilized to monitor the temperature, wind speed, humidity, moisture, and other environmental conditions such as air quality (e.g., pollution and/or pollen).

Within other embodiments, one or more pressure sensors can be placed on or within a football. Pressure sensors can be utilized to, amongst other things: a) determine contact with the ground; b) to determine possession by a player; c) and to determine impact of a ball against a surface.

Figure 9:
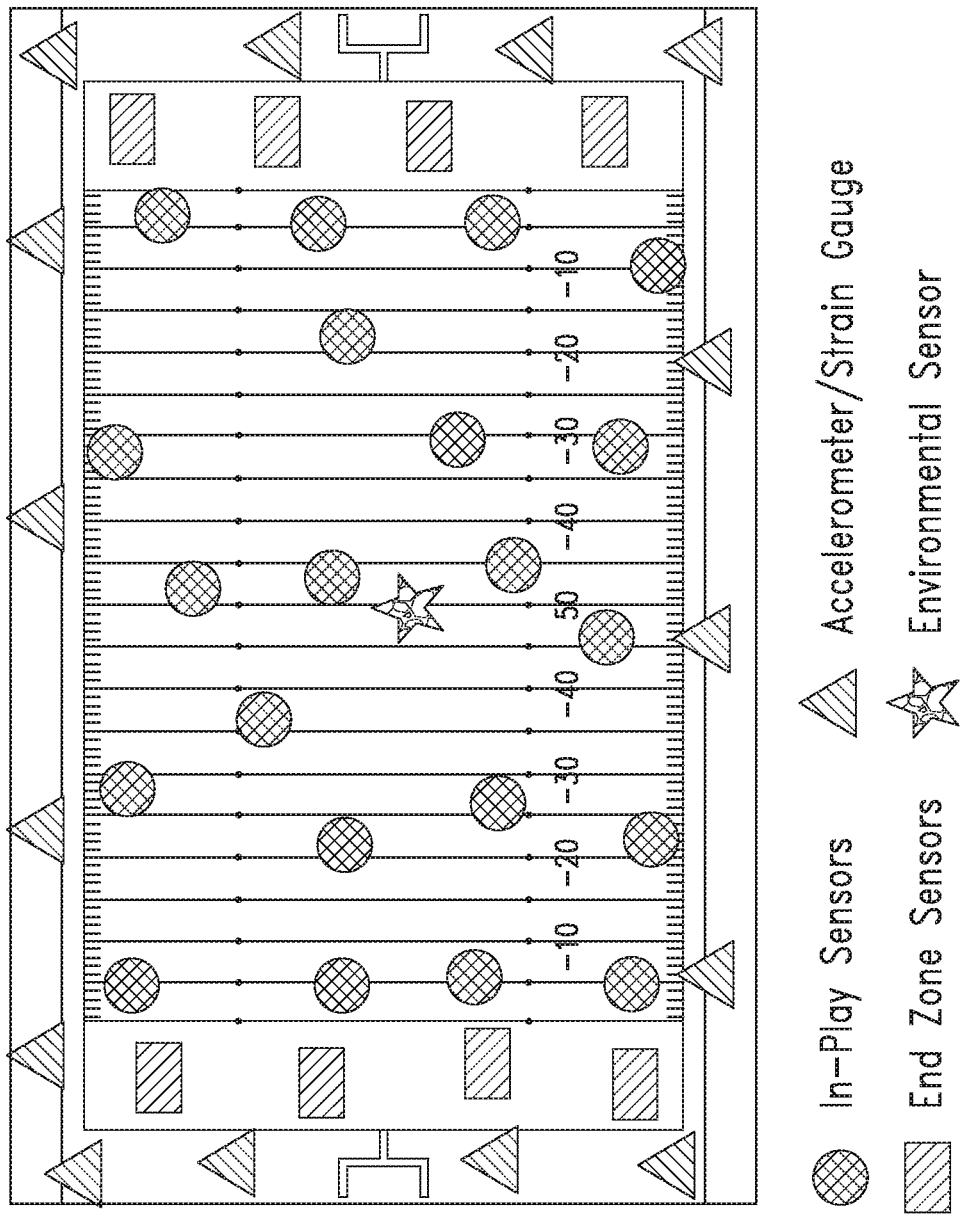
FIG. 9 is an illustration of a variety of sensors on a football field, according to one embodiment of the invention.

Within yet other embodiments one or more accelerometers, gyroscopes and/or strain gauges can be placed on or within a football. Such sensors can be utilized to determine, among other things: a) the speed, acceleration and/or velocity of the football; b) the direction of the football; c) the location of the football; d) forces which act upon the football (e.g., a kick, throw, pass, or catch of the football);

Within other aspects of the invention the area of play or football field (as shown in FIGS. 9 and 10) is set up to have one or more sensors. Sensors can be distributed randomly and/or specifically throughout the playing surface. For example, within one embodiment of the invention position sensors, locations markers, GPS sensors are provided for a football field. Such sensors can be utilized to determine in-bounds and out of bounds play. Within certain preferred embodiments of the invention field sensors can be utilized along with football sensors and/or equipment sensors (e.g., footwear, and uniform sensors) to determine actual play of the game. For example, by comparing the position or location of a field sensor with one or more ball or equipment sensors one can determine: a) the location of an event on the field; b) accurate position of the ball; c) a player who has control (or loses control) of a ball; d) distances (e.g., from the line of scrimmage or to a first down); e) for tracking play on the field; f) a forward, backward or lateral pass; g) penalties (e.g., offsides, false starts, illegal formations and illegal movement); h) touchbacks and safeties; i) whether feet are in-bounds or out of bounds; j) on pylons in the end zone; and k) placement of the ball for the start of a down.

Within other embodiments one or more environmental sensors can be utilized to monitor the temperature, wind speed, humidity, moisture, and other environmental conditions such as air quality (e.g., pollution and/or pollen).

Figure 11:
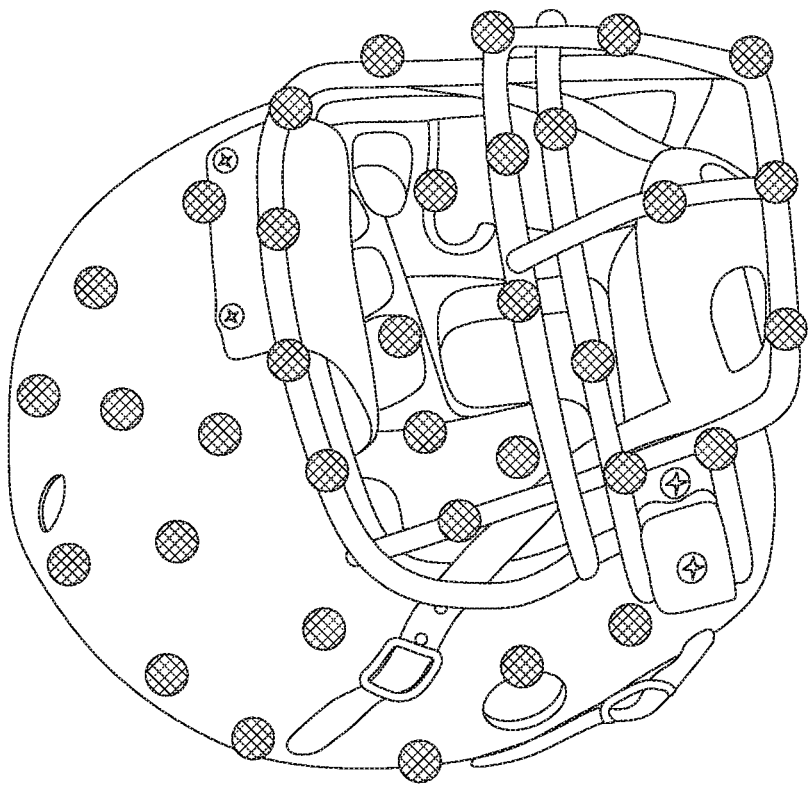
FIG. 11 is an illustration of a variety of sensors on a football helmet, according to one embodiment of the invention.

Within yet other aspects of the invention, one or more sensors are provided on the sportswear (e.g., helmets, pads, shoes, uniform, and/or gloves). For example, as shown in FIG. 11, one or more sensors such as position sensors, location markers, GPS indicators, accelerometers, gyroscopes and/or pressure sensors can be included on a football helmet. Such sensors can be distributed throughout the helmet (inside and out) randomly and/or in specific locations, such as on the face mask portion of the helmet.

The helmet sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from helmet sensors, optionally in combination with information obtained from internal or external sensors located elsewhere, may be used for various purposes. For example, information from helmet sensors may help to better understand an impact received by the helmet, where the impact may cause a head injury, and where exemplary relevant information is force, impact, rotation, and acceleration. Information about a head injury may be useful to provide a more complete understanding and characterization of the injury or traumatic event, which is valuable for many purposes, including insurance. As other examples, the sensor-derived information may be useful for improved equipment design, for on-going monitoring of equipment, for determining the effective lifespan of the equipment, for determining when equipment should be replaced, for comparing various pieces of equipment, for evaluating the degree of protection of a piece of equipment, optionally in comparison to the protection afforded by a different piece of equipment. The information obtained from sensors on a particular helmet or other piece of equipment will indicate the repetition of impact, and may provide information that is indicative of subclinical damage. The information from a helmet sensor may be used to evaluate or identify illegal behavior, such as spearing, a hit to the head, or face masking.

The sensor-containing helmet may be designed for use in American football, but it may alternatively be designed for use in other sports or recreational activities that require or may benefit from the use of a helmet. Examples of such activities include lacrosse, equestrian events, skiing, car racing, fencing, amateur boxing, cycling, skate boarding and motocross.

As another example, which is shown in FIG. 12, one or more sensors such as position sensors, location markers, GPS indicators, accelerometers, gyroscopes and/or pressure sensors can be included on a football shoe. Such sensors can be distributed throughout the shoe (inside and out) randomly and/or in specific locations, such as on the cleats of the shoe or clustered at the toe of the shoe.

The shoe sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from shoe sensors, optionally in combination with information obtained from internal or external sensors located elsewhere, may be used for various purposes. For example, information from shoe sensors may help to better understand an impact received by the shoe, where the impact may cause a foot injury, and where exemplary relevant information is force, impact, rotation, and acceleration. Information about a foot injury may be useful to provide a more complete understanding and characterization of the injury or traumatic event, which is valuable for many purposes, including insurance. As other examples, the sensor-derived information may be useful for improved equipment design, for on-going monitoring of equipment, for determining the effective lifespan of the equipment, for determining when equipment should be replaced, for comparing various pieces of equipment, for evaluating the degree of protection of a piece of equipment, optionally in comparison to the protection afforded by a different piece of equipment. The information obtained from sensors on a particular shoe or other piece of equipment will indicate the repetition of impact, and may provide information that is indicative of subclinical damage. The information from a shoe sensor may be used by trainers to guide the athlete to improved performance. Sensors located at the toe of the shoe may be used to monitor toe location (toe drag) while sensors located on the heel of the shoe may be used to monitor heel location, where this location information may be used, for example, to determine whether the shoe is within or out of bounds of the playing field.

In combination with sensors located elsewhere, such as ball sensors, field sensors and uniform sensors, the shoe sensor may provide valuable information for evaluating athletic performance or other uses such as positioning the athlete relative to other locations. In addition to determining whether the athlete was in-bounds or out-of-bounds at a particular time, the shoe sensor may help determine whether the athlete had two feet on the ground at a particular time, as is relevant for determining whether a reception was completed while in-bounds. The shoe sensor may also provide information that is relevant to accurate ball yard marking such as whether a first down has been completed, whether the player went out of bounds at any time, and whether the player achieved forward progress. The shoe sensor may help determine whether a touchdown was completed while the player was within the field zone. The shoe sensor can be used to track the player's movements around the field, which may be helpful for a television audience in order to enhance the viewer's experience. The shoe sensor will provide data that is useful in measuring the player's performance, where such information includes speed, acceleration, cutting, and power, where this performance information is of interest to athlete, the athlete's trainers and coaches, the team management who is evaluating the player, and the fans who are viewing the performance. The performance information may be used to evaluate kicking ability and obtain data related to kicking performance, such as in achieving field goals and punting. The shoe sensor may provide information that is relevant to assessing whether a penalty should be called, such as monitoring movement to evaluate off sides, motions, and illegal procedure.

Figure 13:
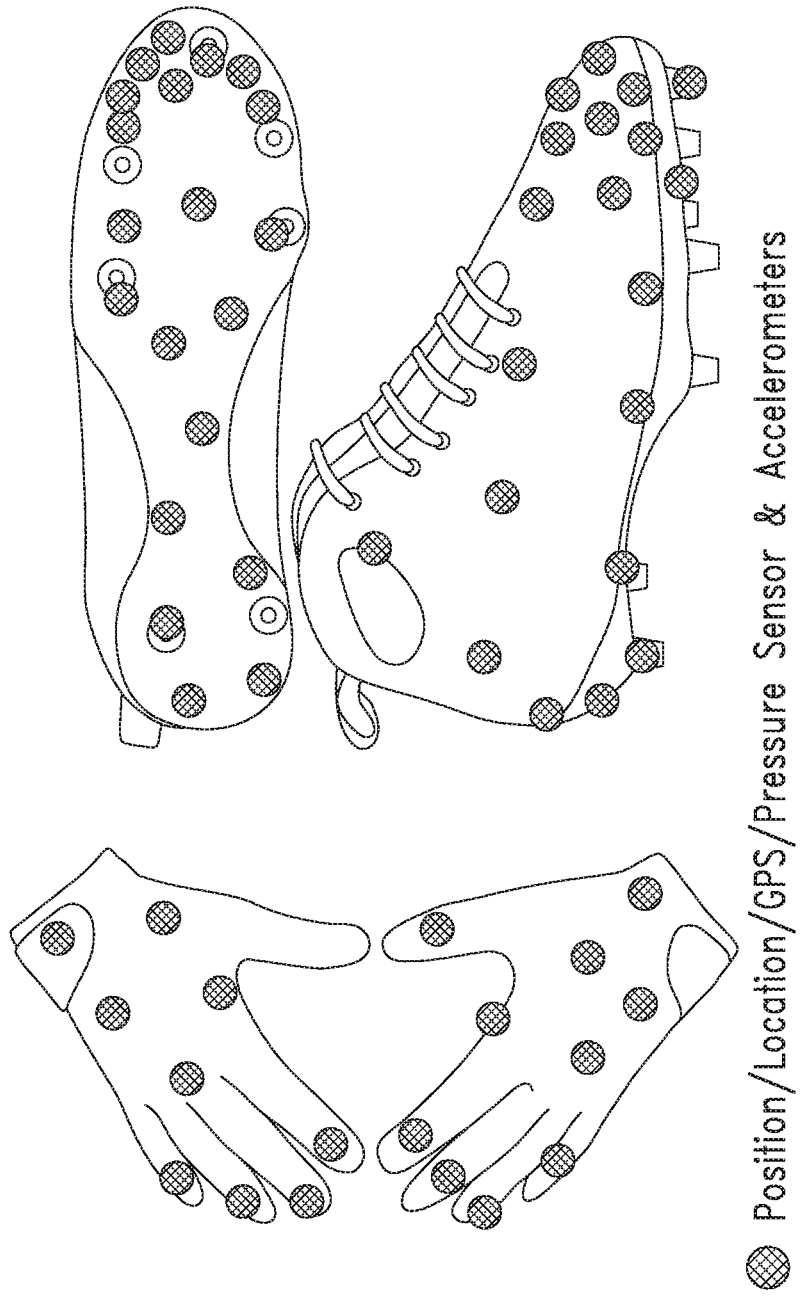
FIG. 13 is an illustration of a variety of sensors on football gloves and cleats, according to one embodiment of the invention.

As another example, which is shown in FIG. 13, one or more sensors such as position sensors, location markers, GPS indicators, accelerometers, gyroscopes and/or pressure sensors can be included on a glove. Such sensors can be distributed throughout the glove (inside and out) randomly and/or in specific locations, such as on the fingers of the glove, the back of the glove, or clustered at the palm of the glove.

The glove sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from glove sensors, optionally in combination with information obtained from internal or external sensors located elsewhere, may be used for various purposes. For example, information from glove sensors may help to better understand an impact received by the glove, where the impact may cause a hand injury, and where exemplary relevant information is force, impact, rotation, and acceleration. Information about a hand injury may be useful to provide a more complete understanding and characterization of the injury or traumatic event, which is valuable for many purposes, including insurance. As other examples, the sensor-derived information may be useful for improved equipment design, for on-going monitoring of equipment, for determining the effective lifespan of the equipment, for determining when equipment should be replaced, for comparing various pieces of equipment, for evaluating the degree of protection of a piece of equipment, optionally in comparison to the protection afforded by a different piece of equipment. The information obtained from sensors on a particular glove or other piece of equipment will indicate the repetition of impact, and may provide information that is indicative of subclinical damage. The information from a glove sensor may be used by coaches and trainers to guide the athlete to improved performance.

Sensors located on the glove may be used to differentiate between a ball catch vs. no catch situation, for example, to determine whether the player had possession of the ball, or whether there was a bobble. In combination with sensors located elsewhere, such as ball sensors, field sensors and uniform sensors, the glove sensor may provide valuable information for evaluating athletic performance or other uses such as positioning the athlete's hands relative to other locations. For instance, the glove sensors may assist in differentiating between a situations where the player catches the ball by having his hands under the ball at all relevant times, and when the ball hits the ground and/or bounces before the player grabs onto the ball. The glove sensors may be used to evaluate accurate ball yard marking, for example, whether a first down occurred, whether the player was out-of-bounds, or whether the player achieved forward progress. The glove sensors may be used to evaluate whether a touchdown occurred, such as by determining whether the player's hands crossed the plane and/or touched a pylon. The glove sensors may be used to assist in tracking the player's movement on television, which enhances the viewing experience of the fans. The glove sensors may be used to obtain useful data, such as data pertaining to catching, throwing, gripping, etc. of a ball. This data may be used by the athlete and his trainers/coaches as a training aid, by team management to evaluate the player, and by the fans to better understand the player's performance. The glove sensors may be used to identify and/or verify an appropriate penalty situation, such as may occur during holding, face masking, horse collar, hands to the face, and unsportsmanlike conduct. The glove sensors may be used to distinguish between a fumble and no-fumble situation, in order to identify possession, the ball coming loose, and hand moving forward in the case of quarterbacks.

One or more sensors such as position sensors, location markers, GPS indicators, accelerometers, gyroscopes and/or pressure sensors can be included on any equipment used by a football player of piece of uniform worn by a football player, such as protective equipment. Such sensors can be distributed throughout the equipment (inside and out) randomly and/or in specific locations.

The equipment and uniform sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from equipment and uniform sensors, optionally in combination with information obtained from internal or external sensors located elsewhere, may be used for various purposes. For example, information from equipment and uniform sensors may help to better understand an impact received by the player, where the impact may cause an injury, and where exemplary relevant information is force, impact, rotation, and acceleration. Information about an injury may be useful to provide a more complete understanding and characterization of the injury or traumatic event, which is valuable for many purposes, including insurance. As other examples, the sensor-derived information may be useful for improved equipment or uniform design, for on-going monitoring of equipment or uniform, for determining the effective lifespan of the equipment or uniform, for determining when equipment or piece of uniform should be replaced, for comparing various pieces of equipment or uniforms, for evaluating the degree of protection of a piece of equipment or uniform, optionally in comparison to the protection afforded by a different piece of equipment or uniform. The information obtained from sensors on a particular piece of equipment or uniform article may indicate the repetition of impact, and may provide information that is indicative of subclinical damage. The information from a sensor may be used by trainers to guide the athlete to improved performance.

Sensors located on the uniform or piece of equipment may be used to differentiate between a successful and non-successful action on the part of the athlete. For example, to distinguish whether the player had possession of the ball at a relevant time, or whether the player was in-bounds or out-of-bounds at the relevant time. In combination with sensors located elsewhere, such as ball sensors, field sensors and other equipment or uniform sensors, the sensor may provide valuable information for evaluating athletic performance or other uses such as positioning the athlete's head, hands, feet, knees, or chest, relative to other locations. For instance, the sensors may assist in differentiating between a situations where the player catches the ball by having his hands under the ball at all relevant times, and when the ball hits the ground and/or bounces before the player grabs onto the ball. The uniform or equipment sensors may be used to evaluate accurate ball yard marking, for example, whether a first down occurred, whether the player was out-of-bounds, or whether the player achieved forward progress. The uniform or equipment sensors may be used to evaluate whether a touchdown occurred, such as by determining whether the player's hands or feet crossed the plane and/or touched a pylon. The sensors may be used to assist in tracking the player's movement on television, which enhances the viewing experience of the fans. The uniform or equipment sensors may be used to obtain useful data, such as data pertaining to catching, throwing, gripping, etc. of a ball, or running with the ball or without the ball. This data may be used by the athlete and his trainers/coaches as a training aid, by team management to evaluate the player, and by the fans to better understand the player's performance. The uniform and equipment sensors may be used to identify and/or verify an appropriate penalty situation, such as may occur during disallowed movement (e.g., offside, illegal procedure), blocking (holding, blocking from behind, clipping, crackbacks), pass interference, illegal contact, etc. The uniform and equipment sensors may be used to monitor the physiology of the athlete, by measuring, for example, heart rate, blood pressure, internal temperature, glucose levels, etc.

B.2. Soccer

Association football, more commonly known as football or soccer, is a sport played between two teams of eleven players with a spherical ball. It is played by 250 million players in over 200 countries, making it the world's most popular sport. Football is player on a professional level, at the Olympic Games, and in colleges and high schools around the world. The game is played on a rectangular field with a goal at each end. The object of the game is to score by getting the ball into the opposing goal.

The goalkeepers are the only players allowed to touch the ball with their hands or arms while it is in play and then only in their penalty area. Outfield players mostly use their feet to strike or pass the ball, but may use their head or torso to strike the ball instead. The team that scores the most goals by the end of the match wins. If the score is even at the end of the game, either a draw is declared or the game goes into extra time and/or a penalty shootout depending on the format of the competition. The Laws of the Game were originally codified in England by The Football Association in 1863. Association football is governed internationally by the International Federation of Association Football (FIFA; French: Federation Internationale de Football Association) which organizes a World Cup every four years.

Figure 14:
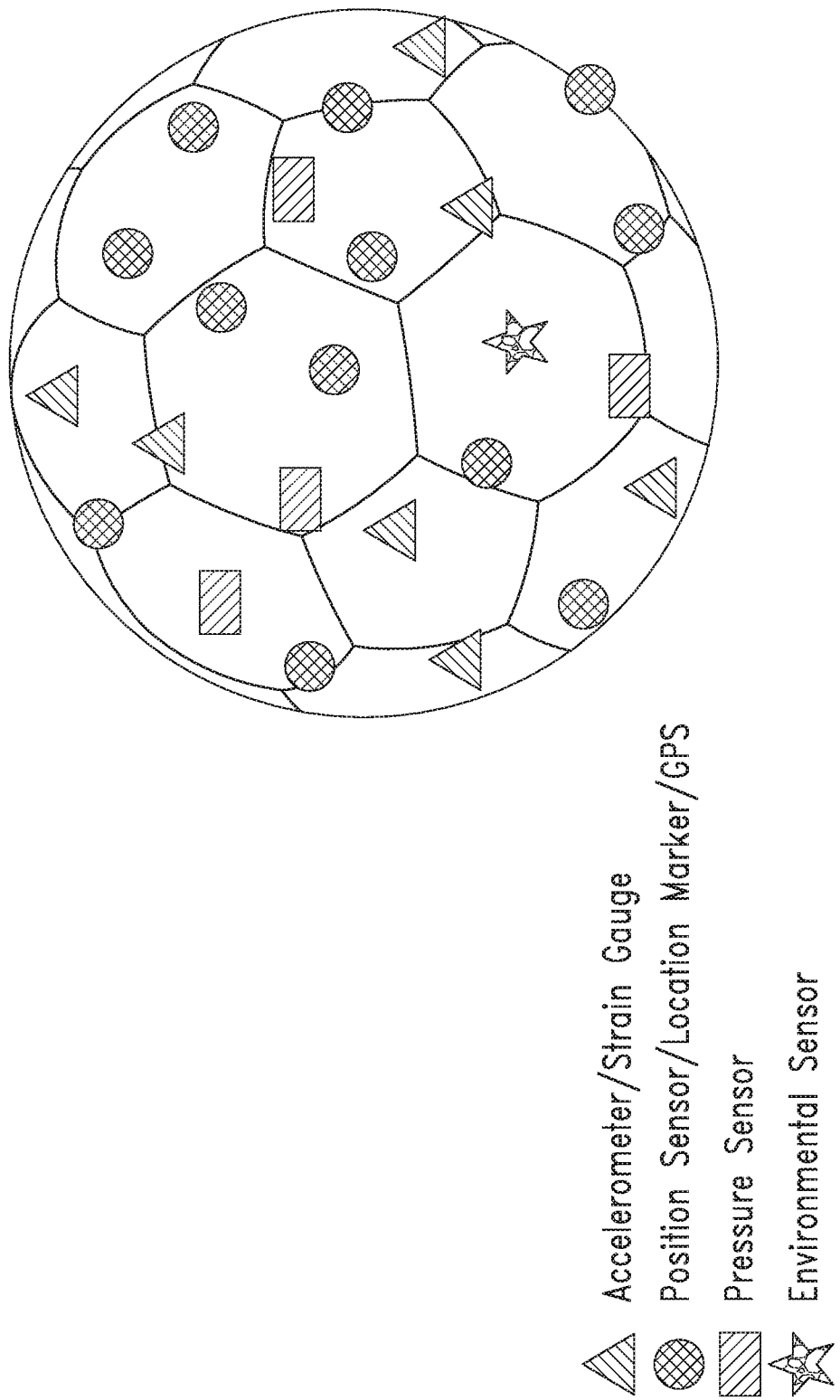
FIG. 14 is an illustration of a variety of sensors on a soccer ball, according to one embodiment of the invention.

Within one aspect of the invention a soccer ball is provided with one or more sensors (including for example sensor modules). For example, as shown in FIG. 14 one or more position sensors, location markers and/or GPS sensors may be contained on or within a soccer ball. The sensors can be distributed through the ball randomly or in an ordered manner. Such sensors can be utilized to track the ball from player to player, and/or across the area of play. The sensors can be utilized, among other things, to: a) determine the location of the ball on the field, to determine whether the ball is in-bounds or out of bounds; b) to determine the specific or relative location of the ball on the field; c) to determine whether a ball has passed through into the goal area; d) to determine a forward pass and/or a backward or lateral pass; f) to determine which player has possession of the ball; e) to determine which part of a player's body came into contact with the ball; and f) to determine how long a player was in contact with the soccer ball.

Within related embodiments one or more environmental sensors can be placed on or within a soccer ball. Environmental sensors can be utilized to monitor the temperature, wind speed, humidity, moisture, and other environmental conditions such as air quality (e.g., pollution and/or pollen).

Within other embodiments, one or more pressure sensors can be placed on or within a soccer ball. Pressure sensors can be utilized to, amongst other things: a) determine contact with the ground; b) to determine possession by a player; c) and to determine impact of a ball against a surface.

Within yet other embodiments, one or more accelerometers, gyroscopes and/or strain gauges can be placed on or within a soccer ball. Such sensors can be utilized to determine, among other things: a) the speed, acceleration and/or velocity of the soccer ball; b) the direction of the soccer ball; c) the location of the soccer ball; d) forces which act upon the soccer ball (e.g., a kick, throw, pass, or catch of the soccer ball). For example, the sensors may detect when the ball contacts the ground, or when the ball contacts a player and where the contact occurs on the player, e.g., on the player's foot, head or hand. The sensor may generally detect and measure forces and impacts acting on the soccer ball, including kicking, headers and goaltending.

Figure 15:
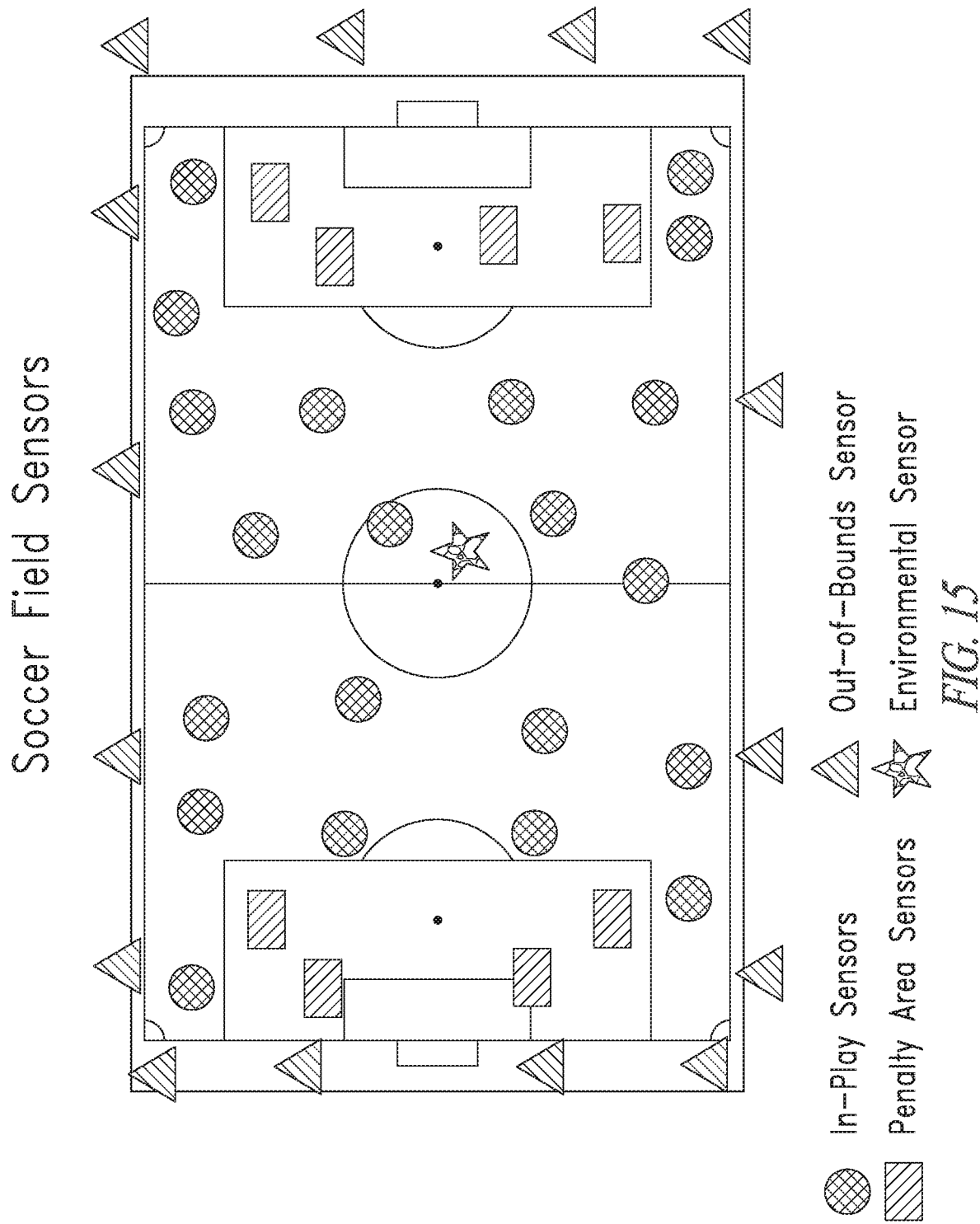
FIG. 15 is an illustration of a variety of sensors on a soccer field, according to one embodiment of the invention.

Within other aspects of the invention the area of play or soccer field (as shown in FIG. 15) is set up to have one or more sensors. Sensors can be distributed randomly and/or specifically throughout the playing surface. For example, within one embodiment of the invention position sensors, locations markers, GPS sensors are provided for a soccer field. Such sensors can be utilized to determine in-bounds and out of bounds play. Within certain preferred embodiments of the invention field sensors can be utilized along with soccer ball sensors and/or equipment sensors (e.g., footwear, and uniform sensors) to determine actual play of the game. For example, by comparing the position or location of a field sensor with one or more ball or equipment sensors one can determine: a) the location of an event on the field, e.g., when the soccer ball passes the goal line; b) accurate position of the soccer ball; c) a player who has control (or loses control) of a soccer ball; d) distances (e.g., between two players who are passing the ball from one to another); e) for tracking play on the field, e.g., whether the soccer ball is in bounds, out of bounds, or being subjected to a corner kick; f) a forward, backward or lateral kick; g) penalties (e.g., using hands to contact the ball, fouls that occur upon contact between players); h) whether feet are in-bounds or out of bounds; i) on pylons in the goal zone; j)

location of the ball when it is being thrown onto the field to start play; k) when the ball is in the penalty area; and l) tracking the ball for the benefit of a television audience.

Sensors which are particularly effective in monitoring in-play position and in-play events including location markers, GPS and pressure sensors. These sensors may be distributed throughout the in-bounds playing surface, in an organized manner or in a random manner. For instance, the sensors may be clustered adjacent to boundaries such as the side line and the end line. The sensors may provide information that is complementary to, or is interpreted in conjunction with, information from other sensors such as ball sensors, cleat sensors, and uniform sensors. Examples of uses include location on the field, particularly when combined with sensor information from a cleat, uniform or soccer ball; accurate ball yard marking on throw ins; accurate determination of corner kicks (end lines); tracking the soccer ball on television, particularly when the ball is obscured from view; and in combination with ball and player sensors, to determine offsides events.

Sensors which are particularly effective in monitoring position in the penalty area and penalty-area events including location markers, GPS and pressure sensors. These sensors may be distributed throughout the penalty area surface, in an organized manner or in a random manner. For instance, the sensors may be clustered adjacent to or on the goal line and/or adjacent to or on the penalty area lines, i.e., the lines that mark out the penalty area. For example, the goal line and on the lines marking out the penalty area may contain a particularly high density of sensors due to their importance in scoring. The sensors may provide information that is complementary to, or is interpreted in conjunction with, information from other sensors such as ball sensors, cleat sensors, and uniform sensors. Examples of uses include location on the field, which may answer questions such as did a foul occur in the penalty area.

Sensors which are particularly effective in monitoring out-of-play positions include location markers, GPA and pressure sensors. These sensors may be distributed throughout the out-of-play area surface, in an organized manner or in a random manner. The sensors may provide information that is complementary to, or is interpreted in conjunction with, information from other sensors such as ball sensors, cleat sensors, and uniform sensors. Examples of uses include location on the field, which in combination with cleat, uniform or ball sensors may answer the question of whether an event occurred in the out-of-play area on the in-play area; accurate ball yard marking which may be obtained when out-of-play sensor information is combined with other data indicating the ball is out-of-bounds; characterization of throw-ins; distinctions between goal kick and corner kick, by determining when and where the soccer ball crosses the end line; and which player last touched the soccer ball; tracking the soccer ball or the player's feet for the benefit of television watchers, particularly when the ball or feet are obscured from physical view.

Within other embodiments one or more environmental sensors can be utilized to monitor the temperature, wind speed, humidity, moisture, and other environmental conditions such as air quality (e.g., pollution and/or pollen) at the soccer field.

Figure 16:
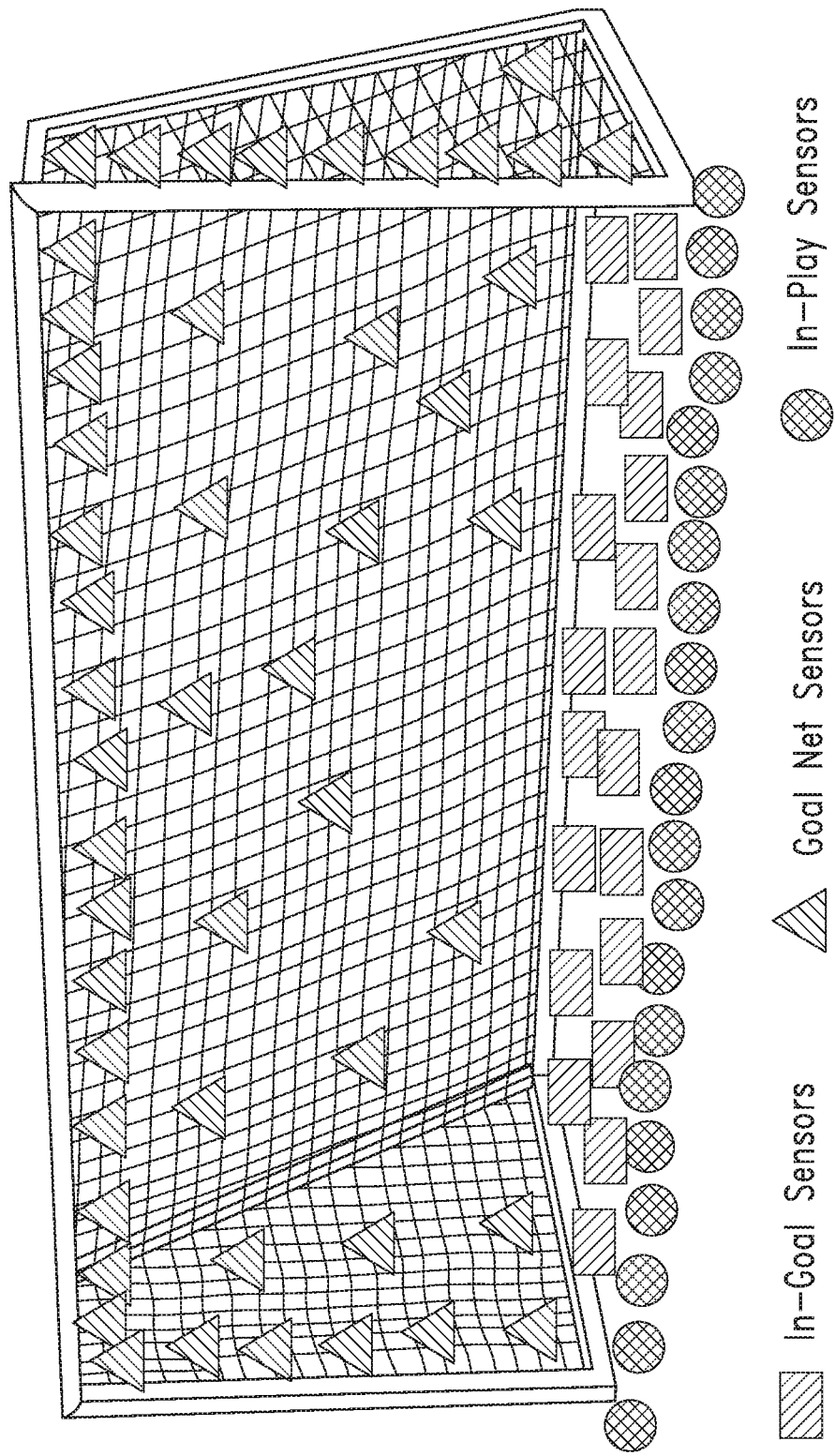
FIG. 16 is an illustration of a variety of sensors on a soccer net and goal line, according to one embodiment of the invention.

Within other embodiments one or more sensors are located on the soccer net and/or on or adjacent to the goal lines, and/or in the in-goal area of the playing field. These sensors may be monitored in conjunction with information received from sensors located in the in-play area of the field. For example, as shown in FIG. 16, one or more sensors may be included on, e.g., distributed throughout, the playing surface inside the net. The sensors may be clustered adjacent to the goal line, in particularly high density as needed to accurately recognize scoring events. The soccer net sensors may be monitored in combination with sensors on the soccer ball, to determine, for example, a scoring event, whether the ball breaks the plane of the goal line, and to track the ball as it nears the net, which may, for instance, assist television viewers, particularly when the ball and/or net is obscured from view. Sensors may be distributed on some or all of the soccer goal netting, in a uniform or random arrangement, for example, sensors may be clustered adjacent to the goal posts. These net sensors may be monitored in combination with sensors on the soccer ball as well as other sensors. Examples of use include identifying when the ball breaks the plane of the net, and tracking the ball, which may benefit television viewers, particularly when the ball is obscured. Sensors located on the goal line may help answer the question: did the ball completely cross the goal line?

Figure 17:
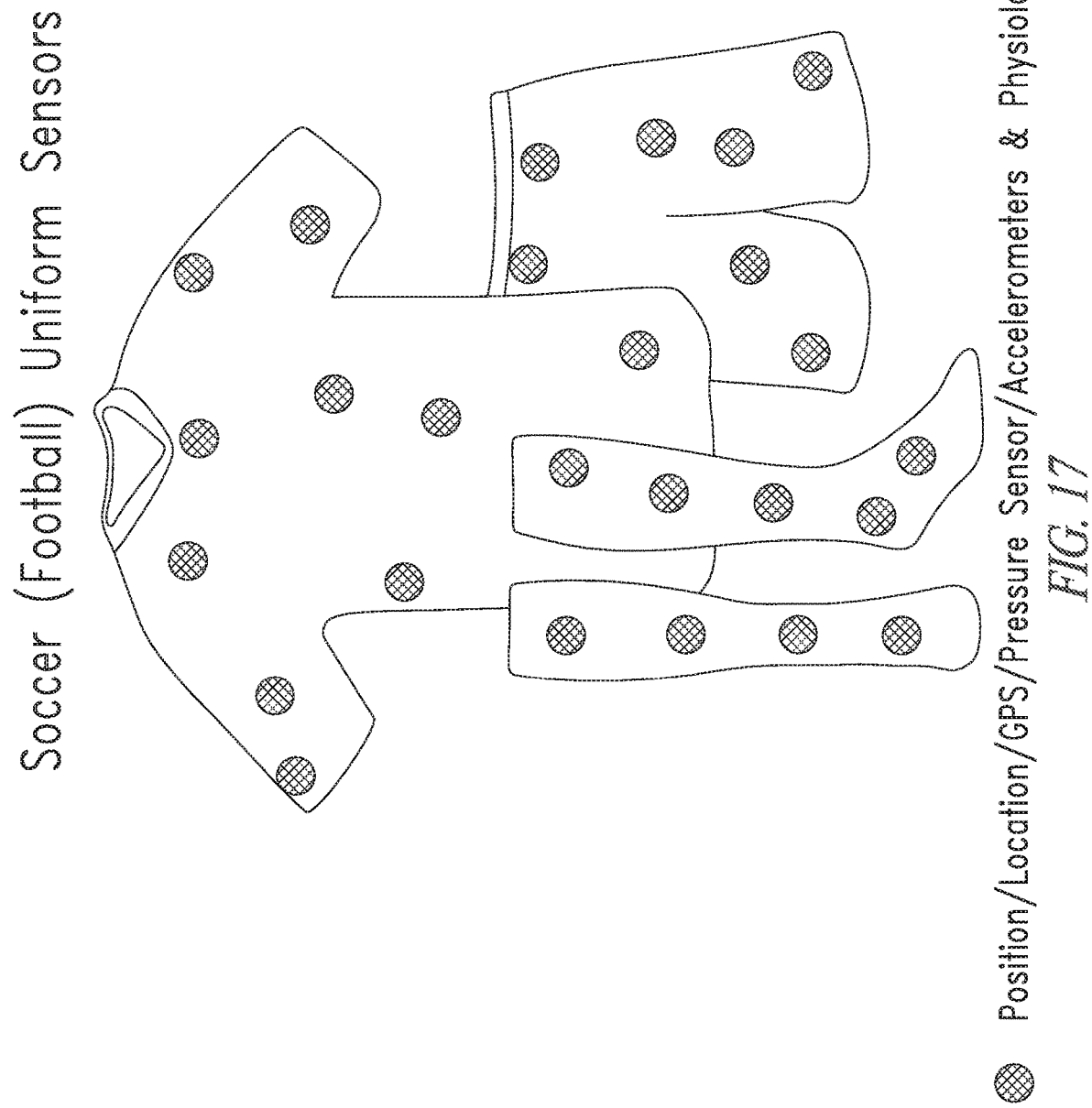
FIG. 17 is an illustration of a variety of sensors on a soccer uniform, according to one embodiment of the invention.

Within yet other aspects of the invention, one or more sensors are provided on the sportswear (e.g., shoes or uniform including shirt, shorts, and socks). For example, as shown in FIG. 17, one or more sensors such as position sensors, location markers, GPS indicators, accelerometers, gyroscopes, physiology sensors and/or pressure sensors can be included on the uniform, e.g., on any one or more of a shirt, sock and short worn by the soccer player. Such sensors can be distributed throughout the uniform (inside and out) randomly and/or in specific locations, such as on the shoulders or sleeves of the shirt.

The uniform sensor may be used in conjunction with other sensors, such as sensors that are located elsewhere on the player's uniform, on the player's equipment, sensors that are located on the uniform and/or equipment of another player, and/or sensors that are located on the field of play. Sensors located at various places, and/or sensors located at the same or nearly the same place but which respond to different stimuli or emit different signals, may be used in combination to provide more complete information about a specific time or event. In combination, the sensors may identify interactions between and differentiation of, different pieces of uniform, equipment, soccer ball, the field location.

The information obtained from shoe or uniform sensors, optionally in combination with information obtained from internal or external sensors located elsewhere, may be used for various purposes. For example, information from shirt sensors may help to better understand an impact received by the player wearing the shirt, where the impact may be an injury-causing impact, and where exemplary relevant information is force, impact, rotation, and acceleration. As other examples, the sensor-derived information may be useful for improved equipment design, for on-going monitoring of equipment, for determining the effective lifespan of the equipment, for determining when equipment should be replaced, for comparing various pieces of equipment, for evaluating the degree of protection of a piece of equipment, optionally in comparison to the protection afforded by a different piece of equipment. The information obtained from sensors on a particular piece of equipment will indicate the repetition of impact, and may provide information that is indicative of subclinical damage. The information from a uniform and/or shoe sensor may be used to evaluate or identify illegal behavior, such as tripping.

Figure 18:
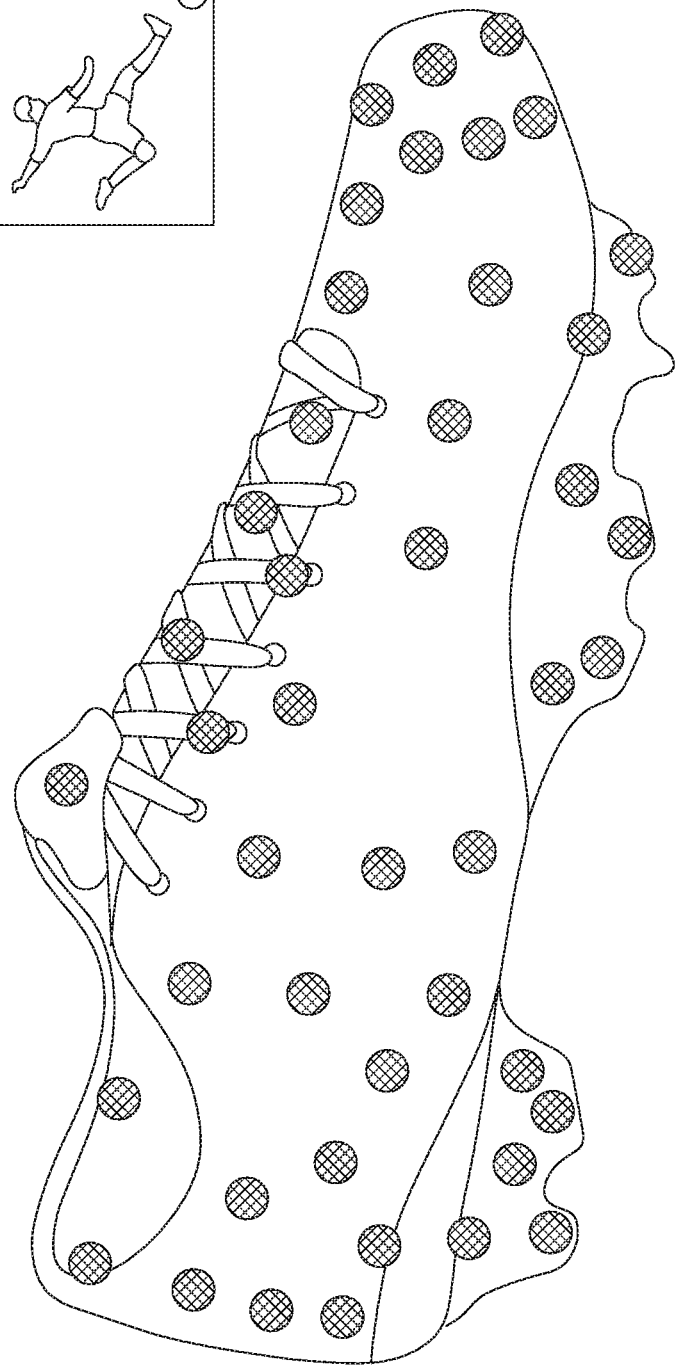
FIG. 18 is an illustration of a variety of sensors on a soccer shoe, according to one embodiment of the invention.

As another example, which is shown in FIG. 18, one or more sensors such as position sensors, location markers, GPS indicators, accelerometers, gyroscopes and/or pressure sensors can be included on a soccer shoe. Such sensors can be distributed throughout the shoe (inside and out) randomly and/or in specific locations, such as on the cleats of the soccer shoe or clustered at the toe of the soccer shoe. The shoe sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from shoe sensors, optionally in combination with information obtained from internal or external sensors located elsewhere, may be used for various purposes. For example, information from shoe sensors may help to better understand an impact received by the shoe, where the impact may cause a foot injury, and where exemplary relevant information is force, impact, rotation, and acceleration. Information about a foot injury may be useful to provide a more complete understanding and characterization of the injury or traumatic event, which is valuable for many purposes, including insurance. As other examples, the sensor-derived information may be useful for improved equipment design, for on-going monitoring of equipment, for determining the effective lifespan of the equipment, for determining when equipment should be replaced, for comparing various pieces of equipment, for evaluating the degree of protection of a piece of equipment, optionally in comparison to the protection afforded by a different piece of equipment. The information obtained from sensors on a particular shoe or other piece of equipment will indicate the repetition of impact, and may provide information that is indicative of subclinical damage. The information from a shoe sensor may be used by trainers to guide the athlete to improved performance.

In combination with sensors located elsewhere, such as ball sensors, field sensors and uniform sensors, the shoe sensor may provide valuable information for evaluating athletic performance or other uses such as positioning the athlete relative to other locations. In addition to determining whether the athlete was in-bounds or out-of-bounds at a particular time, the shoe sensor may help determine whether the athlete had two feet on the ground at a particular time. The shoe sensor can be used to track the player's movements around the field, which may be helpful for a television audience in order to enhance the viewer's experience. The shoe sensor will provide data that is useful in measuring the player's performance, where such information includes speed, acceleration, impact, and power, where this performance information is of interest to athlete, the athlete's trainers and coaches, the team management who is evaluating the player, and the fans who are viewing the performance. The performance information may be used to evaluate kicking ability and obtain data related to kicking performance, such as in achieving scores. The shoe sensor may provide information that is relevant to assessing whether a penalty should be called, such as monitoring movement to evaluate hand ball, fouls, contact vs. non-contact events (to help ferret out acting as though an injury or contact occurred), the amount and degree of a contact, and the location of a foul, e.g., did it occur in the penalty are. The shoe sensor may help determine whether one player kicked or tripped another player, or whether the player was off side at a particular time.

One or more sensors such as position sensors, location markers, GPS indicators, accelerometers, gyroscopes and/or pressure sensors can be included on any equipment used by a soccer player of piece of uniform worn by a soccer player, such as protective equipment. Such sensors can be distributed throughout the equipment (inside and out) randomly and/or in specific locations.

The soccer equipment and uniform sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from equipment and uniform sensors, optionally in combination with information obtained from internal or external sensors located elsewhere, may be used for various purposes. For example, information from equipment and uniform sensors may help to better understand an impact received by the player, where the impact may cause an injury, and where exemplary relevant information is force, impact, rotation, and acceleration. Information about an injury may be useful to provide a more complete understanding and characterization of the injury or traumatic event, which is valuable for many purposes, including insurance. As other examples, the sensor-derived information may be useful for improved equipment or uniform design, for on-going monitoring of equipment or uniform, for determining the effective lifespan of the equipment or uniform, for determining when equipment or piece of uniform should be replaced, for comparing various pieces of equipment or uniforms, for evaluating the degree of protection of a piece of equipment or uniform, optionally in comparison to the protection afforded by a different piece of equipment or uniform. The information obtained from sensors on a particular piece of equipment or uniform article may indicate the repetition of impact, and may provide information that is indicative of subclinical damage. The information from a sensor may be used by trainers to guide the athlete to improved performance.

Sensors located on the uniform or piece of equipment may be used to differentiate between a successful and non-successful action on the part of the athlete. For example, to distinguish whether the player had possession of the ball at a relevant time, or whether the player was in-bounds or out-of-bounds at the relevant time. In combination with sensors located elsewhere, such as ball sensors, field sensors and other equipment or uniform sensors, the sensor may provide valuable information for evaluating athletic performance or other uses such as positioning the athlete's head, hands, feet, knees, or chest, relative to other locations. The sensors may be used to assist in tracking the player's movement on television, which enhances the viewing experience of the fans. The uniform or equipment sensors may be used to obtain useful data, such as data pertaining to a player kicking the soccer ball. This data may be used by the athlete and his trainers/coaches as a training aid, by team management to evaluate the player, and by the fans to better understand the player's performance. The uniform and equipment sensors may be used to identify and/or verify an appropriate penalty situation, such as may occur during disallowed movement. The uniform and equipment sensors may be used to monitor the physiology of the athlete, by measuring, for example, heart rate, blood pressure, internal temperature, glucose levels, etc.

B.3. Basketball

As noted above, within one aspect of the invention sports equipment and areas of play are provided with sensors for the game of basketball. Briefly, basketball is a game played by two teams, of five players each, on a rectangular floor. The purpose of each team is to throw an inflated spherical ball into its own basket or goal located at one end of the playing floor, and to prevent the other team from scoring at its basket located at the other end. A basket made from closer than 19 feet 9 inches is worth 2 points. A shot made from outside this area is worth 3 points, and a free throw is worth one point. Basketball is oftentimes identified as the most popular indoor ball game.

Basketball teams consist of professionals, or school age young people, or sometimes just randomly selected people interested in playing the game. The rules may change slightly depending on the players and the environment. For example, a regulation high school game consists of four quarters, 8 minutes in length and a college game consists of 2 20 minute halves.

The basketball court is up to 94 feet/29.7 meters long and 50 feet/15 meters wide. Floor dimensions for players of high school age, are 84 feet by 50 feet. The goals are at each end of the playing floor. Backboards can be either rectangular or fan shaped. The metal ring attached to the backboard is 18 inches in diameter, and is hung 10 feet above the floor. Basketballs for boys' high school teams are about 30 inches in diameter and weigh 20-22 oz., while basketballs for girls' high school teams are about 29 inches in diameter and weigh 8-20 oz.

Figure 19:
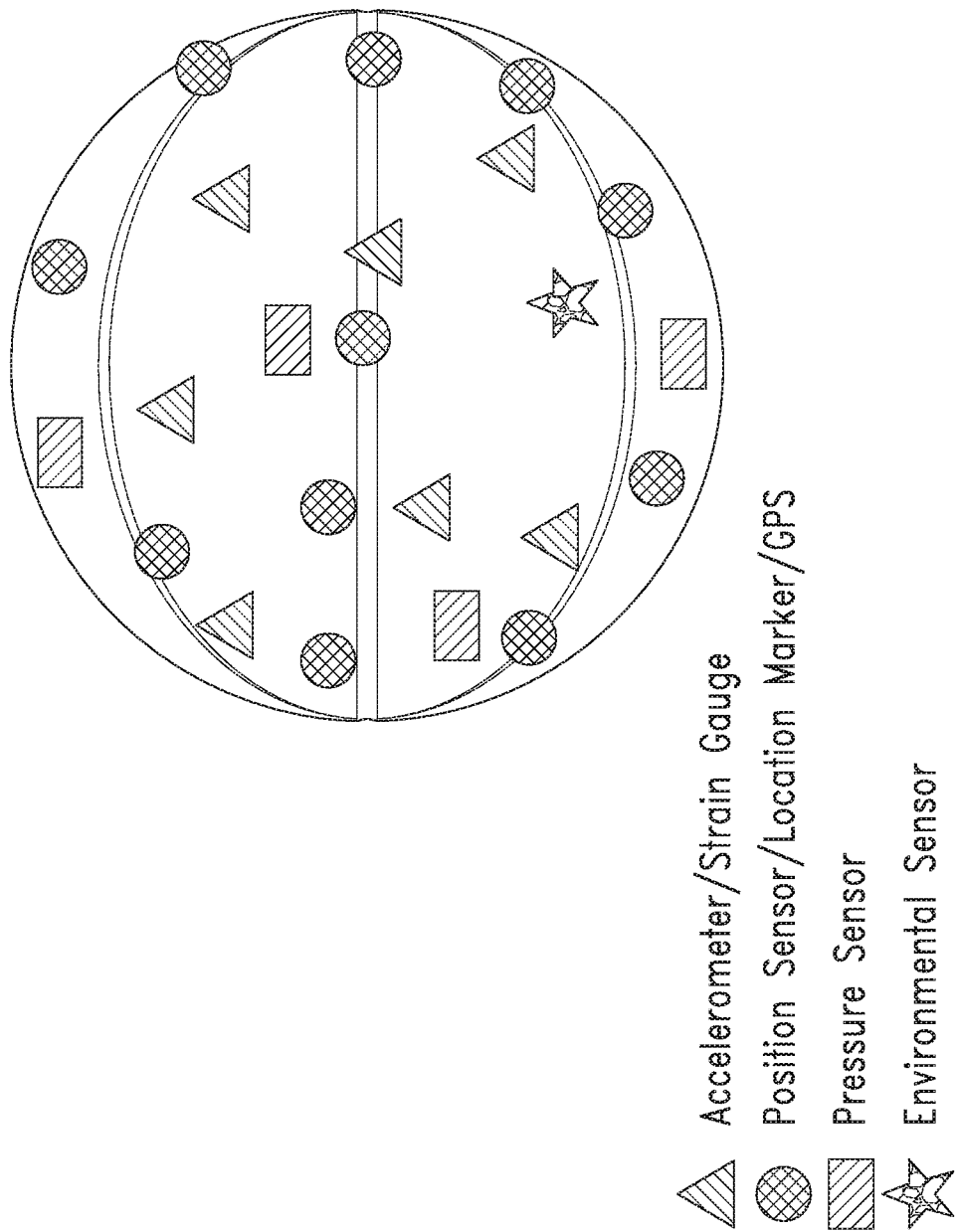
FIG. 19 is an illustration of a variety of sensors on a basketball, according to one embodiment of the invention.

Within one aspect of the invention a basketball is provided with one or more sensors (including for example sensor modules). For example, as shown in FIG. 19, one or more accelerometers, strain gauges, position sensors, location markers, GPS sensors, pressure sensors and environmental sensors may be contained on or within a basketball. The sensors can be distributed through the ball randomly or in an ordered manner. Such sensors can be utilized to track the ball from player to player, and/or across the area of play. The sensors can be utilized, among other things, to: a) determine the location of the ball on the court, to determine whether the ball is in-bounds or out-of-bounds; b) to determine the specific or relative location of the basketball on the court (e.g., to determine whether the ball is behind the 3 point line); c) to determine whether a ball has passed through the hoop or basket of the goal; d) to determine if the ball has hit the backboard; e) to determine a forward pass and/or a backward or lateral pass; f) to determine which player has possession of the ball and/or the occurrence of a pass of the basketball between players; and g) to determine whether the ball is being carried or dribbled.

Within related embodiments one or more environmental sensors can be placed on or within a football. Environmental sensors can be utilized to monitor the temperature, wind speed, humidity, moisture, and other environmental conditions such as air quality (e.g., pollution and/or pollen).

Within other embodiments, one or more pressure sensors can be placed on or within a basketball. Pressure sensors can be utilized to, amongst other things: a) determine contact with the ground; b) to determine possession by a player; c) and to determine impact of a ball against a surface.

Within yet other embodiments one or more accelerometers, gyroscopes and/or strain gauges can be placed on or within a basketball. Such sensors can be utilized to determine, among other things: a) the speed, spin, acceleration and/or velocity of the basketball; b) the direction of the basketball; c) the location of the basketball; d) forces which act upon the basketball (e.g., a throw, pass, or catch of the basketball).

The sensors on the basketball may be used to track the basketball for the benefit of television viewers. The sensors on the basketball may be used to determine whether a defending player touched another player or the ball, in order to more accurately identify a foul. The sensors on a basketball may be used to identify dribbling, and to obtain stats about dribbling. The sensors on a basketball may be used to help determine whether travelling occurred, where this determination may optionally make use of data received from sensors on a basketball shoe. The sensors on a basketball may be used to determine who last had possession of the basketball, or who has current possession of the basketball, which may be important in determining which team should have possession of the basketball after it has gone out of bounds. The sensors on a basketball may be used to determine whether the basketball was kicked, where this determination may optionally make use of data received from sensors on a basketball shoe. The sensors on a basketball may be useful in determining accurate shot marking, for determine player shooting statistics. The sensors on a basketball may be used to determine when the basketball left the possession of a player, which in combination with a game timer may be useful in determining whether a last second shot was made within the appropriate time period. The sensors on a basketball may be used to determine whether the ball was within the cylinder, e.g., did goaltending occur. The sensors on a basketball may be used to determine whether the ball went through the hoop. These and other benefits arise from having sensors on a basketball.

Figure 20:
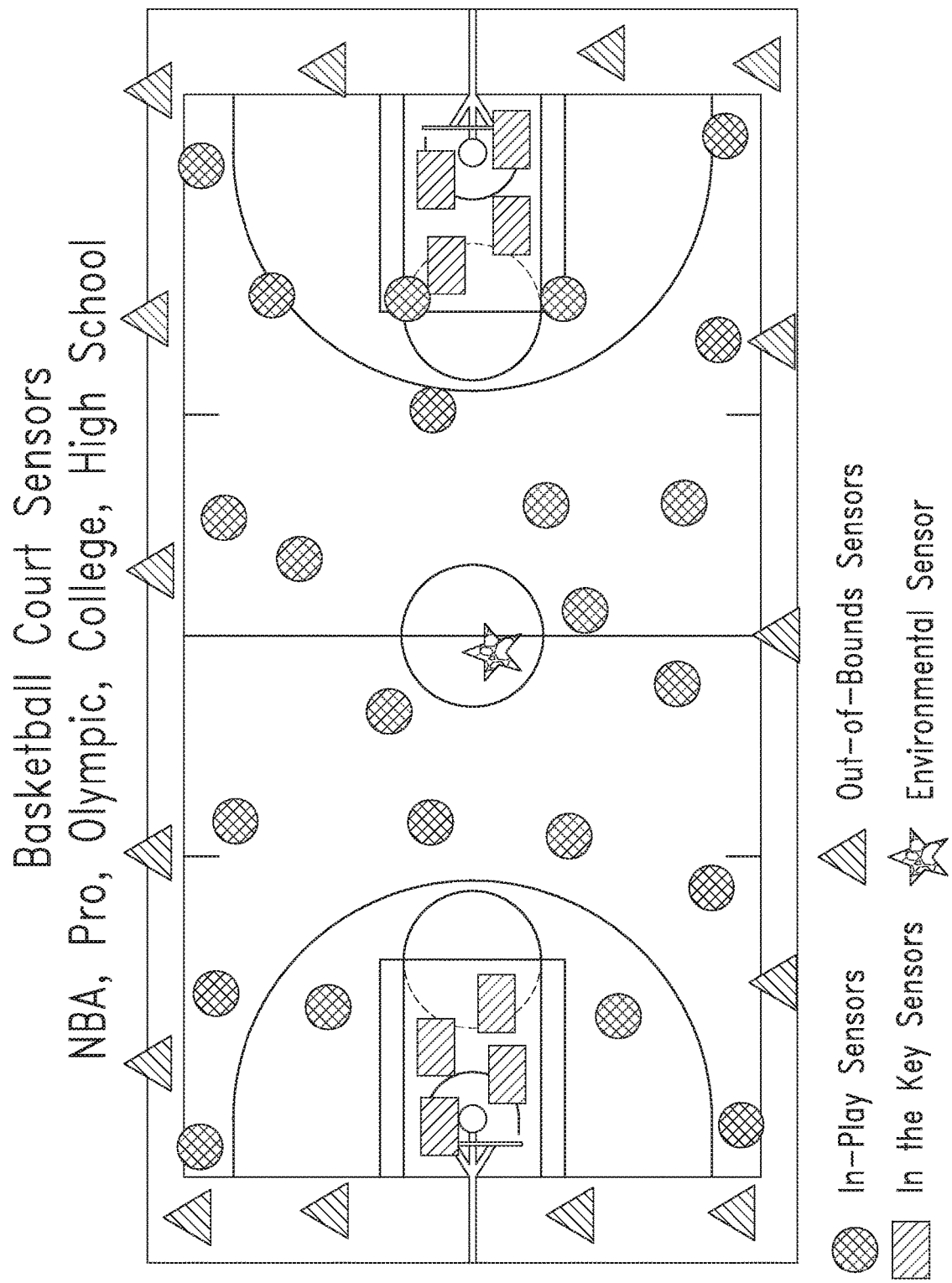
FIG. 20 is an illustration of a variety of sensors on a basketball court, according to one embodiment of the invention.
Figure 21:
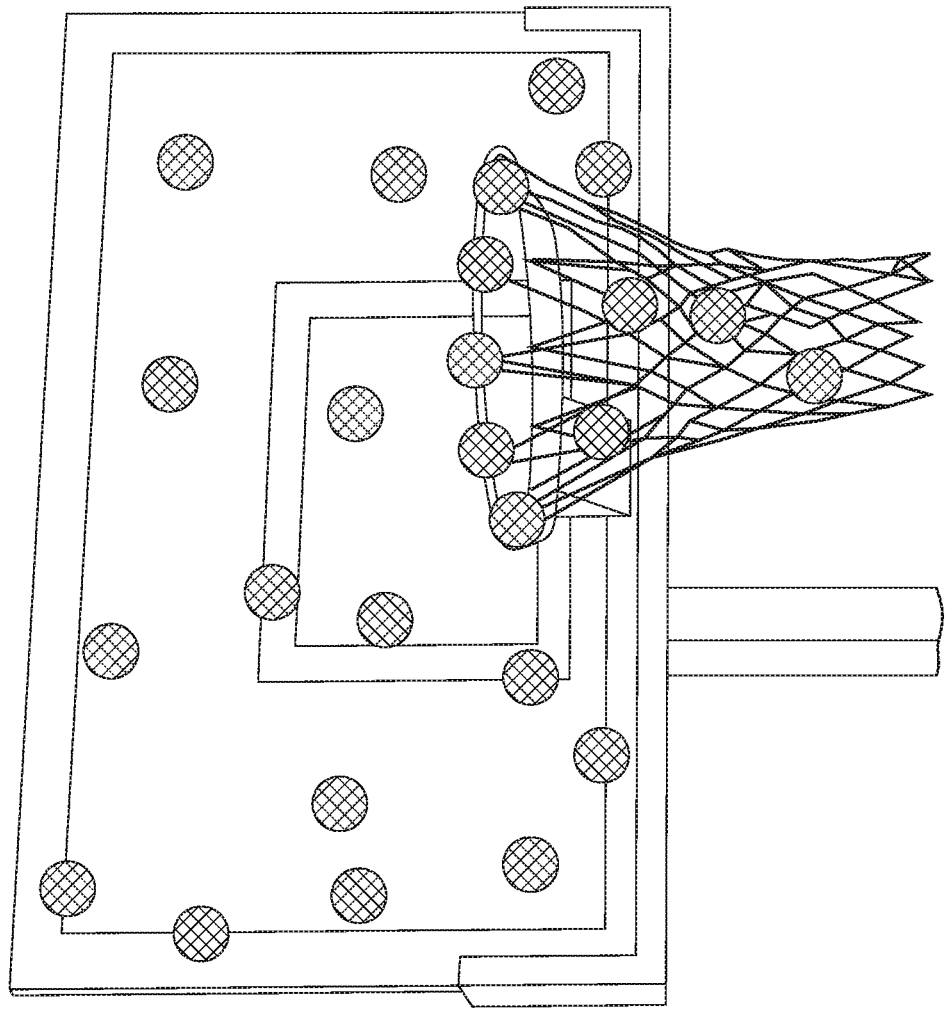
FIG. 21 is an illustration of a variety of sensors on a basketball hoop and backboard, according to one embodiment of the invention.

Within other aspects of the invention the area of play or basketball court (as shown in FIGS. 20 and 21) is set up to have one or more sensors. Sensors can be distributed randomly and/or specifically throughout the court. For example, within one embodiment of the invention position sensors, locations markers, GPS sensors are provided for a basketball court. Such sensors can be utilized to determine in-bounds and out of bounds play. Within certain preferred embodiments of the invention court sensors can be utilized along with basketball sensors and/or equipment sensors (e.g., footwear, and uniform sensors) to determine actual play of the game. For example, by comparing the position or location of a court sensor with one or more ball or equipment sensors one can determine: a) the location of an event on the court; b) accurate position of the ball; c) a player who has control (or loses control) of a ball; d) distances (e.g., behind or in front of the 3 point line); e) for tracking play on the court; f) a forward, backward or lateral pass; g) penalties; h) whether feet are in-bounds or out of bounds; i) whether over and back has occurred; j) whether a player was located within the key for more than 3 seconds; and k) compliance with the 10 second to half court and 5 seconds on defense rules.

Within other embodiments one or more environmental sensors can be utilized to monitor the temperature, wind speed, humidity, moisture, and other environmental conditions such as air quality (e.g., pollution and/or pollen).

FIG. 21 illustrates exemplary locations for exemplary sensors on a basketball hoop, a basketball net and a basketball backboard. Exemplary sensors include position sensors, location sensors, GPS indicators, pressure sensors and accelerometers. Sensor may be distributed throughout one or more of a hoop, net or backboard, or may be clustered in specific locations, for example, at the edges of the backboard.

Within yet other aspects of the invention, one or more sensors are provided on the sportswear (e.g., shoes and uniform) worn by a basketball player. For example, as shown in FIG. 22, one or more sensors such as position sensors, location markers, GPS indicators, accelerometers, gyroscopes, physiology sensors and/or pressure sensors can be included on a basketball jersey, short or shoe. Such sensors can be distributed throughout the sportswear (inside and out) randomly and/or in specific locations, such as on the front or the back of the jersey.

The sportswear sensors may be used in conjunction with other sensors, such as sensors that are located elsewhere on the player's shoes or uniform, sensors that are located on the shoes and/or uniform of another player, sensors that are located on the basketball, and/or sensors that are located on the field of play. Sensors located at various places, and/or sensors located at the same or nearly the same place but which respond to different stimuli or emit different signals, may be used in combination to provide more complete information about a specific time or event.

The information obtained from sportswear sensors, optionally in combination with information obtained from internal or external sensors located elsewhere, may be used for various purposes. For example, information from a jersey sensor may help to better understand an impact received by the player wearing the jersey, where the impact may cause an injury, and where exemplary relevant information is force, impact, rotation, and acceleration. Information from the sensors may be useful to provide a more complete understanding and characterization of the injury or traumatic event, which is valuable for many purposes, including insurance. As other examples, the sensor-derived information may be useful for improved sportswear design, for on-going monitoring of sportswear, for determining the effective lifespan of the sportswear, for determining when sportswear should be replaced, for comparing various pieces of sportswear, for evaluating the degree of protection of a piece of sportswear, optionally in comparison to the protection afforded by a different piece of sportswear.

As another example, which is also shown in FIG. 22, one or more sensors such as position sensors, location markers, GPS indicators, accelerometers, gyroscopes and/or pressure sensors can be included on a basketball shoe. Such sensors can be distributed throughout the shoe (inside and out) randomly and/or in specific locations, such as clustered at the toe of the shoe or on the underside of the shoe.

The shoe sensors may be used in conjunction with other sensors, such as sensors that are located elsewhere on the player's sportswear, sensors that are located on the sportswear of another player, and/or sensors that are located on the basketball and/or the field of play. Sensors located at various places, and/or sensors located at the same or nearly the same place but which respond to different stimuli or emit different signals, may be used in combination to provide more complete information about a specific time or event.

The information obtained from shoe sensors, optionally in combination with information obtained from internal or external sensors located elsewhere, may be used for various purposes. For example, information from shoe sensors may help to better understand an impact received by the shoe, where the impact may cause a foot injury, and where exemplary relevant information is force, impact, rotation, and acceleration. Information about a foot injury may be useful to provide a more complete understanding and characterization of the injury or traumatic event, which is valuable for many purposes, including insurance. As other examples, the sensor-derived information may be useful for improving shoe design, for on-going monitoring of the shoe, for determining the effective lifespan of the shoe, for determining when a shoe should be replaced, for comparing various shoes, and for evaluating the degree of protection of a shoe. The information obtained from sensors on a particular shoe or other piece of sportswear will indicate the repetition of impact, and may provide information that is indicative of subclinical damage. The information from a shoe sensor may be used by trainers to guide the athlete to improved performance. Sensors located at the toe of the shoe may be used to monitor toe location while sensors located on the heel of the shoe may be used to monitor heel location, where this location information may be used, for example, to determine whether the shoe is within or out of bounds of the playing field.

In combination with sensors located elsewhere, such as ball sensors, field sensors and uniform sensors, the shoe sensor may provide valuable information for evaluating athletic performance or other uses such as positioning the athlete relative to other locations. In addition to determining whether the athlete was in-bounds or out-of-bounds at a particular time, the shoe sensor may help determine whether the athlete had one or two feet on the ground at a particular time. The shoe sensor may also provide information that is relevant to accurate court marking such as whether a player threw the ball from behind or in front of the 3 point line, or whether a player went out of bounds at any time, or whether and when coaches and players leave the bench. The shoe sensor can be used to track the player's movements around the court, which may be helpful for a television audience in order to enhance the viewer's experience. The shoe sensor will provide data that is useful in measuring the player's performance, where such information includes speed, acceleration, and power, where this performance information is of interest to athlete, the athlete's trainers and coaches, the team management who is evaluating the player, and the fans who are viewing the performance. The shoe sensor may provide information that is relevant to assessing whether a penalty should be called, such as monitoring movement to evaluate tripping.

One or more sensors such as position sensors, location markers, GPS indicators, accelerometers, gyroscopes and/or pressure sensors can be included on any equipment used by a basketball player, such as protective eyewear, or piece of uniform worn by a basketball player, such as shorts, socks and jerseys. Such sensors can be distributed throughout the equipment or uniform (inside and out) randomly and/or in specific locations.

The equipment and uniform sensors may be used in conjunction with other sensors, such as sensors that are located on the player's other equipment or article of clothing/uniform, sensors that are located on the equipment or uniform of another player, and/or sensors that are located on or around the basketball court. Sensors located at various places, and/or sensors located at the same or nearly the same place but which respond to different stimuli or emit different signals, may be used in combination to provide more complete information about a specific time or event.

The information obtained from equipment and uniform sensors, optionally in combination with information obtained from internal or external sensors located elsewhere, may be used for various purposes. For example, information from equipment and uniform sensors may help to better understand an impact received by the player, where the impact may cause an injury, and where exemplary relevant information is force, impact, rotation, and acceleration. Information about an injury may be useful to provide a more complete understanding and characterization of the injury or traumatic event, which is valuable for many purposes, including insurance. As other examples, the sensor-derived information may be useful for improved equipment or uniform design, for on-going monitoring of equipment or uniform, for determining the effective lifespan of the equipment or uniform, for determining when equipment or piece of uniform should be replaced, for comparing various pieces of equipment or uniforms, for evaluating the degree of protection of a piece of equipment or uniform, optionally in comparison to the protection afforded by a different piece of equipment or uniform. The information obtained from sensors on a particular piece of equipment or uniform article may indicate the repetition of impact, and may provide information that is indicative of subclinical damage. The information from a sensor may be used by trainers to guide the athlete to improved performance.

Sensors located on the uniform or piece of equipment may be used to differentiate between a successful and non-successful action on the part of the athlete. For example, to distinguish whether the player had possession of the ball at a relevant time, or whether the player was in-bounds or out-of-bounds at the relevant time. In combination with sensors located elsewhere, such as basketball sensors, court sensors and other equipment or uniform sensors, the sensor may provide valuable information for evaluating athletic performance or other uses such as positioning the athlete's head, hands, feet, knees, or chest, relative to other locations. For instance, the sensors may assist in differentiating between a situations where the player catches the ball by having his hands under the ball at all relevant times, and when the ball hits the ground and/or bounces before the player grabs onto the ball. The sensors may be used to assist in tracking the player's movement on television, which enhances the viewing experience of the fans. The uniform or equipment sensors may be used to obtain useful data, such as data pertaining to catching, throwing, gripping, etc. of a ball, or running with the ball or without the ball. This data may be used by the athlete and his trainers/coaches as a training aid, by team management to evaluate the player, and by the fans to better understand the player's performance. The uniform and equipment sensors may be used to identify and/or verify an appropriate penalty situation, such as may occur during disallowed movement. The uniform and equipment sensors may be used to monitor the physiology of the athlete, by measuring, for example, heart rate, blood pressure, internal temperature, glucose levels, etc.

B.4. Baseball

As noted above, within one aspect of the invention sports equipment and areas of play are provided with sensors for the game of baseball. Briefly, baseball is played on a diamond-shaped field, with a base at each corner. Each team is made up of nine players. One team bats while the other fields. The pitcher stands on the pitcher's mound, and throws the ball to the batter, who is standing at the home plate. The batter attempts to hit the ball to a part of the field where the fielders cannot reach it. After hitting the ball, the batter then runs to first base, then on to second, third and home, or as many as he can reach before the fielder returns the ball. If the batter reaches all bases and back home, he scores a run. If he reaches a base, and cannot continue as the ball has been returned, he can safely stay at the base and continue his run when the next batter comes to bat. A batter is out if the fielder touches first base with the ball before the batter reaches it, or if the fielder touches the batter with the ball between bases, or if the fielder catches the ball before it lands. The batter is also out if he swings and misses three times, which is called a strike out. When three players are out, the team's innings is over, and the opposing team has a turn at bating. There are nine innings in a game. The team to score the most runs wins the game.

The game is played on a field whose primary boundaries, the foul lines, extend forward from home plate at 45-degree angles. The 90-degree area within the foul lines is referred to as fair territory; the 270-degree area outside them is foul territory. The part of the field enclosed by the bases and several yards beyond them is the infield; the area farther beyond the infield is the outfield. In the middle of the infield is a raised pitcher's mound, with a rectangular rubber plate (the rubber) at its center. The outer boundary of the outfield is typically demarcated by a raised fence, which may be of any material and height (many amateur games are played on unfenced fields). Fair territory between home plate and the outfield boundary is baseball's field of play, though significant events can take place in foul territory, as well.

There are three basic tools of baseball: the ball, the bat, and the glove or mitt. The baseball is about the size of an adult's fist, around 9 inches (23 centimeters) in circumference. It has a rubber or cork center, wound in yarn and covered in white cowhide, with red stitching. The bat is a hitting tool, traditionally made of a single, solid piece of wood. Other materials are now commonly used for nonprofessional games. It is a hard round stick, about 2.5 inches (6.4 centimeters) in diameter at the hitting end, tapering to a narrower handle and culminating in a knob. Bats used by adults are typically around 34 inches (86 centimeters) long, and not longer than 42 inches (106 centimeters). The glove or mitt is a fielding tool, made of padded leather with webbing between the fingers. As an aid in catching and holding onto the ball, it takes various shapes to meet the specific needs of different fielding positions. Protective helmets are also standard equipment for all batters.

Baseball playing fields can vary significantly in size and shape. While the dimensions of the infield are specifically regulated, the only constraint on outfield size and shape for professional teams following the rules of Major League and Minor League Baseball is that fields built or remodeled since Jun. 1, 1958, must have a minimum distance of 325 feet (99 m) from home plate to the fences in left and right field and 400 feet (122 m) to center, however this rule is not uniformly followed. There are no rules at all that address the height of fences or other structures at the edge of the outfield. Similarly, there are no regulations concerning the dimensions of foul territory. Thus a foul fly ball may be entirely out of play in a park with little space between the foul lines and the stands, but a foul out in a park with more expansive foul ground. A fence in foul territory that is close to the outfield line will tend to direct balls that strike it back toward the fielders, while one that is farther away may actually prompt more collisions, as outfielders run full speed to field balls deep in the corner. The surface of the field is also unregulated, and teams are free to decide what areas will be grassed or bare. These physical variations create a distinctive set of playing conditions at each ballpark.

Figure 23:
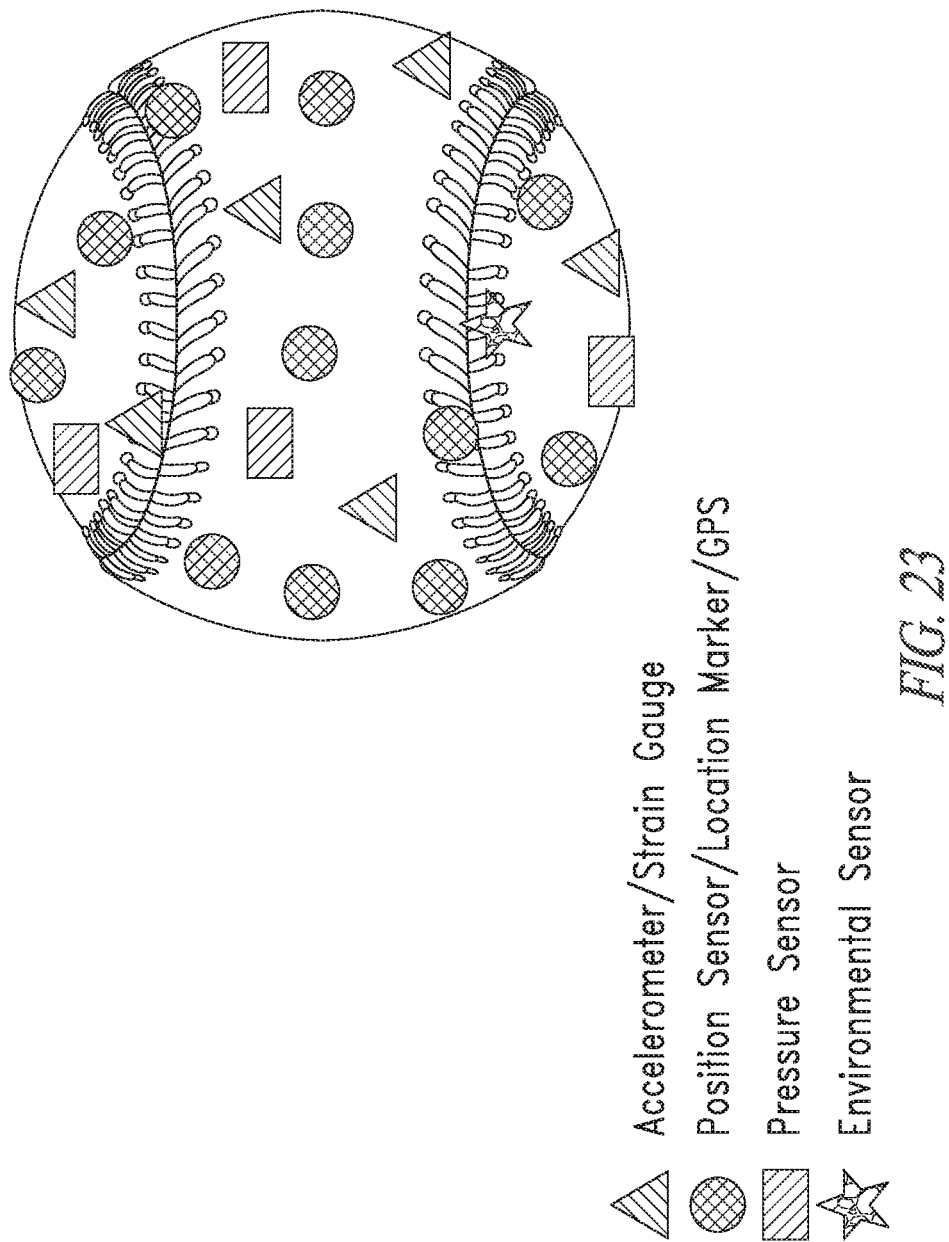
FIG. 23 is an illustration of a variety of sensors on a baseball, according to one embodiment of the invention.

Within one aspect of the invention a baseball is provided with one or more sensors (including for example sensor modules). For example, as shown in FIG. 23 one or more position sensors, location markers and/or GPS sensors may be contained on or within a baseball. In addition, or alternatively, one or more accelerometers and/or strain gauges may be contained on or within a baseball. In addition, or alternatively, one or more pressure sensors may be contained on or within a baseball. In addition, or alternatively, one or more environmental sensors may be contained on or within a baseball. The sensors can be distributed through the ball randomly or in an ordered manner.

Position sensors, location markers and GPS devices can be utilized to track the ball from player to player, and/or across the area of play. The sensors can be utilized, among other things, to: a) determine the location of the ball on the field, such as to determine whether the ball is in-bounds and so is a fair ball, or is out-of-bounds and so is a foul ball; b) to determine the specific or relative location of the ball on the field, for example, to determine the location of the ball relative to the foul pole in order to validate the occurrence of a home run; or to determine the location of the ball relative to the outer fence, again to validate and/or characterize a home run, and to measure the distance traveled by the ball; c) to determine whether a ball has been pitched into the strike zone and therefore qualifies as a strike; d) to determine whether ball has been pitched outside of the strike zone and therefore qualifies as a ball; e) to characterize the throw made by the pitcher, e.g., a slide ball or a fast ball pitch; f) to determine whether the ball has hit the batter; g) to assist in determining whether the batter hit a foul ball or a swinging strike, where this determination may be made in conjunction with data obtained from other sensors, e.g., sensors on the bat; h) to determine whether a runner is safe or out, or has been tagged or not, where this determination may be made in conjunction with the data obtained from other sensors, e.g., sensors on a player's glove, home plate, first, second or third base, or on the baseball uniform; i) to determine whether a player has or has not caught the ball, where this determination may be made in conjunction with the data obtained from other sensors, e.g., sensors located in, on or around the playing field, and glove sensors.

Within related embodiments one or more environmental sensors can be placed on or within a baseball. Environmental sensors can be utilized to monitor the temperature, wind speed, humidity, moisture, and other environmental conditions such as air quality (e.g., pollution and/or pollen).

Within other embodiments, one or more pressure sensors can be placed on or within a baseball. Pressure sensors can be utilized to, amongst other things: a) determine contact with the ground or bat or glove; b) to determine possession by a player; c) and to determine impact of a ball against a surface, e.g., a protective helmet. Pressure sensors may provide information that is used to tell whether a ball has hit the ground prior to being contacted with a glove, so as to distinguish between a catch and no catch situation. Pressure sensors may provide information that is used to tell whether the ball, or a glove holding a ball, has tagged or not tagged a running player. Pressure sensors may provide information that is used to tell whether a foul tip occurred, or whether the ball hit the foul pole. Pressure sensors also provide data that is useful in evaluating player performance.

Within yet other embodiments one or more accelerometers, gyroscopes and/or strain gauges can be placed on or within a baseball. Such sensors can be utilized to determine, among other things: a) the speed, acceleration and/or velocity of the baseball; b) the spin or movement of the baseball after it has been thrown by the pitcher or any other player; c) the location of the baseball, e.g., did it enter the strike zone; d) forces which act upon the baseball, e.g., a throw, hit, or catch of the baseball. Such sensors may be used to measure pitching, throwing and hitting performance of a player, where such information is useful, for example to trainers and coaches seeking to enhance player performance, and to the baseball team management in evaluating and comparing players. Such sensors may provide information that is transmitted to home viewers in order to enhance their viewing experience.

Figure 24:
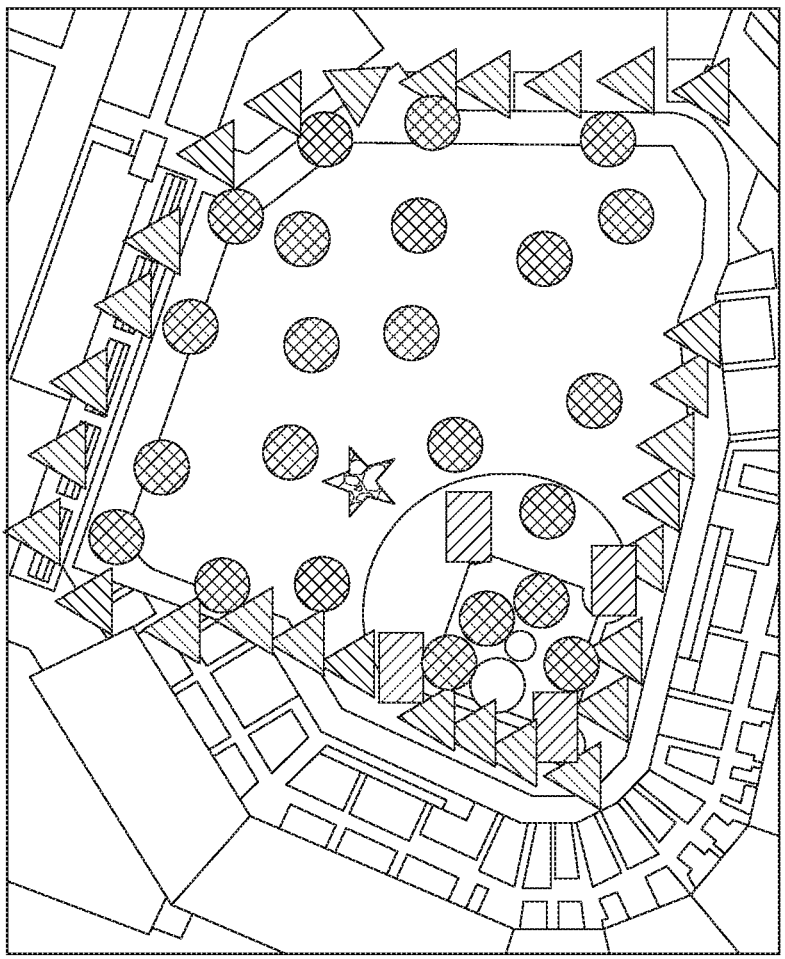
FIG. 24 is an illustration of a variety of sensors on a baseball field, according to one embodiment of the invention.
Figure 25:
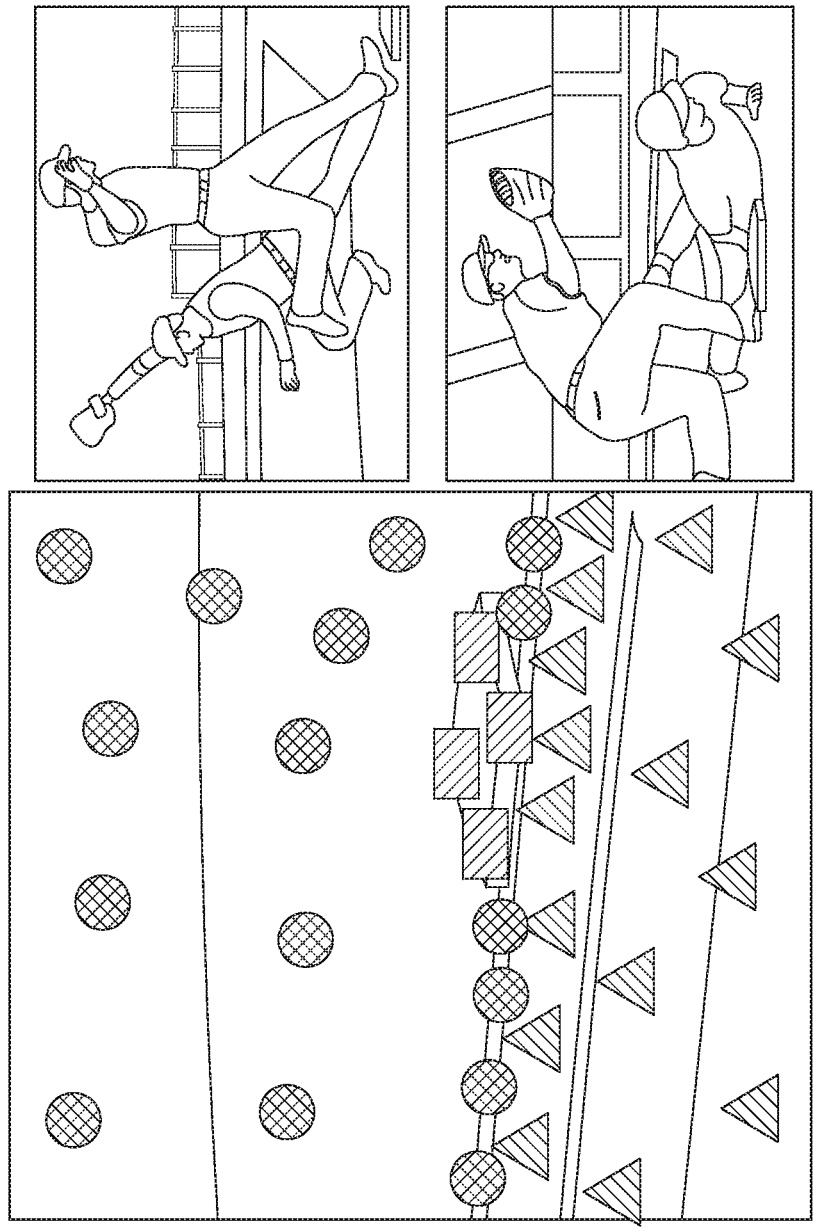
FIG. 25 is an illustration of a variety of sensors on a baseball plate, according to one embodiment of the invention.
Figure 26:
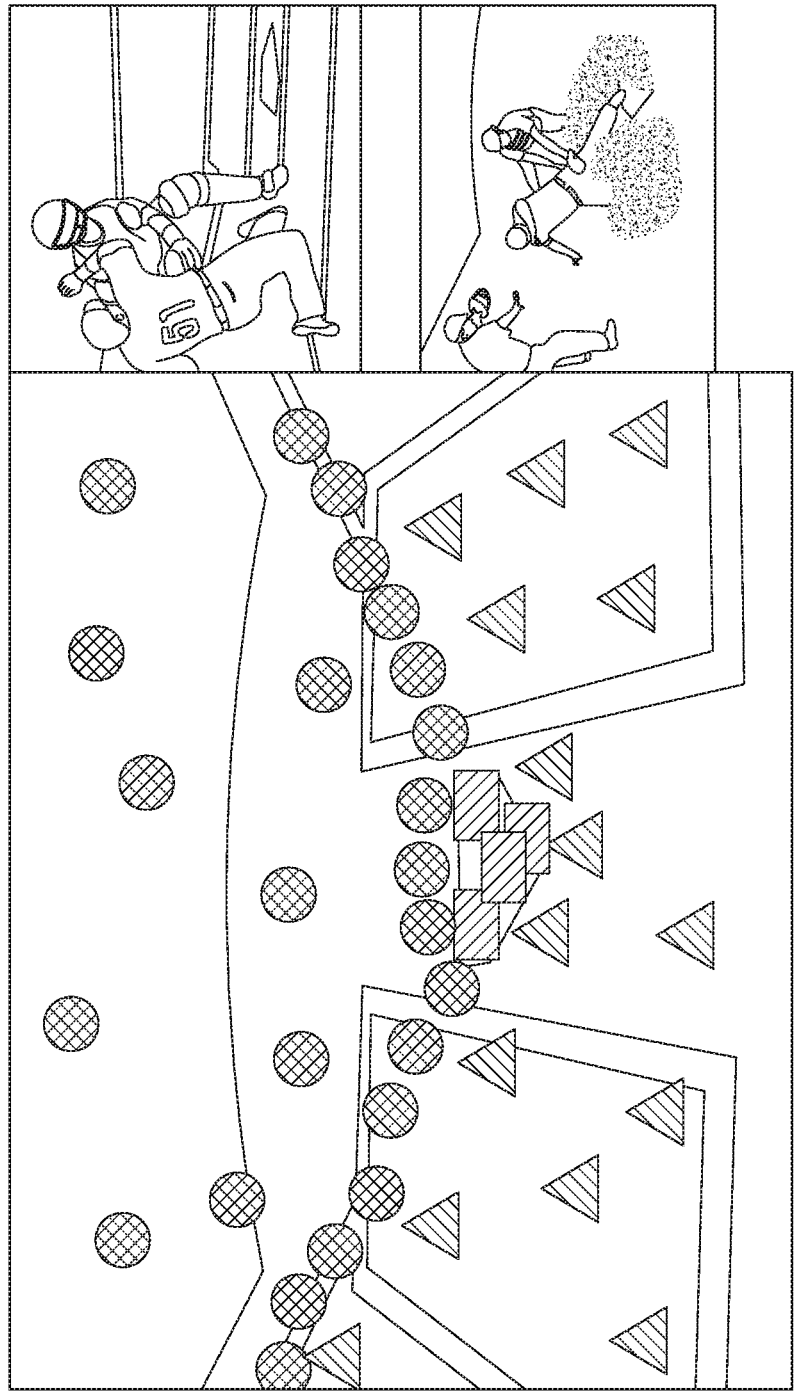
FIG. 26 is an illustration of a variety of sensors on a home plate and batter's box for baseball, according to one embodiment of the invention.

Within other aspects of the invention the area of play or baseball field (as shown in FIGS. 24, 25 and 26) is set up to have one or more sensors. Sensors can be distributed randomly and/or specifically throughout the playing surface, for example, on and around the baseball bases. For example, within one embodiment of the invention position sensors, locations markers, GPS sensors are provided for a baseball field. Such sensors can be utilized to determine in-bounds and out of bounds play. Within certain preferred embodiments of the invention field sensors can be utilized along with equipment sensors (baseball, bat, glove, helmet sensors) and/or uniform sensors (e.g., footwear, and uniform sensors) to determine actual play of the game. For example, by comparing the position or location of a field sensor with one or more ball or equipment sensors one can determine: a) the location of an event on the field; b) accurate position of the ball; c) a player who has control (or loses control) of a ball; and d) distances (e.g., from the point that a baseball is caught by an outfielder to each of the basemen); e) for tracking play on the field.

Position sensors distributed throughout the baseball playing field may interact with and differentiate information received from ball sensors, shoe sensors, uniform sensors and other sensors. For example, these sensors may identify the location of the baseball on the field, optionally in conjunction with information from other sensors, such as glove, uniform and ball sensors; the sensors may be clustered on foul lines or on the foul pole, which in conjunction with information from other sensors, such as ball sensors and foul sensors, may determine whether a ball is a fair ball or a foul ball; the sensors may be located on outfield fences and/or clustered adjacent to the home run line, to facilitate accurate home run calls; the sensors may be used in conjunction with other sensors, such as fielder's glove sensors and ball sensors, to accurate determine whether a catch has or has not occurred; the sensors may assist in tracking the baseball around the field for the benefit of television viewers, which is particularly useful when the ball is obscured from view; the sensors may help determine whether a pitched ball was located within or outside of the batter's box; the sensors may determine where the batted ball is located relative to the baseline; the sensors may help determine whether any interference between players occurred, such as between runners, catchers and fielders; and the sensors may be used to determine whether a player is touching a base or bag at a particular time and relative to other events that are taking place on the field.

Sensors such as position sensors may be located outside the baseball playing field, where these sensors may be referred to as out-of-bound or out-of-play or foul territory sensors. These sensors may be distributed throughout the playing surface in foul territory. These sensors may optionally be used in conjunction with other sensors to evaluate and differentiate events, where other sensors include ball sensors, shoe sensors, and uniform sensors. Foul territory sensors may be used to determine whether the baseball is in play, where this determination may be made in conjunction with information from other sensors, such as glove, uniform and ball sensors. Foul territory sensors may be clustered adjacent to foul lines and/or foul poles to determine whether the ball is in foul territory, and so to make an accurate fair or foul determination. Foul territory sensors may be used to determine the distance traveled by a baseball, such as when a batter hits a baseball out of the park for a home run. Foul territory sensors may be clustered in the batter's box, to help determine whether a player has been hit with a foul ball and whether the player is out-of-play.

Within other embodiments one or more environmental sensors can be utilized to monitor the temperature, wind speed, humidity, moisture, and other environmental conditions such as air quality (e.g., pollution and/or pollen) in the foul territory.

Sensors may be located on and/or around the bases of the baseball field, including one or more of first base, second base, third base and home plate as shown, for example, in FIG. 25. Such sensors may help identify and/or differentiate activities that occur in play or in fair ball territory, or in out-of-play or foul ball territory. Sensors may be located on and/or around home plate and the batter's box, as shown, for example, in FIG. 26. Such sensor may help identify and/or differentiate activities that occur in play or in fair ball territory, or in out-of-play or foul ball territory. Such sensors may include position sensors, location markers, GPS units and pressure sensors. Such sensors may provide information that is used in conjunction with information obtained from other sensors, such as sensors located on the baseball, glove, shoe, or uniform. Such sensors have many uses, including to determine whether a runner is safe or out at home plate, where such a determination may be made in conjunction with information from other sensors, such as glove, shoe, uniform and ball sensors; to determine the timing of a base runner's foot contacting a base, e.g., first base, versus the baseball hitting the fielder's glove; to determine the timing of a base runner's body or uniform touching the base versus a glove or ball touching the base, to identify, e.g., a force play or a tag play; to determine whether and when a fielder's foot is contacting the plate or base, to identify, e.g., a force play; to characterize events taking place at home plate, e.g., whether a tag or no tag of the runner occurred, whether a runner touch home plate or not, and whether a score occurs before the $3^{rd}$ out was recorded, where such determinations may be made in conjunction with information received from other sensors; to determine whether a player left base on time versus leaving earlier, in order to identify, e.g., a sacrifice fly; to determine whether a runner maintained contact with a base throughout a slide; to determine the accuracy of a foul or fair call when, e.g., the baseball hits the bag at the first or third base; and to determine home plate in-play if hit by batted ball.

Within yet other aspects of the invention, one or more sensors are provided on the equipment used by the baseball players. Commonly used equipment includes, in addition to the baseball, a bat and a glove. For example, as shown in FIG. 27, one or more sensors such as position sensors, location markers, GPS indicators, accelerometers, gyroscopes and/or pressure sensors can be included on a baseball bat or baseball glove. Such sensors can be distributed throughout the equipment (inside and out) randomly and/or in specific locations, such as on the handle of the bat or on the webbing of the glove. An equipment sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from equipment sensors, optionally in combination with information obtained from internal or external sensors located elsewhere, may be used for various purposes. For instance, the information from equipment sensors may be used in conjunction with information from ball sensors, field sensors, uniform sensors, etc. to more accurately or completely characterize an event. Those purposes may depend on the location of the sensors on the equipment. For example, looking at the glove, sensors located on the finger and palm areas may be more useful for identifying a caught ball, while sensors located on the back of the glove may be more useful for identifying a tag play. In general, information from glove sensors may help to better understand an impact received by the glove, where the impact may be due to a caught ball or tagging another player, etc. Information from glove sensors may be used to differentiate between a catch and no catch situation, by providing information about whether a bobble occurred or whether the catcher truly had possession of the baseball. Information from glove sensors may be used to identify a tag play, when the information answers the question of whether a player touched an opposing player and at what time. Information from glove sensors may be used to differentiate whether a catch occurred in foul or fair territory. Information from glove sensors may be used to describe the timing of a catch on a force play, in order to determine whether a runner is safe or out. As other examples, which are particularly relevant to bat sensors, the sensor may provide information about bat speed, impact of the bat with a ball or other surface, the power of an impact, the force of the impact. The bat sensor may identify whether the bat was contacted by a baseball, which is important in identifying a foul tip, for example. The bat sensor may be used as a training aid, where the information obtained from the bat sensor is analyzed and used by trainers and coaches to help the baseball player improve performance. The information from a bat sensor may be transmitted to fans in order to provide a more in-depth understanding of the playing events, and thereby lead to enhanced fan enjoyment.

As other examples, the sensor-derived information may be useful for improved baseball equipment design, for on-going monitoring of equipment, for determining the effective lifespan of the equipment, for determining when equipment should be replaced, for comparing various pieces of equipment, for evaluating the degree of protection of a piece of equipment, optionally in comparison to the protection afforded by a different piece of equipment. The information obtained from sensors on a particular helmet or other piece of equipment will indicate the repetition of impact, and may provide information that is indicative of subclinical damage.

Figure 28:
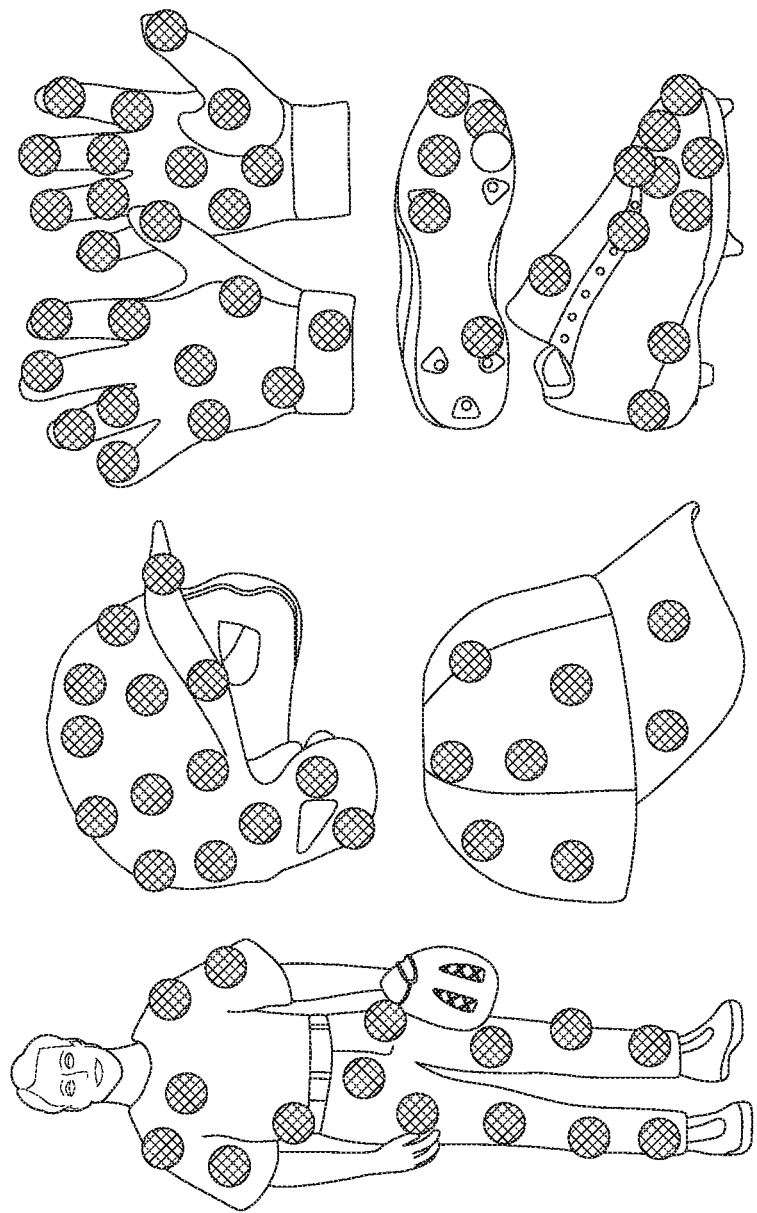
FIG. 28 is an illustration of a variety of sensors on a baseball uniform, helmet, hat, glove and cleat, according to one embodiment of the invention.

As another example, which is shown in FIG. 28, one or more sensors such as position sensors, location markers, GPS indicators, accelerometers, gyroscopes, physiology sensors and/or pressure sensors can be included on equipment (e.g., shoes, protective helmet, gloves, hat, etc.) or uniforms (e.g., shirts, pants, running gloves (as distinguished from gloves used by fielders and basemen to catch a ball), etc.) that are worn by a baseball player. Such sensors can be distributed throughout the equipment or uniforms (inside and out) randomly and/or in specific locations, such as on the cleats of the shoe or clustered at the toe of the shoe.

An equipment or uniform sensor may provide data that is used in conjunction with other data from other sensors, such as sensors that are located on the player's other equipment or article of uniform, sensors that are located on the equipment or uniform of another player, and/or sensors that are located on the baseball and field of play. Sensors located at various places, and/or sensors located at the same or nearly the same place but which respond to different stimuli or emit different signals, may be used in combination to provide more complete information about a specific time or event.

Exemplary running glove sensors include any one or more position sensors, location markers, GPS indicators, pressure sensors and accelerometers. These sensors may be distributed randomly in or on the running glove, and/or at specific locations such as the palm or back of the glove. In one embodiment, the sensors are clustered on the fingers and palm of the glove. The running glove sensors may interact with, and differentiate information received from, other sensors including base sensors, field sensors, uniform sensors, baseball glove sensors and ball sensors. Information from running glove sensors may be used to describe the actions of base runners, e.g., base runners who are engaging in head-first slides. Information from running glove sensors may be used to differentiate between when a player is safe and out, such as if the player contacts the bag prior to a tag being delivered by an opposing player, or if the player contacts the bag prior to the occurrence of a force play. Information from running glove sensors may be used to track the movement of a player on the playing field. Information from running glove sensors may be used to describe and evaluate hand speed when hitting, bat grip, swing trajectory, where such data may be particularly useful for trainers and coaches in training the athlete, and in team management in evaluating an athlete's performance. Information from running glove sensors may be transmitted to the fans in order to provide a more in-depth viewing experience.

Exemplary baseball shoe sensors, which include cleat sensors, include any one or more position sensors, location markers, GPS indicators, pressure sensors, physiology sensors, and accelerometers. These sensors may be distributed randomly in or on the shoe, and/or at specific locations such as the cleats or back of the shoe. In one embodiment, the sensors are clustered on the toe of the shoe. The baseball shoe sensors may interact with, and differentiate information received from, other sensors including base sensors, field sensors, uniform sensors, baseball glove sensors and ball sensors. Information from shoe sensors may be used to describe the actions of base runners, e.g., base runners who are engaging in feet-first slides. Information from shoe sensors may be used to differentiate between when a player is safe and out, such as if the player contacts the bag prior to a tag being delivered by an opposing player, or if the player contacts the bag prior to the occurrence of a force play. Information from shoe sensors may be used to track the movement of a player on the playing field. Information from shoe sensors may be used to confirm contact between the player's shoes and the bags at first, second, third base, or home plate, to confirm that contact was made as a player is running or rounding the bases. Information from shoe sensors may confirm timing on tag-up plays. Information from shoe sensors may be used to describe and evaluate running speed, acceleration and cutting, where such data may be particularly useful for trainers and coaches in training the athlete, and in team management in evaluating an athlete's performance. Information from shoe sensors may be transmitted to the fans in order to provide a more in-depth viewing experience.

Exemplary baseball helmet sensors include any one or more position sensors, location markers, GPS indicators, pressure sensors, physiology sensors and accelerometers. These sensors may be distributed randomly in or on the helmet, and/or at specific locations such as on the ear piece of the helmet. In one embodiment, the sensors are clustered on the ear piece of the helmet. The information obtained from helmet sensors, optionally in combination with information obtained from internal or external sensors located elsewhere, may be used for various purposes. For example, information from helmet sensors may help to better understand an impact received by the helmet, where the impact may cause a head injury, and where exemplary relevant information is force, impact, rotation, and acceleration. Information about a head injury may be useful to provide a more complete understanding and characterization of the injury or traumatic event, which is valuable for many purposes, including insurance. As other examples, the sensor-derived information may be useful for improved helmet design, for on-going monitoring of the helmet, for determining the effective lifespan of the helmet, for determining when a helmet should be replaced, for comparing various helmets, and for evaluating the degree of protection of a helmet. The information obtained from sensors on a particular helmet will indicate the repetition of impact, and may provide information that is indicative of subclinical damage.

The equipment and uniform sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event. The uniform and equipment sensors may be used to monitor the physiology of the athlete, by measuring, for example, heart rate, blood pressure, internal temperature, glucose levels, etc.

B.5. Hockey

As noted above, within one aspect of the invention sports equipment and areas of play are provided with sensors for the game of hockey. Briefly, hockey is a contact sport which is played on ice using skates and sticks. In the United States, Canada, and some European countries, it is known as "hockey" however the term "ice hockey" is used in countries where hockey refers to field hockey. As used herein, hockey refers to ice hockey. The game is played by two teams with six players each, including a goaltender. It is usually played indoors in a hockey rink. The main goal of the game is to score goals by shooting a rubber disc, which is also called the puck, into the opposing team's goal net which is on the other side of the rink. There are three main rules in ice hockey that limit the puck movement: offside, icing, and puck going out of play. A player is offside if he is in the opponent's zone before the puck. Icing is when the defending team shoots the puck down the ice, without touching another player, across two red lines, first one being the red center line and the second being the goal line. The opposing team must touch the puck before the team who iced the puck, or the call will become void. In international rules, the rule is "no touch" icing; meaning the play is called dead once the puck crosses the goal line. The team who ices the puck is not allowed to substitute players during this stoppage of play.

The playing surface is ice. There are five (5) lines on the ice, two (2) goal lines (both at the end of the ice), two (2) blue lines, separating the offensive/defensive zones from the neutral zone, and the center red line. The official size of a hockey rink is 200 ft. long and 85 ft. wide. The rounded corners will have a radius of 28 feet. The rink is surrounded by "boards" made of wood or fiberglass which will be not less than 40" high, and no higher than 48" above the ice surface. The ice and boards are white, except where authorized by the league. Around the entire length of the boards there will be a yellow kick plate. The net is placed in the center of a line 2" wide line sand 13 feet from the back of rink and centered between the side boards. This line extends across the entire width of the rink and up the boards and is commonly known as the goal line. The net is held in place by 8" yellow flexible pegs. If the rink is longer than 200 feet, the goal line may be placed no more than 15 feet from the end boards with prior approval of the league. Two goal posts 48" high and 6 feet apart when measured from the inside and a cross bar made of the same material as the posts extends from the top of one post to the other. A white nylon mesh is attached to the frame of the net so that when the puck is shot into the net, the puck will not come out of the net. Around the base of the net is a white canvas skirt. This skirt has to fasten 6" back from the goal post and cannot prevent the puck from entering the net, and cannot be more than 1" higher than the base plate. The goal posts and cross bars must be painted red, and all other exterior surfaces will be white. The area in front of the goal is an area known as the crease and is demarked by a 2" wide red line. The goal crease also includes the space above the ice surface as defined by the crease up to the height of the goal (4 ft). The area inside the crease is painted light blue and the area inside the goal is painted gloss white.

To play organized hockey, players will need the essential equipment: skates, helmet (with visor or cage), mouth guard, shoulder pads, elbow pads, hockey gloves, hockey pants, athletic supporter (jock), shin pads, hockey socks, jersey, and hockey stick. Goaltenders have their own category of equipment, goalie helmet (cage required), chest and shoulder protectors, athletic supporter (jock), hockey pants, blocker, glove, goalie stick, goalie pads, and goalie skates. For on ice equipment, there are two (2) nets at each end of the ice and pucks.

Figure 29:
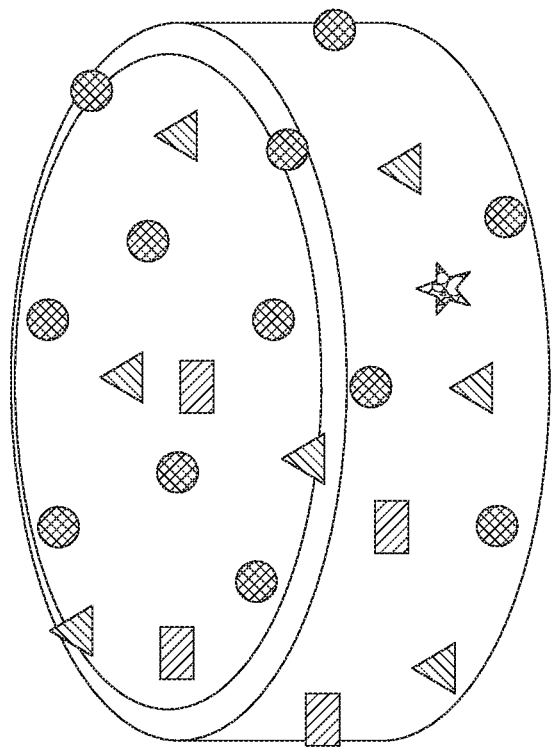
FIG. 29 is an illustration of a variety of sensors on a hockey puck, according to one embodiment of the invention.

Within one aspect of the invention a puck is provided with one or more sensors (including for example sensor modules). For example, as shown in FIG. 29, one or more position sensors, location markers and/or GPS sensors may be contained on or within a puck. In addition, or alternatively, one or more accelerometers and/or strain gauges may be contained on or within a puck. In addition, or alternatively, one or more pressure sensors may be contained on or within a puck. In addition, or alternatively, one or more environmental sensors may be contained on or within a puck. The sensors can be distributed throughout the puck randomly or in an ordered manner.

Position sensors, location markers and GPS devices can be utilized to track the puck from player to player, and/or across the ice rink. The sensors can be utilized, among other things, to: a) determine the location of the puck on the ice, such as to determine whether the puck is over the center line (to identify icing) or past the end line; whether the puck is offside, where this determination may be made in conjunction with information from other sensors such line data sensors and/or skate sensors; whether the puck is above the crossbar, where this determination may be made in conjunction with data from other sensors including stick data in order to determine whether a goal was actually made; whether a hand pass occurred, where this determination may be made in conjunction with data from other sensors such as glove sensors; whether the puck was kicked into the net, where this determination may be made in conjunction with data from other sensors such as skate sensors; and whether the puck is in or not in the crease; b) determine whether the puck is across the goal line, even if the puck cannot be visually seen, where this determination may be made in conjunction with data from other sensors such as net sensors; c) score plays, such as to identify a goal scorer or an assist, where this determination may be made in conjunction with data from other sensors such as stick sensors and sensors specific to particular players; and d) track the puck for the benefit of television audiences.

Within related embodiments one or more environmental sensors can be placed on or within a puck. Environmental sensors can be utilized to monitor the temperature, wind speed, humidity, moisture, and other environmental conditions such as air quality (e.g., pollution and/or pollen).

Within other embodiments, one or more pressure sensors can be placed on or within a puck. Pressure sensors can be utilized to, amongst other things: a) monitor impact, such as occur during shooting and goaltending; and b) obtain data about puck movement.

Within yet other embodiments one or more accelerometers, gyroscopes and/or strain gauges can be placed on or within a puck. Such sensors can be utilized to determine, among other things: a) the speed, acceleration and/or velocity of the puck; b) the direction, location and/or impact of the puck; and c) shooting, passing and stick-handling performance of the players. Such sensors may be used to measure the performance of a player, where such information is useful, for example to trainers and coaches seeking to enhance player performance, and to the hockey team management in evaluating and comparing players. Such sensors may provide information that is transmitted to home viewers in order to enhance their viewing experience.

Figure 30:
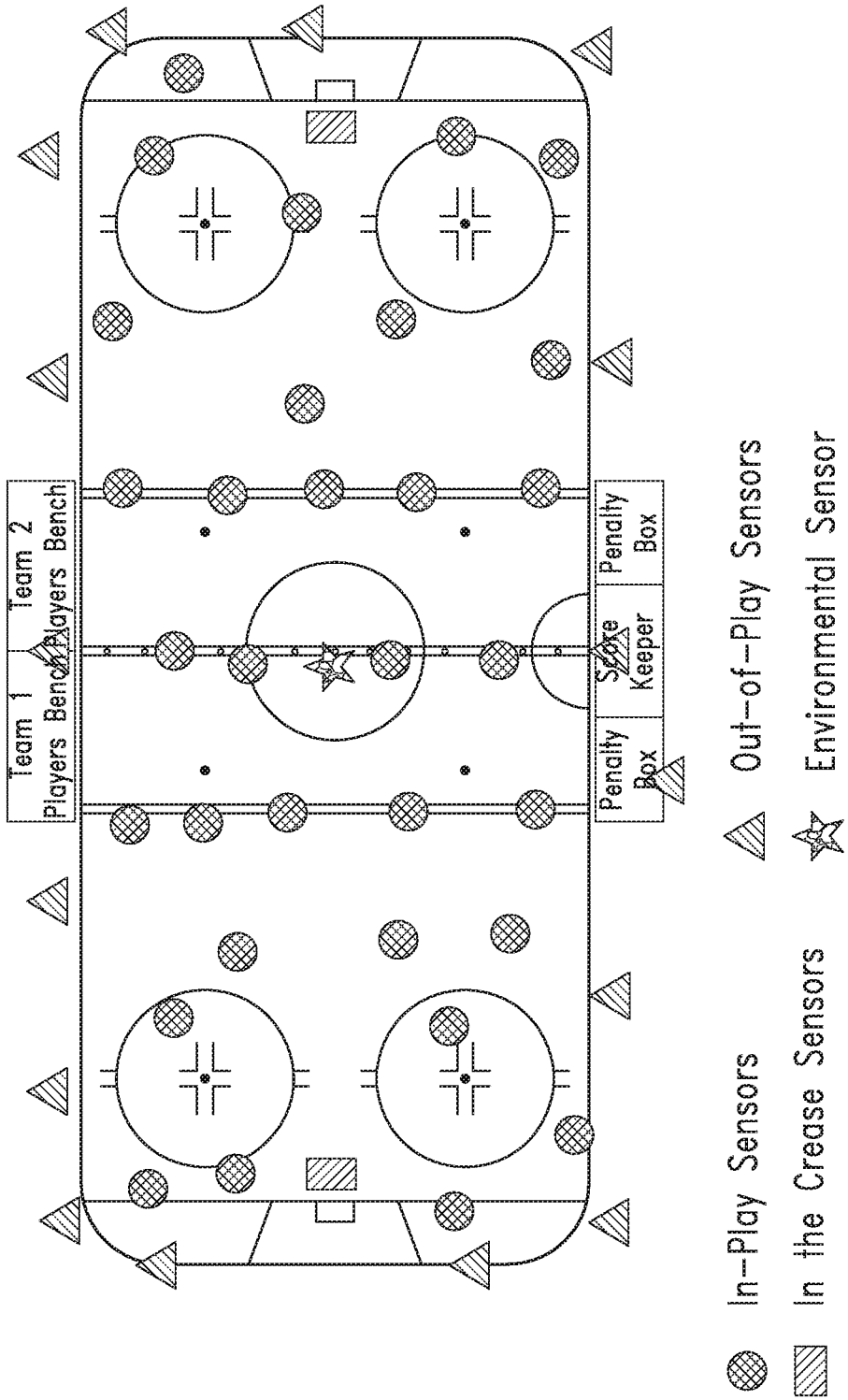
FIG. 30 is an illustration of a variety of sensors on a hockey rink, according to one embodiment of the invention.
Figure 31:
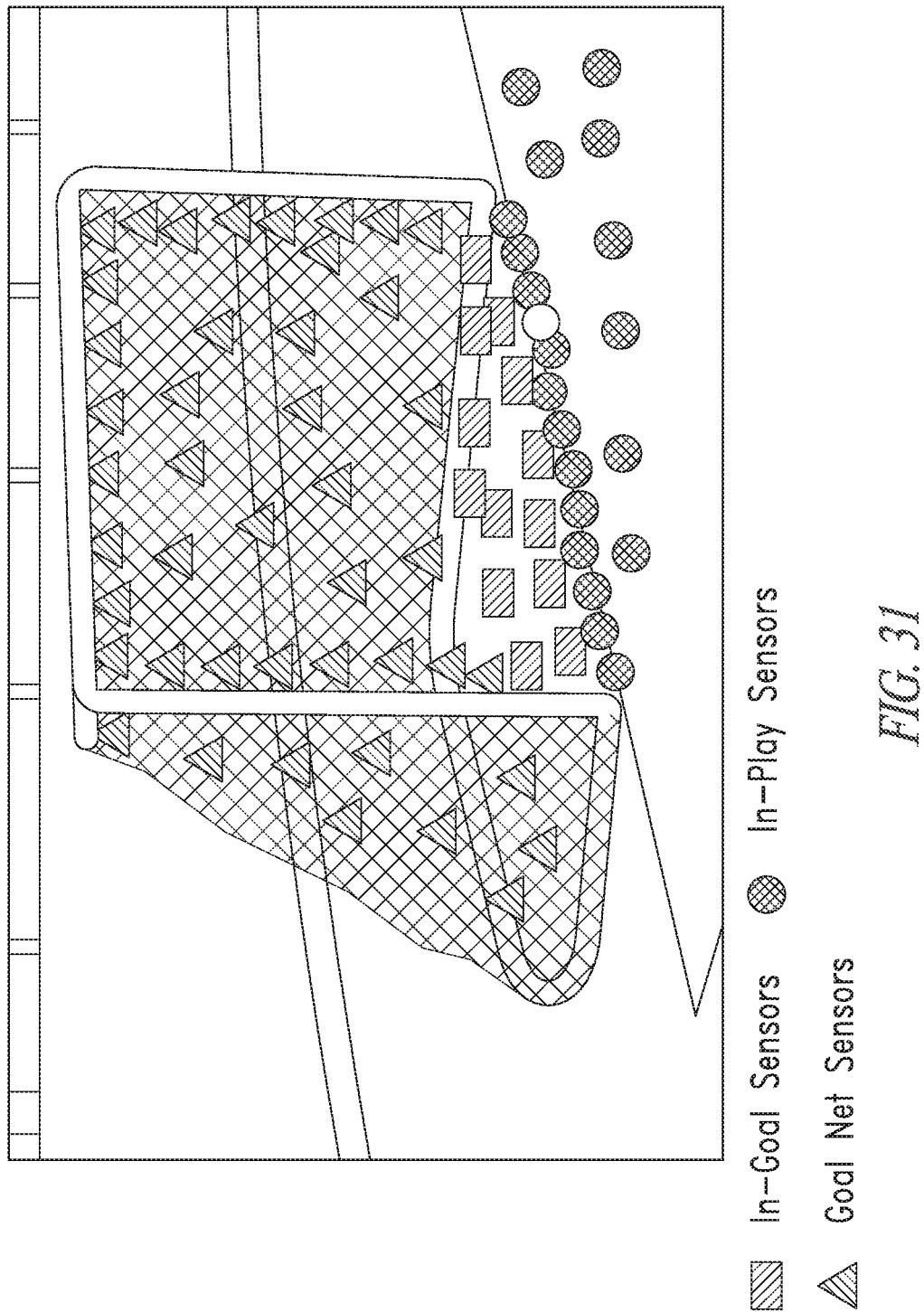
FIG. 31 is an illustration of a variety of sensors on a hockey net and goal line, according to one embodiment of the invention.

Within other aspects of the invention the area of play or hockey rink (as shown in FIGS. 30 and 31) is set up to have one or more sensors. Sensors can be distributed randomly and/or specifically throughout the playing surface, for example, on and around the nets. For example, within one embodiment of the invention, position sensors, locations markers, GPS sensors are provided for a rink. Such sensors can be utilized to monitor in-play and out of play regions, as well as being place in the crease areas. Within certain preferred embodiments of the invention, rink sensors can be utilized along with equipment sensors and/or uniform sensors to determine actual play of the game. For example, by comparing the position or location of a rink sensor with one or more puck or equipment (e.g., skate, stick and uniform) sensors one can determine: a) the location of an event on the rink; b) accurate position of the puck; c) a player who has control (or loses control) of a puck; and d) distances (e.g., from the point that a puck is passed from one player to another); e) for tracking play on the rink.

Position sensors distributed throughout the in-play portion of the rink may interact with and differentiate information received from puck sensors, skate sensors, stick sensors, uniform sensors and other sensors. For example, these sensors may identify the location of the puck on the rink, optionally in conjunction with information from other sensors, such as glove, uniform and puck sensors; the sensors may be clustered adjacent to blue lines, red line, goal line and face-off circles. The rink sensors may be used to make accurate ice calls, such as off side, icing, goalie in the trapezoid, face-off positioning and in the crease. Position sensors in the in-play portion of a rink may be used to accurately distinguish between a goal and no-goal event, particularly when the puck is obscured from view. Position sensors may also be used to track the puck for the benefit of a television audience. Position sensors may provide information that may be used in conjunction with timing information as obtained from a clock, to provide for accurate calling of out-of-play, icing and scoring events. Position sensors may also be used to identify penalty situations, such as when a team has too many men on the ice, when stick fouls such as slacking, hooking and tripping occur, when a player is hit from behind, etc.

Similarly, positions sensors may be located in out-of-play areas of the arena. These out-of-play sensors may be used to capture information that can be used in conjunction with information from other sensors, such as puck sensors. Examples of use include placing a cluster of sensors behind the nets, in the defensive end, in order to, for example, identify when the puck is out of play. Other sensors may additionally or alternatively be placed in the out of play area, including environmental sensors that may monitor conditions such as temperature, humidity, moisture, and ice quality.

Sensors may be located on and/or around the net and goal line. These sensors may be positioned so as to detect in-goal events, in-play events, or contact with the net itself. In goal position sensors, including location markers, GPS indicators and pressure sensors may be distributed throughout the ice surface inside the net, optionally clustered adjacent to the goal line due to the importance of this location in determining accurate scoring. Sensors in this area will primarily interact with puck sensors, although will also interact with other sensors such as skate and stick sensors. Examples of the usefulness of having in goal sensors include being able to determine when the puck breaks the plane of the goal line and tracking the puck for the benefit of the television viewers, particularly when the puck is obscured from view.

Goal net position sensors, including location markers, GPS indicators and pressure sensors may be distributed throughout the goal netting, optionally clustered adjacent to the goal posts. Sensors in this area will primarily interact with puck sensors, although will also interact with other sensors such as skate and stick sensors. Examples of the usefulness of having goal net sensors include being able to determine when the puck breaks the plane of the net and tracking the puck for the benefit of the television viewers, particularly when the puck is obscured from view.

Goal crease position sensors, including location markers, GPS indicators and pressure sensors may be distributed throughout the playing surface in the penalty area, optionally clustered on the goal line. Sensors in this area will primarily interact with puck sensors, although will also interact with other sensors such as skate and stick sensors. Examples of the usefulness of having goal crease sensors include being able to determine whether the puck completely crossed the goal line, and was a player in the crease at a relevant tie, and did goal tender interference occur.

Within yet other aspects of the invention, one or more sensors are provided on the equipment and/or uniform used by the hockey players, as shown in FIGS. 32, 33, 34 and 35. Commonly used player equipment and uniform includes skates, helmet (with visor or cage), mouth guard, shoulder pads, elbow pads, hockey gloves, hockey pants, athletic supporter (jock), shin pads, hockey socks, jersey, and hockey stick. Goaltenders have their own category of equipment, goalie helmet (cage required), chest and shoulder protectors, athletic supporter (jock), hockey pants, blocker, glove, goalie stick, goalie pads, and goalie skates. Any one or more of this equipment or articles of uniform may be fitted with sensors as described herein.

Figure 32:
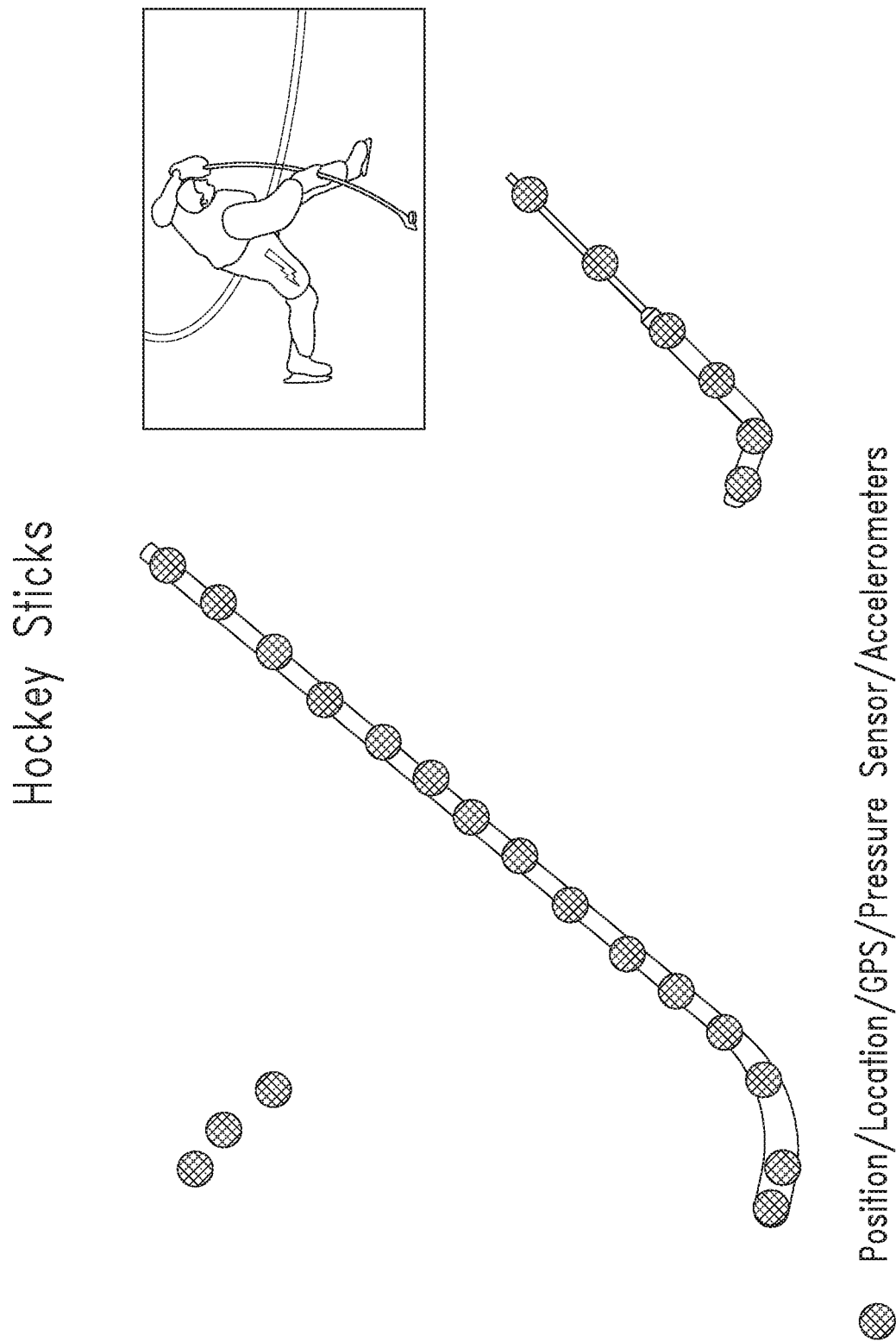
FIG. 32 is an illustration of a variety of sensors on a hockey stick, according to one embodiment of the invention.

For example, a hockey stick may contain sensors. For example, as shown in FIG. 32, one or more sensors such as position sensors, location markers, GPS indicators, accelerometers, gyroscopes and/or pressure sensors can be included on a hockey stick. Such sensors can be distributed throughout the stick (inside and out) randomly and/or in specific locations, such as on the handle of the stick or clustered along the blade. An equipment sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from hockey stick sensors, optionally in combination with information obtained from internal or external sensors located elsewhere, may be used for various purposes. For instance, the information from hockey stick sensors may be used in conjunction with information from puck sensors, ice sensors, uniform sensors, etc. to more accurately or completely characterize an event. Information from stick sensors may be used to identify or call a penalty due to in appropriate use of the stick, for example, a stick foul. Stick fouls include hooking, spearing, slashing, cross-checking, butt ending, tripping and high sticking. The identification of a penalty-earning situation may be achieved by using the data from the stick sensors in conjunction with data from other sensors, such as the equipment and/or uniform sensors from a different player. The information from stick sensors may also be used to characterize the positioning of a player, e.g., whether the player is offside or is icing. The information from stick sensors may also be used to assist in accurate scoring, such as by detecting deflections, and to assist in crediting goals and assists. The information from stick sensors may also be used to identify the occurrence of high stick, i.e., when the stick is above the cross bar. The stick sensor may be used as a training or evaluation aid, where the information obtained from the stick sensor such as stick speed, stick impact, stick power, stick force and stick handling is analyzed and used by trainers and coaches to help the hockey player improve performance. The information from a stick sensor may be transmitted to fans in order to provide a more in-depth understanding of the playing events, and thereby lead to enhanced fan enjoyment. As other examples, the stick sensor-derived information may be useful for improved stick design, for on-going monitoring of hockey sticks, for determining the effective lifespan of a hockey stick, for determining when a hockey stick should be replaced, for comparing various hockey sticks, and for evaluating the effectiveness and accuracy of a hockey stick.

As another example of sensors on hockey equipment, hockey skates may contain sensors. For example, as shown in FIG. 33, one or more sensors such as position sensors, location markers, GPS indicators, accelerometers, gyroscopes and/or pressure sensors can be included on a hockey skate. Such sensors can be distributed throughout the skate (inside and out) randomly and/or in specific locations, such as on the blade of the skate. A skate sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from hockey skate sensors, optionally in combination with information obtained from internal or external sensors located elsewhere, may be used for various purposes. For instance, the information from hockey skate sensors may be used in conjunction with information from puck sensors, ice sensors, uniform sensors, etc. to more accurately or completely characterize an event. Information from skate sensors may be used to identify whether kicking occurred on disputed goals, or whether penalty-earning behavior occurred such as tripping. The skate sensors may identify the location of the skate wearer on the ice, optionally in combination with data from other sensors such as ice, puck and stick sensors. Determining the player's location is necessary in order to identify off side, icing or location in the crease. The skate sensor may be used as a training or evaluation aid, where information obtained from the skate sensor includes, for example, speed, acceleration, cutting and power. This information may be analyzed and used by trainers and coaches to help the hockey player improve performance. The information from a skate sensor may be transmitted to fans in order to provide a more in-depth understanding of the playing events, and thereby lead to enhanced fan enjoyment. As other examples, the skate sensor-derived information may be useful for improved skate design, for on-going monitoring of hockey skates, for determining the effective lifespan of a hockey skate, for determining when a hockey skate should be replaced, for comparing various hockey skates, and for evaluating the effectiveness of a hockey skate.

As a further example of sensors on hockey equipment, hockey helmets may contain sensors. For example, as shown in FIG. 34, one or more sensors such as position sensors, location markers, GPS indicators, accelerometers, gyroscopes and/or pressure sensors can be included on a hockey helmet. Such sensors can be distributed throughout the helmet (inside and out) randomly and/or in specific locations, such as on the faceguard or visor of the helmet, or the mask of the helmet worn by the goalie. A helmet sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from hockey helmet sensors, optionally in combination with information obtained from internal or external sensors located elsewhere, may be used for various purposes. For instance, the information from hockey helmet sensors may be used in conjunction with information from puck sensors, ice sensors, uniform sensors, etc. to more accurately or completely characterize an event. Information from helmet sensors may be used to identify whether there was an impact with the player's head, and the extent of that impact. For example, the sensor may monitor the force of the impact and/or may be used in combination with external or internal sensors to establish and quantify subclinical damage to the player. This information may be needed or at least useful to determine insurance applicability and amounts. The helmet sensor may be used as an evaluation aid, to monitor the cumulative trauma to a player. As other examples, the helmet sensor-derived information may be useful for improved helmet design, for on-going monitoring of hockey helmets, for determining the effective lifespan of a hockey helmet, for determining when a hockey helmet should be replaced, for comparing various hockey helmets, and for evaluating the effectiveness of a hockey helmet.

As a final example of sensors on hockey wearable equipment or uniforms, any piece of a hockey uniform or wearable equipment may contain sensors, such as the shoulder pads, gloves, elbow pads, pants, shin pads or jersey. For example, as shown in FIG. 35, one or more sensors such as position sensors, location markers, GPS indicators, accelerometers, gyroscopes, pressure sensors and/or physiology sensors can be included on a hockey uniform article. Such sensors can be distributed throughout the equipment or uniform (inside and out) randomly and/or in specific locations. A uniform sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from hockey uniform or wearable equipment sensors, optionally in combination with information obtained from internal or external sensors located elsewhere, may be used for various purposes. For instance, the information from hockey uniform or wearable equipment sensors may be used in conjunction with information from puck sensors, ice sensors, other uniform sensors, etc. to more accurately or completely characterize an event. An exemplary event is a sports injury, where the sensors may provide information about, for example, the force, impact, rotation and/or acceleration of a puck or stick or other item that was involved in the impact. The sensors on a hockey uniform or wearable equipment may be used to determine the location of a player on the ice; to help track scoring by, e.g., identifying deflections; to track a player's movements for the benefit of a television audience; to obtain sports data such as speed, acceleration, cutting and power, to be used in the training or evaluation of a player; to monitor hitting between players such as the force of an impact and the resulting injury(s); and to identify penalty-incurring situations such as elbowing, hits to the head, charging, kneeing, etc. As other examples, the uniform or wearable equipment sensor-derived information may be useful for improved item design, for on-going monitoring of the item, for determining the effective lifespan of an item, for determining when an item should be replaced, for comparing various items, and for evaluating the effectiveness of an item.

The wearable equipment and uniform sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event. The uniform and wearable equipment sensors may be used to monitor the physiology of the athlete, by measuring, for example, heart rate, blood pressure, internal temperature, glucose levels, etc.

The sensors as described herein may be used in monitoring other goal sports, in a manner similar to the use of the sensors to monitor hockey as described above. For example, sensors may be used to monitor the sports of field hockey, water polo, lacrosse and European handball, to name a few.

B.6. Tennis

As noted above, within one aspect of the invention sports equipment and areas of play are provided with sensors for racket sports. Exemplary racket sports include tennis, table tennis, lawn tennis, badminton, squash, racquetball and halai. The use of sensors in playing tennis will be described as exemplary of the use of sensors in the playing of any racket sport.

Briefly, tennis is played either as singles, with two opponents, or as doubles, with two people forming a team in opposition to another two person team, all four players playing at any one time. Matches consist of three sets of six games. A set is completed when a player or team has won six games and leads an opponent by two games. Sets reaching six games apiece will play a 7 out-of-12 points tiebreaker.

The playing court is a rectangle 78 feet (23.77 m) long and 27 feet (8.23 m) wide. It is divided across the middle by a net suspended from a cord or metal cable, the ends of which shall be attached to, or pass over, the tops of two posts. The playing surface may be grass or clay or a synthetic rubber-like material.

Equipment includes a tennis racket, where the components of a tennis racquet include a handle, known as the grip, connected to a neck which joins a roughly elliptical frame that holds a matrix of tightly pulled strings. Under modern rules of tennis, the racquets must adhere to the following guidelines: the hitting area, composed of the strings, must be flat and generally uniform, and the frame of the hitting area may not be more than 29 inches in length and 12.5 inches in width. Equipment also includes tennis balls. The International Tennis Federation (ITF) defines the official diameter as 65.41-68.58 mm (2.575-2.700 inches). Balls must weigh between 56.0 and 59.4 grams (1.975-2.095 ounces).

Figure 36:
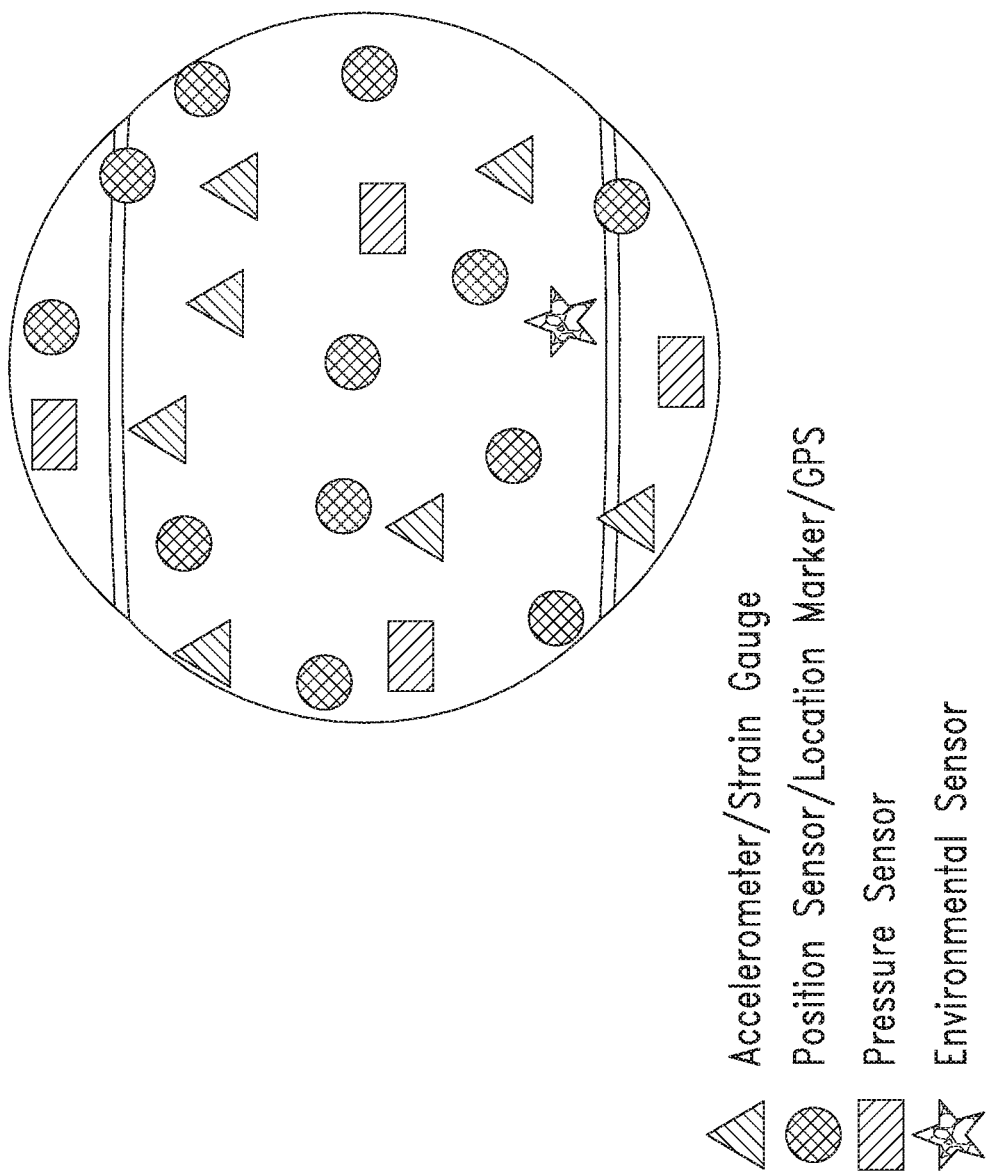
FIG. 36 is an illustration of a variety of sensors on a tennis ball, according to one embodiment of the invention.

Within one aspect of the invention, and as shown in FIG. 36, a tennis ball is provided with one or more sensors (including for example sensor modules). For example, one or more position sensors, location markers and/or GPS sensors may be contained on or within a tennis ball. In addition, or alternatively, one or more accelerometers and/or strain gauges may be contained on or within a tennis ball. In addition, or alternatively, one or more pressure sensors may be contained on or within a tennis ball. In addition, or alternatively, one or more environmental sensors may be contained on or within a tennis ball. The sensors can be distributed throughout the tennis ball randomly or in an ordered manner.

Position sensors, location markers and GPS devices can be utilized to track the tennis ball as it travels from player to player, and/or across the tennis court. The sensors can be utilized, among other things, to: a) determine the location of the tennis ball on or off the court, such as to determine whether the ball has crossed over the center line or beyond the court boundaries; b) whether the ball hits the net on service; c) the speed, spin, and impact of the ball, where this information is of interest to both players, coaches and fans; and d) tracking the ball for the benefit of the television audience.

Within related embodiments one or more environmental sensors can be placed on or within a tennis ball. Environmental sensors can be utilized to monitor the temperature, wind speed, humidity, moisture, and other environmental conditions such as air quality (e.g., pollution and/or pollen).

Within other embodiments, one or more pressure sensors can be placed on or within a tennis ball. Pressure sensors can be utilized to, amongst other things: a) monitor impact, such as occur when the ball hits the racket or the ground; and b) obtain data about tennis ball movement.

Within yet other embodiments one or more accelerometers, gyroscopes and/or strain gauges can be placed on or within a tennis ball. Such sensors can be utilized to determine, among other things: a) the speed, acceleration, spin and/or velocity of the tennis ball; b) the direction, location and/or impact of the tennis ball; and c) measuring serving and ground strokes. Such sensors may be used to measure the performance of a player, where such information is useful, for example to trainers and coaches seeking to enhance player performance, and to the fans in evaluating and comparing players. Such sensors may provide information that is transmitted to home viewers in order to enhance their viewing experience.

Figure 37:
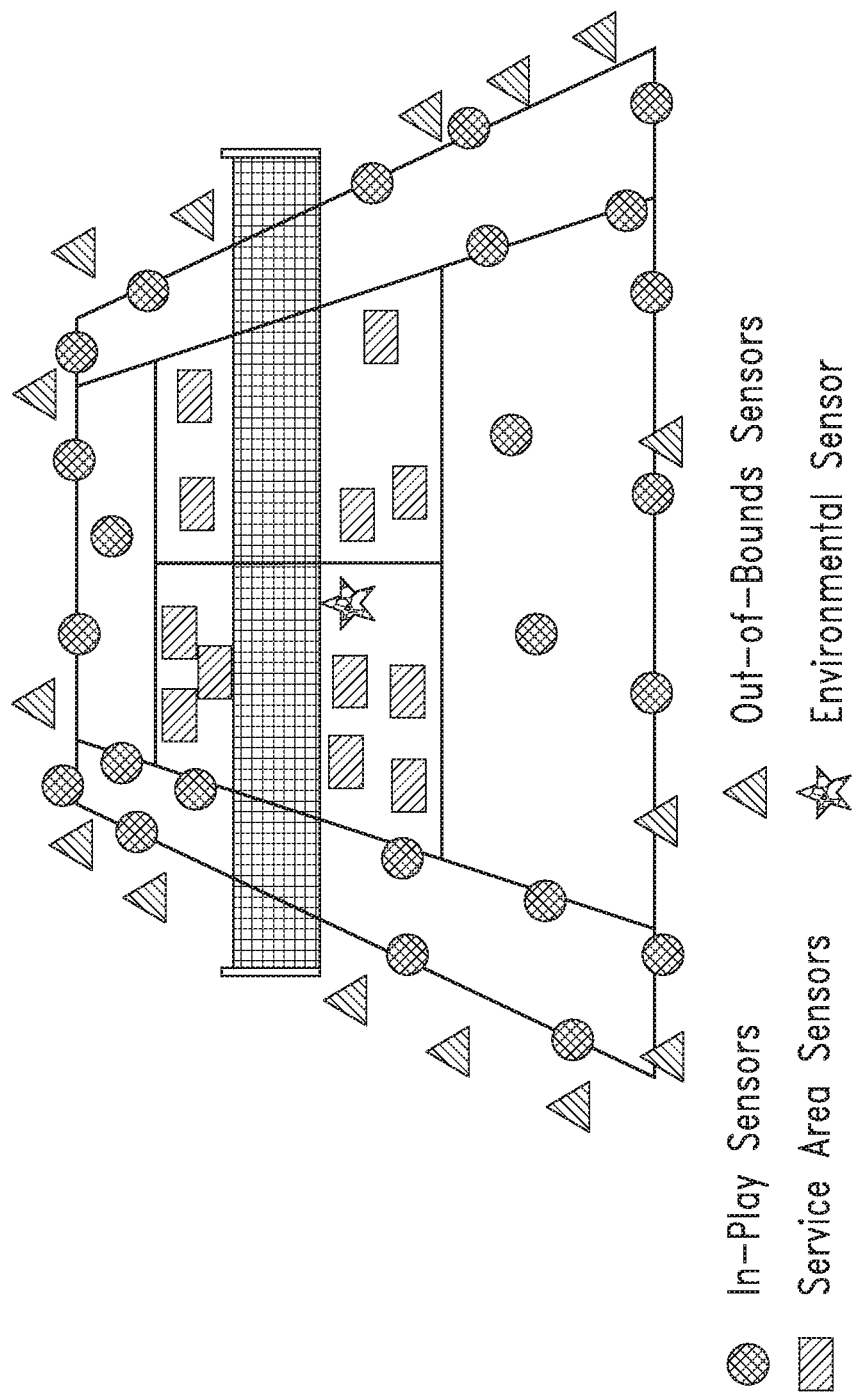
FIG. 37 is an illustration of a variety of sensors on a tennis court, according to one embodiment of the invention.

Within other aspects of the invention, a tennis court (as shown in FIGS. 37 and 39) is set up to have one or more sensors. Sensors can be distributed randomly and/or specifically throughout the playing surface, for example, on and around the net or the court boundaries. For example, within one embodiment of the invention, position sensors, locations markers, GPS sensors are provided for a court. Such sensors can be utilized to monitor in-play and out of play regions. Within certain preferred embodiments of the invention, court sensors can be utilized along with equipment sensors and/or uniform sensors to determine actual play of the game. For example, by comparing the position or location of a court sensor with one or more tennis ball or equipment (e.g., racket) sensors one can determine: a) the location of an event on the court; b) accurate position of the tennis ball; c) a player who has control of a ball; and d) distances that the ball travels between being hit; and e) for tracking play on the court.

Position sensors distributed throughout the in-play portion of the court may interact with and differentiate information received from ball sensors, racket sensors, uniform sensors and other sensors. For example, these sensors may identify the location of the ball in the court, optionally in conjunction with information from other sensors, such as racket sensors; and the sensors may be clustered adjacent to the net or court lines. The court sensors may be used to make accurate calls, such as whether the ball hits the court in-bounds or out-of-bounds. Position sensors may detect whether the ball hits the ground twice before contacting a racket. Position sensors, optionally in combination with other sensors such as shoe sensors, may detect foot fault on service. Position sensors may also be used to track the ball for the benefit of a television audience.

Similarly, positions sensors may be located in out-of-play areas of the court. These out-of-play sensors may be used to capture information that can be used in conjunction with information from other sensors, such as tennis ball sensors. The out-of-play sensors may be used to detect and determine accurate ball placement in the event of a disputed call. Other sensors may additionally or alternatively be placed in the out of play area, including environmental sensors that may monitor conditions such as temperature, humidity, moisture, and air quality (pollution, pollen, etc.).

Yet another location for position sensors including location markers, GPS indicators, and pressure sensors is as service area sensors, which may be distributed throughout the playing surface in the service receiving area. These position sensors may be interact with other sensors, such as tennis ball sensors. These position sensors may be used to determine whether service was in or out. In one embodiment, position sensors and/or pressure sensors are clustered on service lines to be able to accurately determine whether the ball falls on those lines. Service area sensors may also be used to track the location of the tennis ball for the benefit of television viewers.

As shown in FIG. 39, sensors may be located on the net, e.g., on the top or tape of the net. The sensors may be distributed throughout the tennis net. Exemplary sensors include position sensors, location markers, GPS indicators, pressure sensors and accelerometers. A net sensor may be used in conjunction with other sensors, such as sensors that are located on the player's equipment, sensors that are located on the equipment of another player, and/or sensors that are located on the court. Sensors located at various places, and/or sensors located at the same or nearly the same place but which respond to different stimuli or emit different signals, may be used in combination to provide more complete information about a specific time or event. Net sensor may provide information about contact with the tennis ball, such as speed and force of the ball hitting the net. The net sensor may also indicate whether the racket has crossed over the net, where this determination may be made in conjunction with other sensors such as racket sensors and court sensors. The net sensors may be used to assist in tracking the ball, especially for television viewers, and particularly when the ball is obscured from view.

Within yet other aspects of the invention, one or more sensors are provided on the equipment and/or uniform used by the players. For example, sensors may be located on the tennis racket. As shown in FIG. 38, one or more sensors such as position sensors, location markers, GPS indicators, accelerometers, gyroscopes and/or pressure sensors can be included on a tennis racket. Such sensors can be distributed throughout the racket (inside and out) randomly and/or in specific locations, such as on the handle of the racket or clustered along the strings. A tennis racket sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from tennis racket sensors, optionally in combination with information obtained from internal or external sensors located elsewhere, may be used for various purposes. For instance, the information from tennis racket sensors may be used in conjunction with information from tennis ball sensors, court sensors, uniform sensors, etc. to more accurately or completely characterize an event. The racket sensor may be used to monitor player technique, such as evaluating ground strokes, service, racket path and speed. The racket sensor may be used as a training or evaluation aid, where the information obtained from the racket sensor such as racket speed, racket impact, racket power, racket force and racket handling is analyzed and used by trainers and coaches to help the tennis player improve performance. The information from a racket sensor may be transmitted to fans in order to provide a more in-depth understanding of the playing events, and thereby lead to enhanced fan enjoyment. As other examples, the racket sensor-derived information may be useful for improved racket design, for on-going monitoring of tennis rackets, for determining the effective lifespan of a tennis racket, for determining when a tennis racket should be replaced, for comparing various tennis rackets, and for evaluating the effectiveness and accuracy of a tennis racket.

Figure 40:
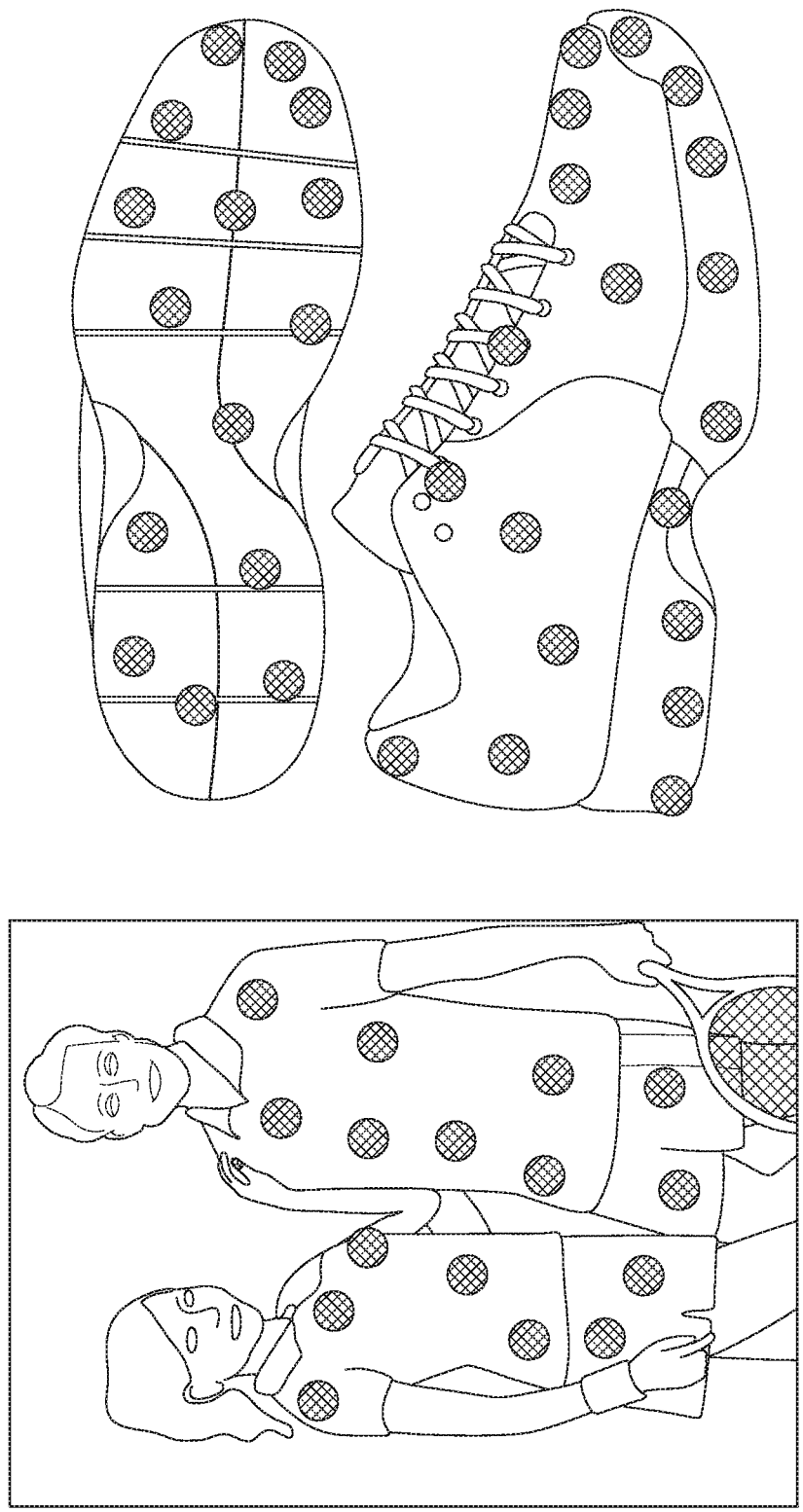
FIG. 40 is an illustration of a variety of sensors on tennis clothing and shoes, according to one embodiment of the invention.

Any piece of a tennis uniform or clothing or wearable equipment such as eye protection may contain sensors. As an example, which is shown in FIG. 40, one or more sensors such as position sensors, location markers, GPS indicators, accelerometers, gyroscopes and/or pressure sensors can be included on a tennis shoe. Such sensors can be distributed throughout the shoe (inside and out) randomly and/or in specific locations, such as on the toe portion of the shoe or clustered at the heel of the shoe. The tennis shoe sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from shoe sensors, optionally in combination with information obtained from internal or external sensors located elsewhere, may be used for various purposes. For example, shoe sensor information may indicate whether the feet of a player or in-bounds or out-of-bounds during service. As other examples, the sensor-derived information may be useful for improved shoe design, for on-going monitoring of shoes, for determining the effective lifespan of the shoe, for determining when a shoe should be replaced, and for comparing various shoes. The information from a shoe sensor may be used by trainers to guide the athlete to improved performance. Shoe sensors may detect the number and length of steps taken by an athlete during play, the height above the ground that an athlete achieves during play, and the extent to which an athlete lands on one or two feet and the extent to which a foot comes down more on the heel or toe. All of this information may be useful to coaches and trainers as well as the athlete themselves.

In combination with sensors located elsewhere, such as ball sensors, court sensors and uniform sensors, the shoe sensor may provide valuable information for evaluating athletic performance or other uses such as positioning the athlete relative to other locations. In addition to determining whether the athlete was in-bounds or out-of-bounds at a particular time, the shoe sensor may help determine whether the athlete had one or two feet on the ground at a particular time, The shoe sensor will provide data that is useful in measuring the player's performance, where such information includes speed, acceleration, cutting, and power, where this performance information is of interest to athlete, the athlete's trainers and coaches.

As another example of a piece of tennis uniform or clothing or wearable equipment such as eye protection containing sensor, and as shown for example in FIG. 40, one or more sensors such as position sensors, location markers, GPS indicators, accelerometers, gyroscopes, pressure sensors and/or physiology sensors can be included on a tennis uniform article. Such sensors can be distributed throughout the equipment or uniform (inside and out) randomly and/or in specific locations. A uniform sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from tennis uniform or wearable equipment sensors, optionally in combination with information obtained from internal or external sensors located elsewhere, may be used for various purposes. For instance, the information from tennis uniform or wearable equipment sensors may be used in conjunction with information from tennis ball sensors, court sensors, other uniform sensors, etc. to more accurately or completely characterize an event. An exemplary event is a sports injury, where the sensors may provide information about, for example, the force, impact, rotation and/or acceleration of a tennis ball or other item that was involved in the impact. The sensors on a tennis uniform or wearable equipment may be used to determine the location of a player on the court; to track a player's movements for the benefit of a television audience; to obtain sports data such as speed, acceleration, cutting and power, to be used in the training or evaluation of a player. As other examples, the uniform or wearable equipment sensor-derived information may be useful for improved item design, for on-going monitoring of the item, for determining the effective lifespan of an item, for determining when an item should be replaced, for comparing various items, and for evaluating the effectiveness of an item.

The wearable equipment and uniform sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event. The uniform and wearable equipment sensors may be used to monitor the physiology of the athlete, by measuring, for example, heart rate, blood pressure, internal temperature, glucose levels, etc.

B.7. Golf

As noted above, within one aspect of the invention sports equipment and areas of play are provided with sensors for golf. Briefly stated, golf is a game played on a large outdoor course with a series of 9 or 18 holes spaced far apart, the object being to propel a small, hard ball with the use of various clubs into each hole with as few strokes as possible. Golf is one of the few ball games that do not require a standardized playing area. Instead, the game is played on a course, in general consisting of an arranged progression of holes. Each hole on the course must contain a tee box to start from, and a putting green containing the actual hole. There are various other standardized forms of terrain in between, such as the fairway, rough, and hazards, but each hole on a course, and indeed among virtually all courses, is unique in its specific layout and arrangement. As mentioned above, golf competition is generally played for the lowest number of strokes by an individual, known simply as stroke play, or the lowest score on the most individual holes during a complete round by an individual or team, known as match play.

Figure 41:
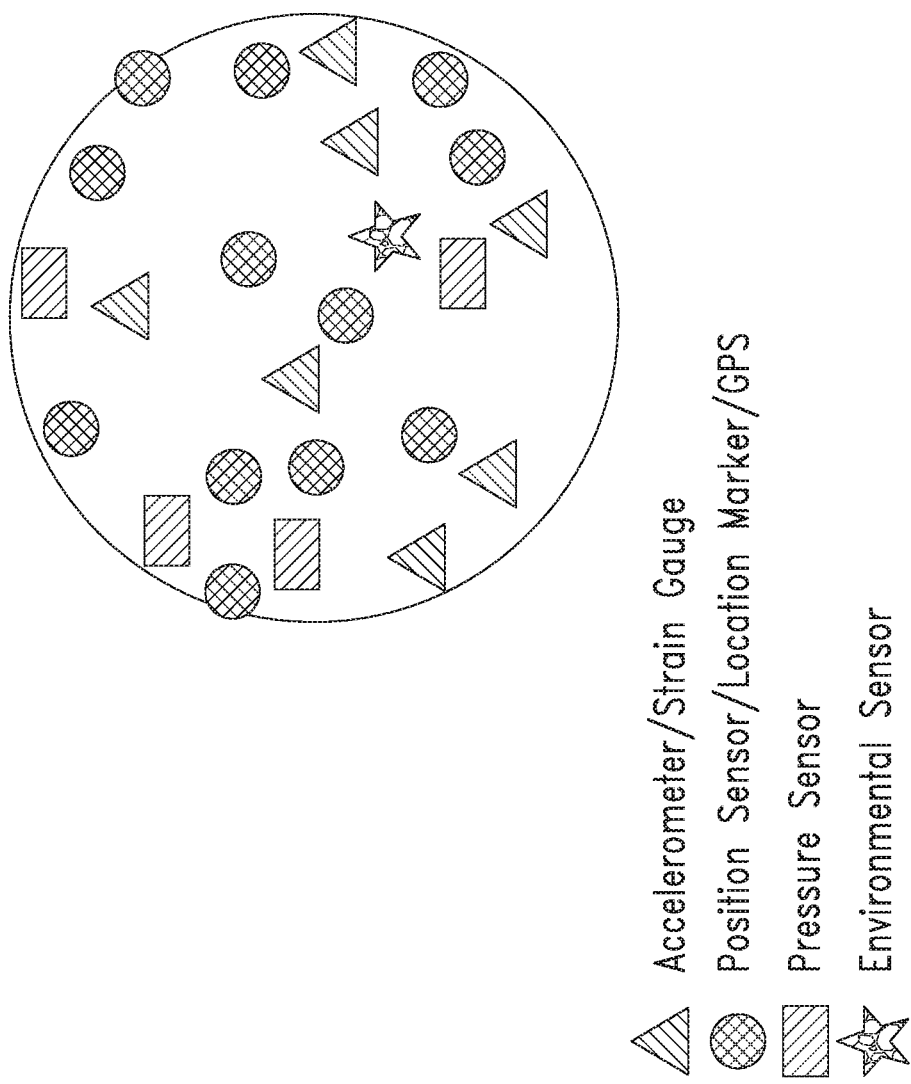
FIG. 41 is an illustration of a variety of sensors on a golf ball, according to one embodiment of the invention.

Within one aspect of the invention a golf ball is provided with one or more sensors (including for example sensor modules), as shown in FIG. 41. For example, one or more position sensors, location markers and/or GPS sensors may be contained on or within a golf ball. In addition, or alternatively, one or more accelerometers and/or strain gauges may be contained on or within a golf ball. In addition, or alternatively, one or more pressure sensors may be contained on or within a golf ball. In addition, or alternatively, one or more environmental sensors may be contained on or within a golf ball. The sensors can be distributed throughout the golf ball randomly or in an ordered manner.

Position sensors, location markers and GPS devices can be utilized to track the golf ball as it travels along the course. The sensors can be utilized, among other things, to: a) determine the location of the golf ball on or off the course, such as to determine whether the ball has gone out-of-bounds or found its way into a hazard; b) whether the ball is hit from the tee box, and from which tee box; c) accurately determining the distance that a ball travels after being hit by the club; d) the speed, spin, carry and bounce of the ball, where this information is of interest to both players, coaches and fans; e) locating a ball which is not readily visible; and f) tracking the ball for the benefit of the television audience.

Within related embodiments one or more environmental sensors can be placed on or within a golf ball. Environmental sensors can be utilized to monitor the temperature, wind speed, wind direction, humidity, moisture, and other environmental conditions such as air quality (e.g., pollution and/or pollen).

Within other embodiments, one or more pressure sensors can be placed on or within a golf ball. Pressure sensors can be utilized to, amongst other things: a) monitor impact, such as occurs when the golf ball hits the ground or is impacted by the club; and b) obtain data about golf ball movement.

Within yet other embodiments one or more accelerometers, gyroscopes and/or strain gauges can be placed on or within a golf ball. Such sensors can be utilized to determine, among other things: a) the speed, acceleration, and/or velocity of the golf ball; b) the direction, location and/or impact of the golf ball; c) measuring driving distance and accuracy; d) tracking putting performance and breaks in the green; e) detecting and quantifying spin of the traveling golf ball; f) enhancing the home viewing experience; and g) measuring the performance of a player, for purposes of training, evaluation and player comparison.

Figure 42:
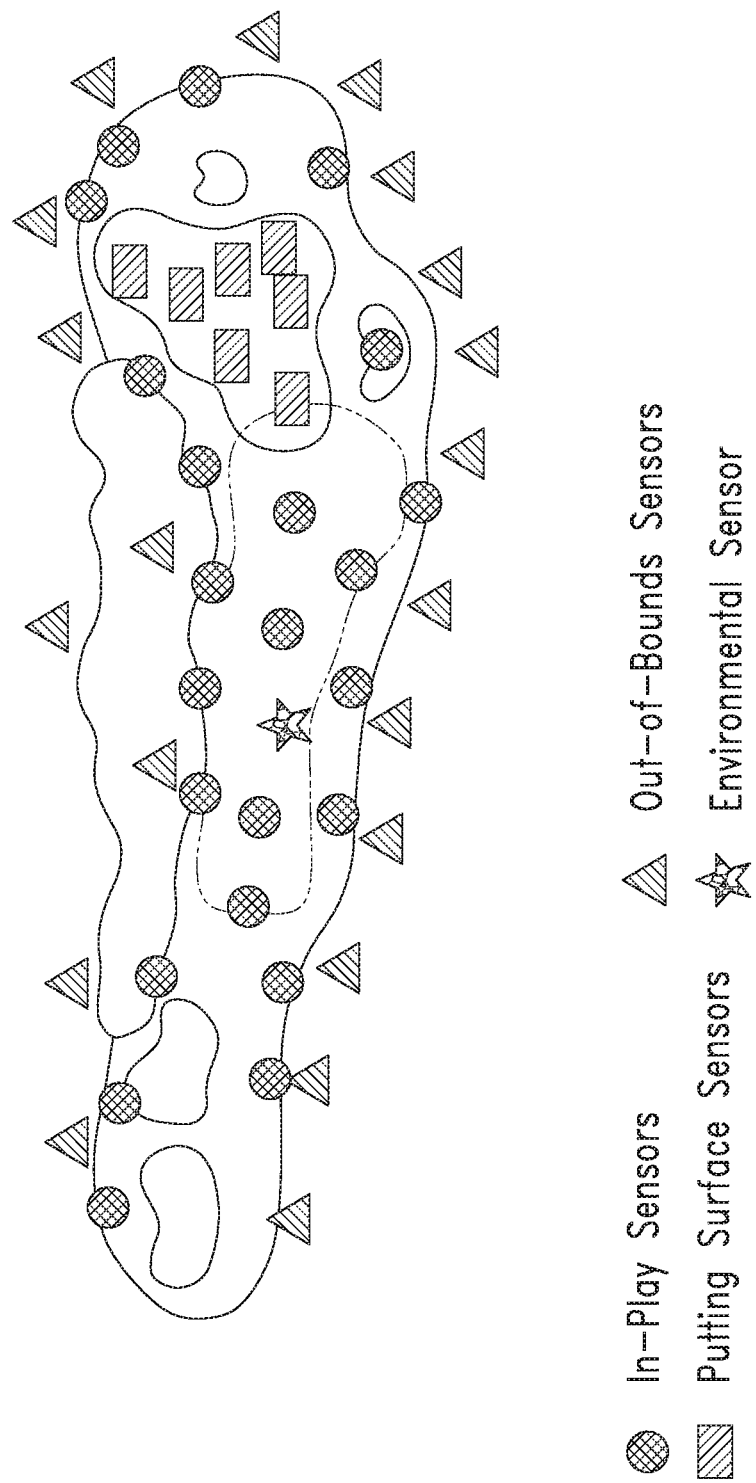
FIG. 42 is an illustration of a variety of sensors on a golf course, according to one embodiment of the invention.

Within other aspects of the invention the golf course (as shown in FIG. 42) is set up to have one or more sensors. Sensors can be distributed randomly and/or specifically throughout the course, for example, on and around the greens, or the holes, or the hazards. For example, within one embodiment of the invention, position sensors, locations markers, GPS sensors are provided for a golf course. Such sensors can be utilized to monitor in-play and out-of-play regions. Within certain preferred embodiments of the invention, course sensors can be utilized along with equipment sensors and/or uniform sensors to determine actual play of the game. For example, by comparing the position or location of a course sensor with one or more golf ball or equipment (e.g., club) sensors one can determine: a) the location of an event on the course; b) accurate position of the golf ball; c) a player who has been playing a particular ball; and d) distances that the ball travels between being hit; and e) for tracking play on the course.

Position sensors distributed throughout the in-play portion of the course may interact with and differentiate information received from ball sensors, club sensors, uniform sensors and other sensors. For example, these sensors may identify the location of the ball on the course, optionally in conjunction with information from other sensors, such as club sensors; or the sensors may be clustered adjacent to putting surfaces. The course sensors may be used to make accurate calls, such as whether the ball hits the course in-bounds or out-of-bounds. Position sensors may detect when and where the ball hits the ground. In-play position sensors may also be used to track the ball for the benefit of a television audience. In-play position sensors may optionally be clustered adjacent to boundaries and/or hazards. In-play position sensors may be used to measure driving distance and shot distance, as well as to measure putting distance. In-play position sensors may determine whether the golf ball is located on the putting surface. The in-play position sensors, optionally in contact with sensor located in and around hazards, may be used to determine whether a golf ball is in a hazard or not. In-play position sensors may provide information of interest to television viewers, particularly related to tracking the location of the golf ball, which is particularly useful when the location of the ball is obscured from view. The in-play position sensors may be used to identify penalty-earning behavior, such as grounding the club, moving the ball, marking, dropping, etc.

Similarly, positions sensors may be located in out-of-play areas of the course. These out-of-play sensors may be used to capture information that can be used in conjunction with information from other sensors, such as golf ball sensors. The out-of-play sensors may be used to detect and determine accurate ball placement in the event of a lost ball. Out-of-play sensors may be clustered on hazard boundaries to determine if and when a golf ball passes those boundaries. The out-of-play sensors may be used for accurate ball marking, as useful in, for example, determining where a golf ball went out of bounds. Other sensors may additionally or alternatively be placed in the out of play area, including environmental sensors that may monitor conditions such as temperature, humidity, moisture, and air quality (pollution, pollen, etc.).

Yet another location for position sensors including location markers, GPS indicators, and pressure sensors is as putting green sensors, which may be distributed throughout the playing surface in the putting green area. These position sensors may be interact with other sensors, such as golf ball sensors. These position sensors may be used to determine whether the ball has reached the putting green and for how many strokes it was located within the putting green. These positions sensors may distinguish between whether golf ball is on the green or on the fringe. These position sensors, optionally in conjunction with data received from other sensors, e.g., golf ball sensors, may provide information about the green terrain, a break in ball movement, and the overall speed of the green. These position sensors can track putts, and provide putting statistics such as putt distance and putting accuracy. In one embodiment, position sensors and/or pressure sensors are clustered around the hole of a putting green to be able to accurately determine whether the ball falls into the hole. Putting green sensors may also be used to track the location of the golf ball for the benefit of television viewers.

Sensors may be located in, on or around the hole of a golf course. Exemplary sensors include position sensors, location markers, GPS indicators, pressure sensors and accelerometers. A hole sensor may be used in conjunction with other sensors, such as sensors that are located on the player's equipment, sensors that are located on the equipment of another player, and/or sensors that are located elsewhere on the course. Sensors located at various places, and/or sensors located at the same or nearly the same place but which respond to different stimuli or emit different signals, may be used in combination to provide more complete information about a specific time or event. Hole sensors may provide information about contact between the hole and the golf ball, such as speed and force of the ball hitting the target hole. The hole sensor may also indicate whether the golf ball went into the hole but then immediately exited the hole. The hole sensors may be used to assist in tracking the ball, especially for television viewers, and particularly when the ball is obscured from view.

Figure 43:
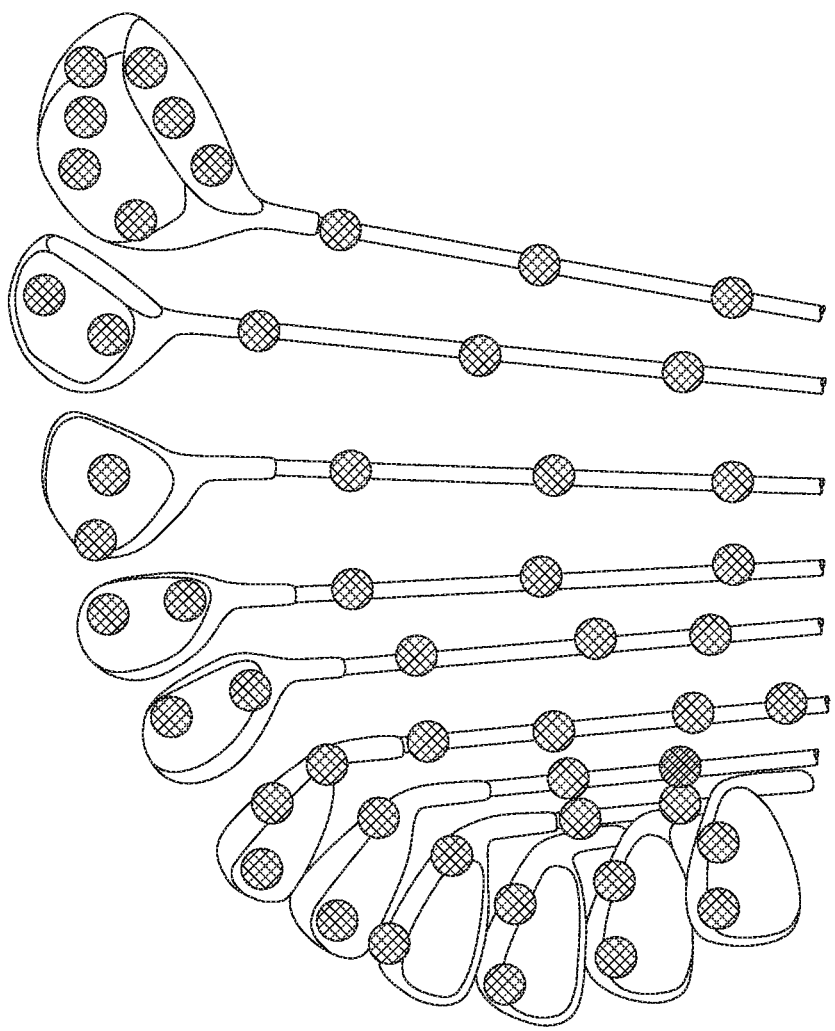
FIG. 43 is an illustration of a variety of sensors on a golf club, according to one embodiment of the invention.

Within yet other aspects of the invention, one or more sensors are provided on the equipment and/or uniform used by the players. For example, sensors may be located on the golf clubs. As shown in FIG. 43, one or more sensors such as position sensors, location markers, GPS indicators, accelerometers, gyroscopes and/or pressure sensors can be included on a golf club. Such sensors can be distributed throughout the club (inside and out) randomly and/or in specific locations, such as on the handle of the club or clustered on the face of the club or along the shaft of the club. A golf club sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from gold club sensors, optionally in combination with information obtained from internal or external sensors located elsewhere, may be used for various purposes. For instance, the information from golf club sensors may be used in conjunction with information from golf ball sensors, course sensors, uniform sensors, etc. to more accurately or completely characterize an event. The club sensor may be used to monitor player technique, such as evaluating the speed, impact and force with which the players contacts the club with the golf ball. The club sensor may be used as a training or evaluation aid, where the information obtained from the club sensor such as club speed, club impact (e.g., where does the golf ball impact the club, and how many misses and hits occur), club power, club force, club acceleration, and club handling is analyzed and used by trainers and coaches to help the golfer improve performance. The information from a club sensor may be transmitted to fans in order to provide a more in-depth understanding of the playing events, and thereby lead to enhanced fan enjoyment. The club sensor may detect when the club hits the ground, when divots are formed, and when spin is imparted to the golf ball. The club sensor may identify situations where a penalty should be called, such as when a player grounds a club in a hazard. The club sensor may provide information about putting performance. As other examples, the club sensor-derived information may be useful for improved club design, for on-going monitoring of golf clubs, for determining the effective lifespan of a golf club, for determining when a golf club should be replaced, for comparing various golf clubs, and for evaluating the effectiveness and accuracy of a golf club.

Any piece of a golf uniform or clothing or wearable equipment such as eye protection may contain sensors. As an example, which is shown in FIG. 44, one or more sensors such as position sensors, location markers, GPS indicators, accelerometers, gyroscopes and/or pressure sensors can be included on a golf shoe. Such sensors can be distributed throughout the shoe (inside and out) randomly and/or in specific locations, such as on the cleats of the shoe or clustered at the toe or heel of the shoe. The golf shoe sensors may be used in conjunction with other sensors, such as sensors that are located on the player's other equipment, sensors that are located on the equipment of another player, and/or sensors that are located on the golf course. Sensors located at various places, and/or sensors located at the same or nearly the same place but which respond to different stimuli or emit different signals, may be used in combination to provide more complete information about a specific time or event.

The information obtained from golf shoe sensors, optionally in combination with information obtained from internal or external sensors located elsewhere, may be used for various purposes. For example, golf shoe sensor information may indicate whether a golfer is pushing downward more forcefully on one foot versus the other foot. Gold shoe sensor information may be used to track the player's location. As other examples, the sensor-derived information may be useful for improved shoe design, for on-going monitoring of shoes, for determining the effective lifespan of the shoe, for determining when a golf shoe should be replaced, and for comparing various golf shoes. The information from a golf shoe sensor may be used by trainers to guide the athlete to improved performance.

In combination with sensors located elsewhere, such as ball sensors, course sensors and uniform sensors, the shoe sensor may provide valuable information for evaluating athletic performance or other uses such as positioning the athlete relative to other locations. In addition to determining whether the athlete was in the tee box or in a hazard or on the green at a particular time, the shoe sensor may help determine how the athlete used their feet in response to different challenges including terrains. The shoe sensor will provide data that is useful in measuring the player's performance, where such information may be interpreted in conjunction with other sensor information and sensor locations, such as clothing sensors, to break down the player's swing to allow a coach to analyze where improvements may be made.

As another example of a piece of golf uniform or clothing or wearable equipment such as eye protection containing sensor, and as shown for example in FIG. 44, one or more sensors such as position sensors, location markers, GPS indicators, accelerometers, gyroscopes, pressure sensors and/or physiology sensors can be included on the clothing worn by the golfer, i.e., the uniform. Such sensors can be distributed throughout the clothing (inside and out) randomly and/or in specific locations. A uniform sensor may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event.

The information obtained from golf uniform or wearable equipment sensors, optionally in combination with information obtained from internal or external sensors located elsewhere, may be used for various purposes. For instance, the information from golf uniform or wearable equipment sensors may be used in conjunction with information from golf ball sensors, course sensors, other uniform sensors, etc. to more accurately or completely characterize an event. An exemplary event is the swing of a golfer. The sensors may be used to characterize the swing dynamics in terms of relevant factors such as shoulder turn, hip turn, hand movements, knee movements and feet movements. The sensors on a golf uniform or wearable equipment may be used to determine the location of a player on the course; to track a player's movements for the benefit of a television audience; to obtain sports data such as speed, acceleration, cutting and power, to be used in the training or evaluation of a player. As other examples, the uniform or wearable equipment sensor-derived information may be useful for improved item design, for on-going monitoring of the item, for determining the effective lifespan of an item, for determining when an item should be replaced, for comparing various items, and for evaluating the effectiveness of an item.

The wearable equipment and uniform sensors may be used in conjunction with other sensors, such as sensors that are located on the player's other equipment, sensors that are located on the equipment of another player, and/or sensors that are located on the field of play. Sensors located at various places, and/or sensors located at the same or nearly the same place but which respond to different stimuli or emit different signals, may be used in combination to provide more complete information about a specific time or event. The uniform and wearable equipment sensors may be used to monitor the physiology of the athlete, by measuring, for example, heart rate, blood pressure, internal temperature, glucose levels, etc.

B.8. Volleyball

As noted above, within one aspect of the invention sports equipment and areas of play are provided with sensors for volleyball. Briefly stated, volleyball is played in school, e.g., high school and college, and at the Olympic Games. Volleyball is a team sport in which two teams of six active players, separated by a high net, each try to score points against one another by grounding a ball on the other team's court under organized rules. The complete rules of volleyball are extensive, but in general, play proceeds as follows. Points are scored by grounding the ball on the opponents' court, or when the opponent commits a fault. The first team to reach 25 points wins the set and the first team to win three sets wins the match. Teams can contact the ball no more than three times before the ball crosses the net, and consecutive contacts must be made by different players. The ball is usually played with the hands or arms, but players can legally strike or push (short contact) the ball with any part of the body. Through time, volleyball has developed to involve common techniques of spiking, passing, blocking, and setting, as well as specialized player positions and offensive and defensive structures. Because many plays are made above the top of the net, vertical jumping is an athletic skill emphasized in volleyball. Volleyball may be played indoor, however numerous variations of volleyball have developed for casual play, as has the Olympic spin-off sport, beach volleyball.

The overall measurements for a volleyball court is 60 feet by 30 feet. Each side of the court is therefore 30 feet by 30 feet in size. A center line is marked at the center of the court dividing it equally into 30 feet squares. An attack line is marked 10 feet on each side of the center line of the court. A service line is marked 10 feet inside the right sideline on each back line. This is the area from which the server may serve the volleyball. The net is hung directly above the center line at 7 feet 4 inches for women and 8 feet for men.

Figure 45:
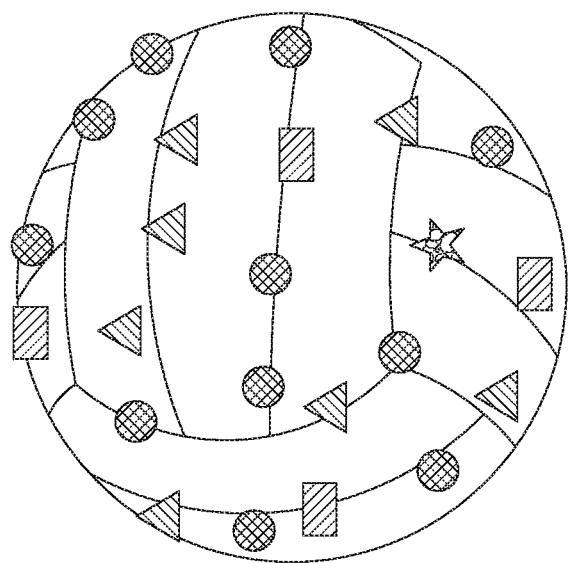
FIG. 45 is an illustration of a variety of sensors on a volley ball, according to one embodiment of the invention.

Within one aspect of the invention a volleyball is provided with one or more sensors (including for example sensor modules). For example, as shown in FIG. 45, one or more position sensors, location markers and/or GPS sensors may be contained on or within a volleyball. In addition, or alternatively, one or more accelerometers and/or strain gauges may be contained on or within a volleyball. In addition, or alternatively, one or more pressure sensors may be contained on or within a volleyball. In addition, or alternatively, one or more environmental sensors may be contained on or within a volleyball. The sensors can be distributed throughout the volleyball randomly or in an ordered manner.

Position sensors, location markers and GPS devices can be utilized to track the volleyball as it travels from player to player, and/or across the volleyball court. The sensors can be utilized, among other things, to: a) determine the location of the volleyball on or off the court, such as to determine whether the ball has crossed over the center line or beyond the court boundaries; b) whether the ball hits the net on service; c) the speed, spin, and impact of the ball, where this information is of interest to both players, coaches and fans; d) the position of the ball relative to the net, where this determination may be made in conjunction with one or more other sensors, e.g., net sensors, and where this determination may be useful in identifying setter interference; and e) tracking the ball for the benefit of the television audience.

Within related embodiments one or more environmental sensors can be placed on or within a volleyball. Environmental sensors can be utilized to monitor the temperature, wind speed, wind direction, humidity, moisture, and other environmental conditions such as air quality (e.g., pollution and/or pollen). This may be particularly useful in beach or other type of volleyball which is played outdoors.

Within other embodiments, one or more pressure sensors can be placed on or within a volleyball. Pressure sensors can be utilized to, amongst other things: a) monitor impact, such as occur when the volleyball contacts a player, the net, or the ground; and b) obtain data about volleyball movement. The information from a pressure sensor may optionally be combined with information from other sensors, e.g., position sensors, in order to evaluate a situation, e.g., to determine whether the volleyball hit the ground or went out-of-bounds. The information from a pressure sensor may optionally be combined with information from other sensors, e.g., uniform sensors, in order to evaluate a situation, e.g., to determine which player was the last player to touch the volleyball before the ball went out-of-bounds, to determine the number of players who touched the ball, to identify a double touch on a set, to determine the length of impact to thereby determine lift, and to obtain data on ball handling, e.g., force of impact.

Within yet other embodiments one or more accelerometers, gyroscopes and/or strain gauges can be placed on or within a volleyball. Such sensors can be utilized to determine, among other things: a) the speed, acceleration, spin and/or velocity of the volleyball; b) the direction, location and/or impact of the volleyball; and c) measuring serving, hitting and blocking of the volleyball. Such sensors may be used to measure the performance of a player, where such information is useful, for example to trainers and coaches seeking to enhance player performance, and to the fans in evaluating and comparing players. Such sensors may provide information that is transmitted to home viewers in order to enhance their viewing experience.

Figure 46:
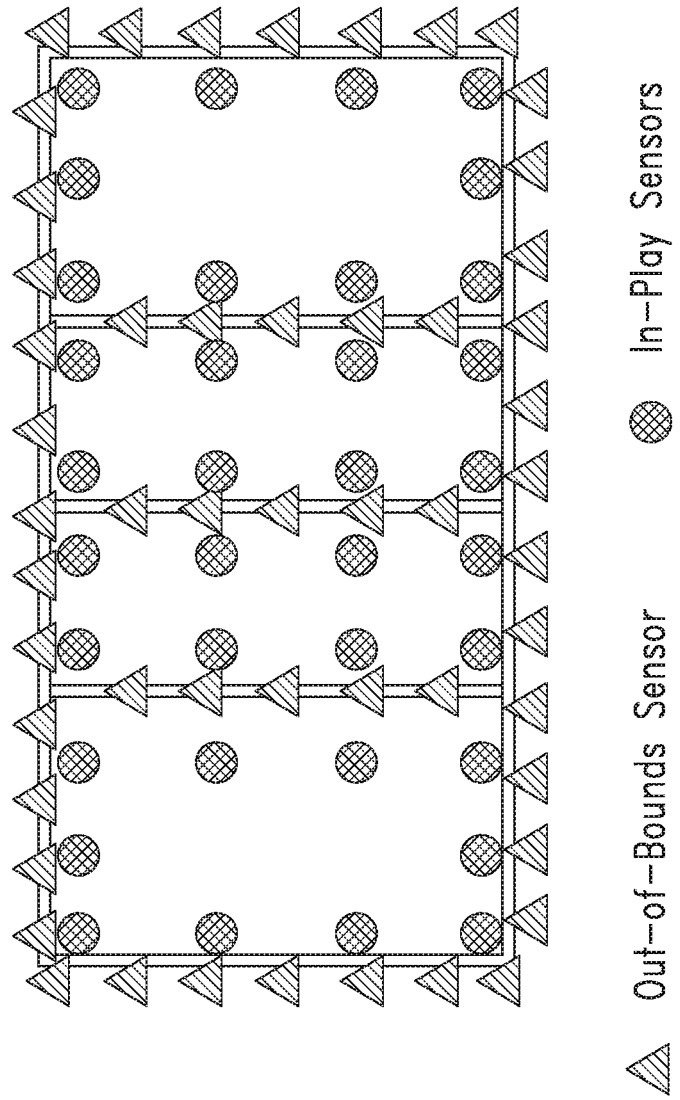
FIG. 46 is an illustration of a variety of sensors on a volley ball court, according to one embodiment of the invention.
Figure 47:
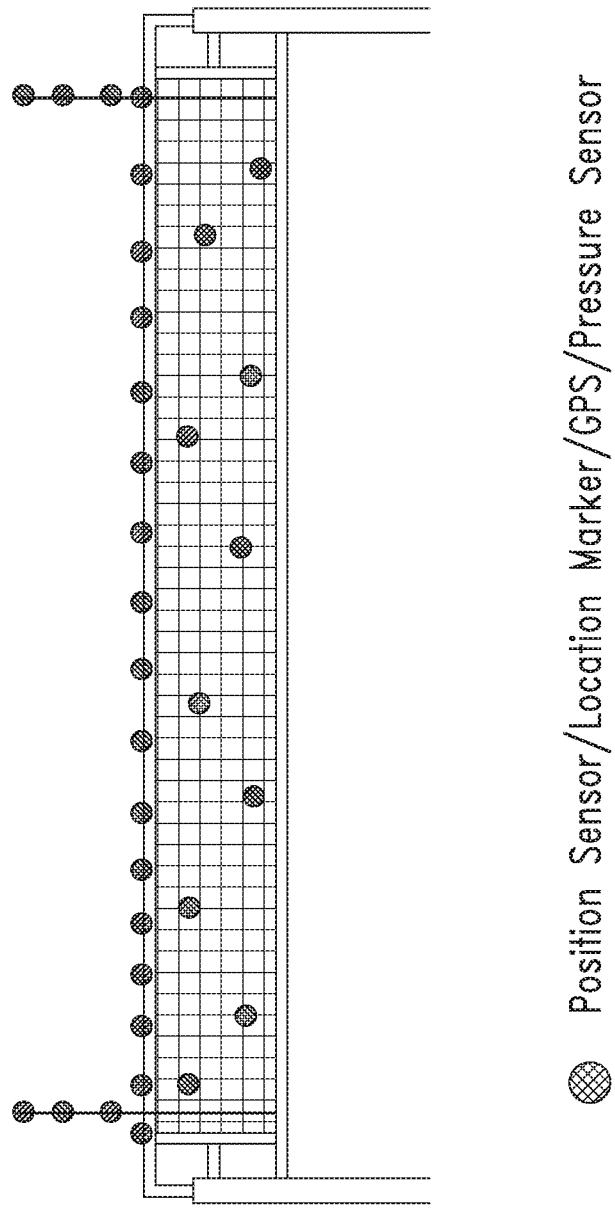
FIG. 47 is an illustration of a variety of sensors on a volley ball net and antennae, according to one embodiment of the invention.

Within other aspects of the invention the volleyball court (as shown in FIGS. 46 and 47) is set up to have one or more sensors. Sensors can be distributed randomly and/or specifically throughout the playing surface, for example, on and around the net or the court boundaries. For example, within one embodiment of the invention, position sensors, locations markers, GPS sensors are provided for a volleyball court. Such sensors can be utilized to monitor in-play and out of play regions. Within certain preferred embodiments of the invention, court sensors can be utilized along with equipment sensors and/or uniform sensors to determine actual play of the game. For example, by comparing the position or location of a court sensor with one or more volleyball sensors one can determine: a) the location of an event on the court; b) accurate position of the volleyball; c) a player who has control of a volleyball; and d) distances that the volleyball travels between being hit; e) the number of times the volleyball is hit before passing over the net; and f) for tracking play on the court.

Position sensors distributed throughout the in-play portion of the volleyball court may interact with and differentiate information received from ball sensors, uniform sensors and other sensors. For example, these sensors may identify the location of the volleyball in the court, and the sensors may be clustered adjacent to the net or court lines. The court sensors may be used to make accurate calls, such as whether the ball hits the court in-bounds or out-of-bounds. Position sensors may detect whether the ball hits the ground before being hit by a player. Position sensors, optionally in combination with other sensors such as shoe sensors, may detect foot fault on service and foot fault on centerline during blocking or attacking. Position sensors may also be used to track the volleyball for the benefit of a television audience.

Similarly, positions sensors may be located in out-of-play areas of the volleyball court. These out-of-play sensors may be used to capture information that can be used in conjunction with information from other sensors, such as volleyball sensors. The out-of-play sensors may be used to detect and determine accurate ball placement in the event of a disputed call. The out-of-play sensors may help identify the location of the volleyball, particularly for television viewers in the even the location of the ball is obscured from view. Other sensors may additionally or alternatively be placed in the out of play area, including environmental sensors that may monitor conditions such as temperature, humidity, moisture, and air quality (pollution, pollen, etc.).

As shown in FIG. 47, sensors may be located on the net, e.g., on the top of the net. Alternatively, or additionally, sensors may be located on antennae that are positioned adjacent to the net. The sensors may be distributed throughout the volleyball net. Exemplary sensors include position sensors, location markers, GPS indicators, pressure sensors and accelerometers. A net sensor may be used in conjunction with other sensors, such as sensors that are located on the player's equipment or uniform, sensors that are located on the equipment or uniform of another player, and/or sensors that are located on the volleyball court. Sensors located at various places, and/or sensors located at the same or nearly the same place but which respond to different stimuli or emit different signals, may be used in combination to provide more complete information about a specific time or event. Net sensor may provide information about contact with the volleyball, such as speed and force of the ball hitting the net. The net sensor may also indicate whether the volleyball has crossed over the net, where this determination may be made in conjunction with other sensors such as court sensors. The net sensors may be used to assist in tracking the ball, especially for television viewers, and particularly when the ball is obscured from view. The net sensors may be used to determine if a player contacted the net, e.g., whether a player touched the net. The net sensors may be used to determine if a player crossed over the net, e.g., whether one or both hands of a player cross over the top of the net as may occur in setter interference. The antennae sensors may detect whether the volleyball hit the antennae.

Figure 48:
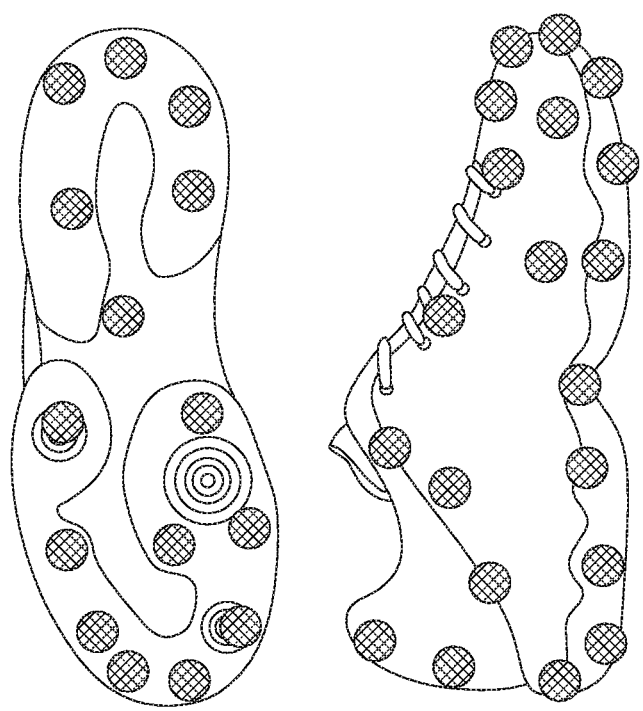
FIG. 48 is an illustration of a variety of sensors on volley ball shoes, according to one embodiment of the invention.

Within yet other aspects of the invention, one or more sensors are provided on the equipment and/or uniform used by the players. Any piece of a volleyball uniform or clothing or wearable equipment such as eye protection may contain sensors. As an example, which is shown in FIG. 48, one or more sensors such as position sensors, location markers, GPS indicators, accelerometers, gyroscopes and/or pressure sensors can be included on a volleyball shoe. Such sensors can be distributed throughout the shoe (inside and out) randomly and/or in specific locations, such as on the toe portion of the shoe or clustered at the heel of the shoe. The volleyball shoe sensors may be used in conjunction with other sensors, such as sensors that are located on the player's other equipment, sensors that are located on the equipment of another player, and/or sensors that are located on the volleyball court. Sensors located at various places, and/or sensors located at the same or nearly the same place but which respond to different stimuli or emit different signals, may be used in combination to provide more complete information about a specific time or event.

The information obtained from shoe sensors, optionally in combination with information obtained from internal or external sensors located elsewhere, may be used for various purposes. For example, shoe sensor information may indicate whether the feet of a player or in-bounds or out-of-bounds during service; to indicate whether foot faults occurred during serving; to indicate whether a foot passed across the center line; and to indicate whether back-row attack occurred. As other examples, the sensor-derived information may be useful for improved shoe design, for on-going monitoring of shoes, for determining the effective lifespan of the shoe, for determining when a shoe should be replaced, and for comparing various shoes. The information from a shoe sensor may be used by trainers to guide the athlete to improved performance. Shoe sensors may detect the number and length of steps taken by an athlete during play, the height above the ground that an athlete achieves during play, the extent to which an athlete lands on one or two feet and the extent to which a foot comes down more on the heel or toe, and the time in the air compared to the force of impact with the ground. All of this information may be useful to coaches and trainers as well as the athlete themselves.

As another example of a piece of volleyball uniform or clothing or wearable equipment such as eye protection containing sensor, and as shown for example in FIG. 49, one or more sensors such as position sensors, location markers, GPS indicators, accelerometers, gyroscopes, pressure sensors and/or physiology sensors can be included on a volleyball uniform article. Such sensors can be distributed throughout the uniform (inside and out) randomly and/or in specific locations. A uniform sensor may be used in conjunction with other sensors, such as sensors that are located elsewhere on the player's uniform or equipment, sensors that are located on the uniform or equipment of another player, sensors on the volleyball, and/or sensors that are located on the volleyball court. Sensors located at various places, and/or sensors located at the same or nearly the same place but which respond to different stimuli or emit different signals, may be used in combination to provide more complete information about a specific time or event.

The information obtained from volleyball uniform or wearable equipment sensors, optionally in combination with information obtained from internal or external sensors located elsewhere, may be used for various purposes. For instance, the information from volleyball uniform or wearable equipment sensors may be used in conjunction with information from volleyball sensors, court sensors, other uniform sensors, etc. to more accurately or completely characterize an event. An exemplary event is a sports injury, where the sensors may provide information about, for example, the force, impact, rotation and/or acceleration of a volleyball or other item that was involved in the impact. The sensors on a volleyball uniform or wearable equipment may be used to determine the location of a player on the court; to track a player's movements for the benefit of a television audience; to obtain sports data such as speed, acceleration, stopping, lateral movement, arm swing, and force of impact, to be used in the training or evaluation of a volleyball player. As other examples, the uniform or wearable equipment sensor-derived information may be useful for improved item design, for on-going monitoring of the item, for determining the effective lifespan of an item, for determining when an item should be replaced, for comparing various items, and for evaluating the effectiveness of an item.

The wearable equipment and uniform sensors may be used in conjunction with other sensors, such as sensors that are located on the player's other equipment, sensors that are located on the equipment of another player, and/or sensors that are located on the court. Sensors located at various places, and/or sensors located at the same or nearly the same place but which respond to different stimuli or emit different signals, may be used in combination to provide more complete information about a specific time or event. The volleyball uniform and wearable equipment sensors may be used to monitor the physiology of the athlete, by measuring, for example, heart rate, blood pressure, internal temperature, glucose levels, etc.

C. Further Aspects of Sports Equipment and/or Areas of Play Having Sensors

C.1 Methods for the Manufacture of Sports Equipment and/or Areas of Play Having Sensors As discussed herein, sports equipment and/or areas of play can readily be manufactured to have or contain sensors (including SM) utilizing readily available techniques. For example during the manufacturing process, or even after manufacture (e.g., in the case of uniforms, gloves, and helmets), sensors (including SM) can be added to sports equipment. Similarly, areas of play (e.g., fields and courts) can be manufactured with sensors (including SM) during construction, or, retrofitted to contain sensors (including sensor modules) as described herein.

Within further embodiments, the present disclosure provides a method of making sports equipment by 3D printing, additive manufacturing, or a similar process whereby the sports equipment is formed from powder or filament that is converted to a fluid form such subsequently solidifies as the desired shape. For convenience, such processes will be referred to herein as printing processes or 3D printing processes. The present disclosure provides a method of making sports equipment by a printing process, where that sports equipment includes a sensor (e.g., a SM). The sensor (e.g., SM, optical system or laser)(e.g., SM, optical system or laser) may be separately produced and then incorporated into the sports equipment during the printing process. For example, a sensor (e.g., SM, optical system or laser)(e.g., SM, optical system or laser) may be placed into a desired position and the printing process is carried out around the sensor (e.g., SM, optical system or laser)(e.g., SM, optical system or laser) so that the sensor (e.g., SM, optical system or laser)(e.g., SM, optical system or laser) becomes embedded in the printed sports equipment. Alternatively, the printing process may be started and then at appropriate times, the process is paused to allow a sensor (e.g., SM, optical system or laser)(e.g., SM, optical system or laser) to be placed adjacent to the partially completed sports equipment. The printing process is then re-started and construction of the sports equipment is completed. The software that directs the printing process may be programmed to pause at appropriate predetermined times to allow a sensor (e.g., SM, optical system or laser)(e.g., SM, optical system or laser) to be added to the partially printed sports equipment.

In addition, or alternatively, the sensor (e.g., SM, optical system or laser)(e.g., SM, optical system or laser) itself, or a portion thereof may be printed by the 3D printing process. Likewise, electronic connectively to, or from, or between, sensor or ISMs may be printed by the 3D printing process.

For example, conductive silver inks may be deposited during the printing process to thereby allow conductivity to, or from, or between sensor (e.g., SMs) of a sports equipment. See, e.g., PCT publication nos. WO 2014/085170; WO 2013/096664; WO 2011/126706; and WO 2010/0040034 and US publication nos. US 2011/0059234; and US 2010/0037731. Thus, in various embodiments, the present disclosure provides sports equipment wherein the sensor (e.g., SM, optical system or laser)(e.g., SM, optical system or laser) is printed onto a substrate, or a substrate is printed and a sensor (e.g., SM, optical system or laser)(e.g., SM, optical system or laser) is embedded or otherwise incorporated into or onto the substrate, or both the substrate and the sensor (e.g., SM, optical system or laser)(e.g., SM, optical system or laser) are printed by a 3D printing technique.

3D printing may be performed using various printing materials, typically delivered to the 3D printer in the form of a filament. Two common printing materials are polylactic acid (PLA) and acrylonitrile-butadiene-styrene (ABS), each being an example of a thermoplastic polymer. When strength and/or temperature resistance is particularly desirable, then polycarbonate (PC) may be used as the printing material. Other polymers may also be used. See, e.g., PCT publication nos. WO 2014/081594 for a disclosure of polyamide printing material. When metal parts are desired, a filament may be prepared from metal or metal alloy, along with a carrier material which ultimately will be washed or burned or otherwise removed from the part after the metal or metal alloy has been delivered.

When the sports equipment is of a particularly intricate shape, it may be printed with two materials. The first material is cured (using, e.g., actinic radiation) as it is deposited, while the second material is uncured and can be washed away after the sports equipment has been finally printed. In this way, significant hollow spaces may be incorporated into the sports equipment.

Additive manufacturing is a term sometimes used to encompass printing techniques wherein metal or metal allow is the material from which the desired part is made. Such additive manufacturing processes utilizes lasers and build an object by adding ultrathin layers of materials one by one. For example, a computer-controlled laser may be used to direct pinpoint beams of energy onto a bed of cobalt-chromium alloy powder, thereby melting the alloy in the desired area and creating a 10-30-micron thick layer. Adjacent layers are sequentially and repetitively produced to create the desired sized item. As needed, a sensor (e.g., SM, optical system or laser)(e.g., SM, optical system or laser) may be embedded into the alloy powder bed, and the laser melts the powder around the sensor (e.g., SM, optical system or laser)(e.g., SM, optical system or laser) so as to incorporate the sensor (e.g., SM, optical system or laser)(e.g., SM, optical system or laser) into the final product. Other alloys, including titanium, aluminum, and nickel-chromium alloys, may also be used in the additive manufacturing process. See, e.g., PCT publication nos. WO 2014/083277; WO 2014/074947; WO 2014/071968; and WO 2014/071135; as well as US publication nos. US 2014/077421; and US 2014/053956.

Accordingly, in one embodiment the present disclosure provides a method of fabricating a sensor or ISM-containing sports equipment, the method comprising forming at least one of a sensor (e.g., SM, optical system or laser)(e.g., SM, optical system or laser) and a support for the sensor (e.g., SM, optical system or laser)(e.g., SM, optical system or laser) using a 3D printing technique. Optionally, the 3D printing technique may be an additive manufacturing technique. In a related embodiment, the present disclosure provides a sports equipment that is produced by a process or comprising a 3D printing process, such as an additive manufacturing process, where the sports equipment includes a sensor or ISM.

Disclosure of 3D printing processes and/or additive manufacturing is found in, for example PCT publication nos. WO 2014/020085; WO 2014/018100; WO 2013/179017; WO 2013/163585; WO 2013/155500; WO 2013/152805; WO 2013/152751; WO 2013/140147 and US publication nos. 2014/048970; 2014/034626; US 2013/337256; 2013/329258; US 2013/270750.

Within yet other embodiments of the invention methods of fabricating sports equipment having a sensor (e.g., SM, optical system or laser) are provided comprising the steps of forming sports equipment (e.g., as described herein), and implanting, placing or inserting a sensor (e.g., SM, optical system or laser) into the equipment during the fabrication process. Within further embodiments, such methods further comprise the steps of determining a sports equipment (e.g., a glove, hat or helmet) shape that is suitable for a particular subject, or a particular group of subjects, and utilizing CAD programs or other 3-D design program to design suitable sports equipment for a particular subject, or, for a group of subjects. Within yet further embodiments, one or more sensors (e.g., SMs) can be inserted, placed, or otherwise distributed on, or within sports equipment in a particular location for a particular subject.

C.2 Uses of Combinations of Sensors

As noted above, data from groups of sensors can be combined to collectively provide information which is relevant to a sport. For example, within one embodiment methods are provided for monitoring the safety and/or efficacy of sports equipment and/or area of play comprising the steps of a) collecting data from one of the sensors (e.g., SM, optical system or laser) on and/or within the sports equipment and/or area of play; and b) analyzing the data to determine whether the sports equipment or area of play is showing signs of wear, deterioration, defect, or other form of change, and thereby determining whether said sports equipment or area of play is safe and/or suitable for use in the sport. Within preferred embodiments data from multiple sensors can be obtained in order to form a sufficient database for analysis.

Within other embodiments methods are provided for determining scoring in a sport, comprising the steps of a) obtaining data from one or more sensors (e.g., SM, optical system or laser)(e.g., SM, optical system or laser) on and/or within the sports equipment or area of play, and b) analyzing the data in order to determine whether a player has scored. For example, data from sensors in a ball and in a basketball hoop and net can be analyzed in order to determine their proximity over time, in order to sensors whether a ball has gone through a hoop. Similarly, sensors in a hockey puck and hockey net, football and football goal, (and other objects of play and areas of play as described herein) can be analyzed in order to assess movement of an object through a goal.

Within other embodiments methods are provided for enforcing rules of play of a sport, comprising the steps of a) obtaining data from one or more sensors (e.g., SM, optical system or laser) (e.g., SM, optical system or laser) on and/or within the sports equipment or area of play, and b) analyzing the data in order to determine whether a rule has of the sport has been violated. For example, sensors in a hockey stick and in a player's jersey can be analyzed in order to determine whether there is inappropriate contact during a game.

Within yet other embodiments methods are provided for monitoring the safety of players, comprising the steps of a) obtaining data from one or more sensors (e.g., SM) on and/or within the sports equipment or area of play, and b) analyzing the data in order to determine whether a player is currently subject to a safety concern, or, may become the subject of a safety issue over time. For example, within one embodiment of the invention headwear of a player (e.g., a football helmet or a hockey helmet) can be monitored for impact. If a sufficient impact occurs, and/or a number of impacts of a particular force occur over time, a player can be required to leave a game and/or seek medical attention. Within certain preferred embodiments of the invention data from impacts or other forces acting on headwear can be maintained over the life of a player, and once a total quantity (e.g., total amount of force, number of impacts, or number of impacts of a particular force) have been recorded by a player, that player would be required to retire from the game.

Within another embodiment of the invention methods are provided for evaluating the performance and or training of a player, comprising the steps of a) obtaining data from one or more sensors (e.g., SM, optical system or laser)(e.g., SM, optical system or laser) on and/or within the sports equipment or area of play, and b) analyzing the data in order to determine the performance and/or efficacy of training of a player. Within related embodiments data from a player can be compared over time in order to determine performance of the player, and the efficacy of a training regimen. Within other embodiments the performance of one player can be compared against another. For example, within one embodiment of the invention the performance of a baseball player in throwing a ball can be analyzed over time based upon a collection of data from sensors in the ball and the player's uniform. Player movement can be assessed over time and utilized to i) assess current training; and ii) suggest certain training for the future. Players can be compared vs. one another, and such data can be utilized the likelihood of player excelling in the sport as the player matures.

Within other embodiments of the invention methods are provided for enhancing the entertainment and/or viewing experience of spectators, comprising the steps of a) obtaining data from one or more sensors (e.g., SM, optical system or laser)(e.g., SM, optical system or laser) on and/or within the sports equipment or area of play, and b) analyzing the data in order to provide real-time measurements of the sport. For example, spectators (whether live or via other mode of viewing, e.g., internet-based video streaming) can be updated with data as it occurs during the sport. Examples of live data that can be presented including the speed of an object of the game (e.g., speed of the ball or bat in baseball), the speed of a player and the force of a tackle (in football), and the like. Furthermore, comparisons can be made between different players in different games (e.g., how does the tackle of a particular player in football compare with the history of all forceful tackles in football?). Where real historical data does not exist (e.g., the force of a tackle), an estimate can be made based upon historical records (e.g., knowing the speed of a player as recorded in a video image and the historical weight of a player can allow an estimation of the force of a tackle).

Data from multiple sensors as provided herein can be utilized for i) gaming purposes, and/or to provide for more accurate data and estimates for the development of electronic games (e.g., on Xbox, PS4 and other gaming systems); and to provide for statistical outcomes in determining real-world and artificial encounters between: i) different players; ii) different teams; iii) different environments for an area of play; iv) different sports equipment; v) different instruments of the game; and/or vi) different objects associated with an area of play (or, any combination of the above). In addition, physical parameters can be calculated by direct measurement, or by estimation of data collected by the sensors provided herein, (e.g., in order to determine or estimate the movement, speed and force of individual players).

In one embodiment the present invention provides a method comprising sensing a physical quantity and then generating a representation of the sensed quantity, in the context of sports. The sensors (e.g., a SM) are incorporated into or onto sports equipment and/or areas of play, in order to monitor the activities taking place during the sporting event. Optionally, the sensor may be continuously generating a representation of a sensed quantity, e.g., it may be continuously detecting the temperature surrounding the sensor. Optionally, the sensor may generate a representation of a sensed quantity only upon being stimulated, e.g., the sensor may detect pressure upon coming into contact with an opposing surface and thereupon generate a representation of pressure. Optionally, the sensor may generate a qualitative representation of the sensed quantity, e.g., the sensor may detect an increase in pressure. Optionally, the sensor may generate a quantitative representation of the sensed quantity, e.g., the sensor may detect an increase in pressure by a certain amount, e.g., 5%, 1 psi, etc.

The sensed quantities, which may also be referred to as information or data, may be transmitted to a receiver that collects information from a plurality of sensors. The information collected by the receiver will be analyzed to provide a picture of activity taking place during the sporting event. For example, the picture may indicate where a sensor was located or positioned at a particular time, and accordingly where the article carrying the sensor was located or positioned at a particular time. Typically that picture will be a temporal picture, i.e., a timeline of activities that took place during the sporting event. For example, a temporal picture may identify movement of the article that carried a sensor. The analyzed data will be used to describe or characterize specific actions that occurred during the sporting event. For example, did the article carrying the sensor hit a net, or pass through a hoop.

Optionally, data from multiple sources will be used in order to characterize and give meaning to a specific action. For example, did the article pass through the hoop during the timeframe of recognized playing, so as to score points, or after the game or quarter thereof was over in which case no points are scored. In this example, information from one or more sensors must be used in conjunction with information from the game clock. In order to decrease ambiguity of interpretation, information from multiple sensors may be analyzed and used in order to characterize a specific action. For example, information from sensor(s) located on a basketball, and information from sensor(s) located on a hoop, optionally, with information from sensor(s) located on the backboard and/or net, may be used in conjunction to verify that a basketball passed through the hoop, rather than some other object.

The information obtained from sensors may optionally be viewed temporally, i.e., along a timeline. Information from the basketball sensors, which indicate a decrease in pressure as the player throws the basketball, followed by an increase in pressure as the basketball hits the backboard, followed by a decrease in pressure as the basketball falls through the hoop, followed by an increase in pressure as the basketball hits the floor or is caught by a player, can be characterized temporally to show when, e.g., the player threw the basketball, and when the basketball hit the backboard and the floor. This temporal information from the basketball may be used in conjunction with temporal information from the backboard, indicating when the backboard was contacted by an object. Other relevant temporal information may come from the net, which indicates when it sensed an object passing through the net in a downward direction. The information from sensors at multiple locations, optionally when viewed from a temporal perspective, provide the analyst with enough information to use the information to unambiguously answer the question "what happened and when did it happen" such that specific actions that occurred during a sporting event can be given meaningful characterization, e.g., did a player make a basket and thereby increase their team's point score.

Thus, in one embodiment, the present invention provides a party with the tools to collect information from a sensor-containing location, analyze that information, and then use that analyzed information to make determinations about actions that occurred during sporting event in order to give significant meaning to those actions, e.g., did someone score a point, did someone commit a foul, etc. The present invention also provides methods for making these determinations. For example, a method comprising collecting information from sensor-containing locations, analyzing the information, and then using the analyzed information to make determinations, or characterizations, about the sensing that was done by the sensor. The characterization may be whether the sensing was due to the occurrence of, for instance, a goal or a foul.

For example, in one embodiment, a method is provided for describing an activity during a sporting event, the method comprising a) identifying an occurrence of contact between two surfaces, at least one of the two surfaces being a sensor-containing surface; b) identifying each surface being contacted; c) identifying a time when the contact occurred; and d) characterizing the action which caused the contact.

Figure 50:
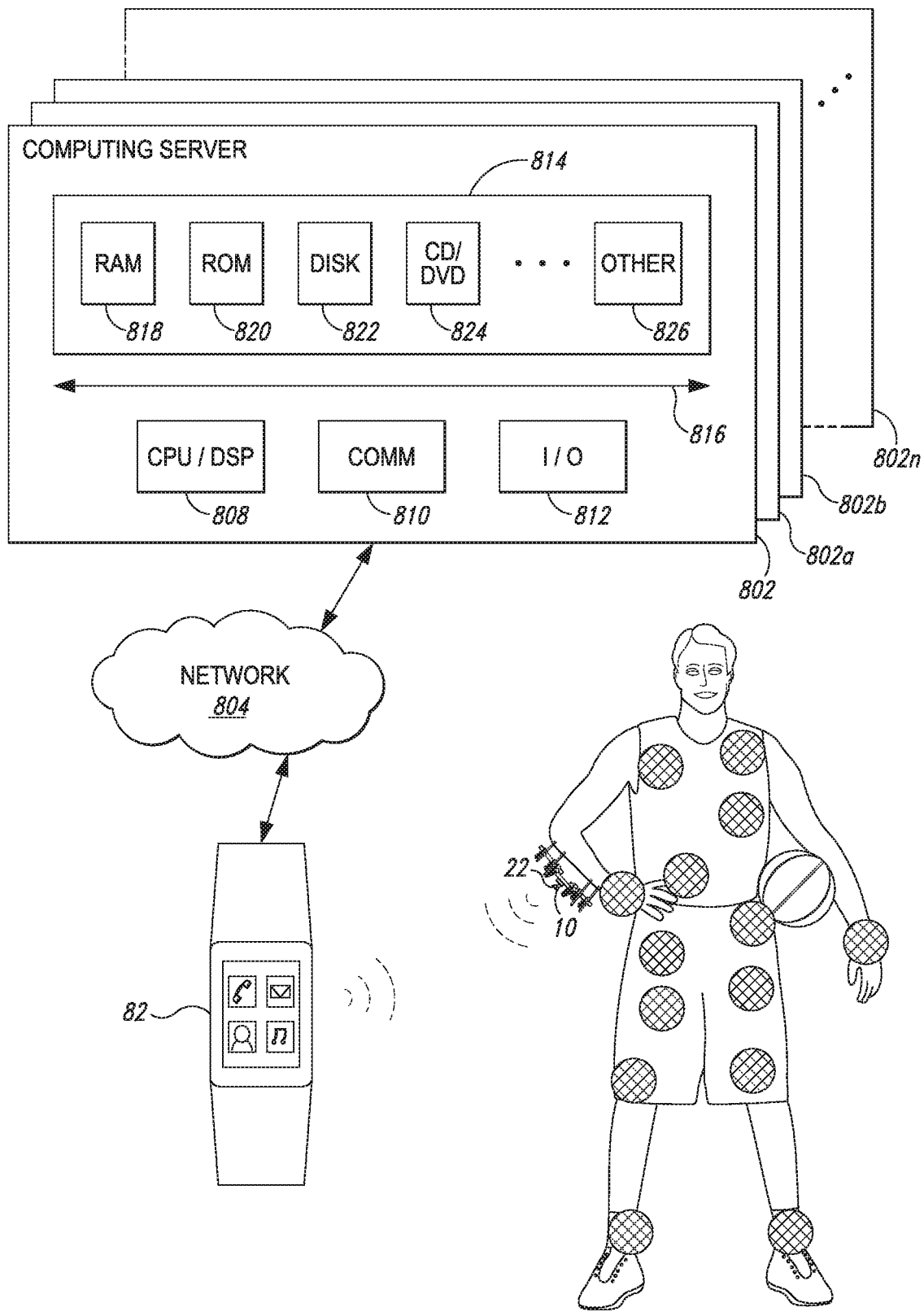
FIG. 50 is a schematic illustration of sensors on sports equipment of a subject which is being probed for data and outputting data, according to one embodiment of the invention.

FIG. 50 is a schematic illustration of sensors on sports equipment of a subject which is being probed for data and outputting data, according to one embodiment of the invention. In FIG. 50, a basketball player is shown with sensor-containing sportswear (shoes, shorts, shirt, wristband). These sensors each sense a physical quantity and then generate a representation of the sensed quantity. Optionally, a sensor may be continuously generating a representation of a sensed quantity, or a sensor may generate a representation of a sensed quantity only upon being stimulated. In any case, the representation of the sensed quantity is output to a computing server which analyzes the information. The computer server will analyze the data to provide analyzed data that is then interpreted to form a basis for characterizing an activity that occurred during the sporting event.

D. Methods for Monitoring Heat Stroke and Exhaustion, as Well as Hypothermia in Players of a Game As noted above, a wide variety of sports equipment or areas of play are provided with sensors (e.g., SM, optical system or laser)(e.g., SM, optical system or laser). Within certain embodiments of the invention the sensors can be utilized to monitor the temperature of a player, as well as the surrounding or ambient temperature in an area of play. Such sensors can be utilized to monitor changes in temperature over time, as well as the total ambient temperature to which a player is exposed. To the extent the player's own temperature increases beyond norms, or, a designated set temperature, the player or a third-party (e.g., a coach or doctor) can be notified.

Hence, within one embodiment of the invention methods are provided for determining n over exposure to temperature, comprising the steps of a) detecting temperature on a subject having at least one of the wearable sports equipment described herein, said sports equipment having one of the sensors described herein which can measure temperature on a subject, b) detecting said temperature on said subject, and c) analyzing said temperature in order to determine whether the temperature of the subject has increased or decreased beyond set norms, or has risen or fallen faster than proscribed. Within further embodiments said method can further comprise the step of (d) notifying said subject or a third-party of any changes of temperature of said subject. Within yet further embodiments of the invention the step of detecting may be a series of detections over time. Within other embodiments a change of 0.5%, 1.0%, or 1.5% or an elevation or decrease of temperature over time (e.g., 0.5, 1.0, 1.5, 2.0, 2.5, 3.0, 3.5, 4 hours or longer) can be indicative of over exposure to conditions which might be harmful to a subject.

E. Further Uses of Sensor-Containing Sports Equipment or Areas of Play

As mentioned previously, sports equipment (and related areas of play) are provided having one or more sensors (including for example 'sensor modules' or 'SMs' as described herein). Such sensors can be placed on or within sports equipment and/or area of play in order to, amongst other things: a) monitor the safety and efficacy of the sports equipment and/or area of play; b) monitor wear and tear of the sports equipment and/or area of play; c) determine scoring; d) determine the applicability and/or enforcement of rules of the game; e) to monitor the safety of players, including over extended times beyond the time of the game; f) evaluate the performance, training and comparison of players; g) enhance the entertainment or viewing experience of spectators (e.g., by providing enhanced information such as the force of impacts, speeds and other physical measurements of the game, and by allowing comparisons with other known or estimated measurements from other games); h) for televised entertainment (e.g., by providing enhanced information as discussed herein); i) for providing actual measurements to be utilized for gaming purposes; j) in order to assist in the development of new and safer sports equipment and areas of play; k) to provide insight into new training methods, skills and/or techniques, and to assess the successfulness of such methods skills and/or techniques; and/or l) to be combined with other sensors on or in the equipment or area of play in order to provide a more complete picture or assessment of the game with respect to any of the above.

SM having sensors on sports equipment have a variety of benefits in the healthcare setting, and in non-healthcare settings (e.g., at home or work). For example, postoperative progress can be monitored (readings compared from day-to-day, week-to-week, etc.) and the information compiled and relayed to both the subject and the attending physician allowing rehabilitation to be followed sequentially and compared to expected (typical population) norms. Within certain embodiments, a wearable device interrogates the SM sensors on a selected or randomized basis, and captures and/or stores the collected sensor data. This data may then be downloaded to another system or device (as described in further detail below).

SM sensors as described herein may be used by athletes or non-athletes in the course of personal training, with or without the presence or assistance of a supervising personal trainer. Personal training includes activities intended to enhance one or more of a person's strength, conditioning, stamina, power, speed, agility, accuracy, coordination, mobility, balance, flexibility, and cardiovascular or respiratory endurance. For example, the sensors may monitor the technique or form of a performed exercise, where the data obtained therefrom may be compared to a desired or goal technique or form. When actual technique varies from the ideal technique, adjustments may be made to change the person's performance and thereby enhance the safety and efficacy of the exercise. The sensors may monitor resistance to movement, where the data therefrom allows a determination of whether a person is able to move increasing resistance over time, i.e., are they getting stronger, and if so, how quickly. For example, the sensors may be placed on a bar bell or dumb bell, or some other resistance-training piece of equipment. The sensors may monitor the extent to which a person is balanced or unbalanced. By tracking this information over time, a determination may be made regarding whether a person's balance is improving. The sensors may monitor the speed with which a person hits a target or achieves some other movement-related goal.

Integrating the data collected by the SM sensors described herein (e.g., contact sensors, position sensors, strain gauges and/or accelerometers) with simple, widely available, commercial analytical technologies such as pedometers and global positioning satellite (GPS) capability, allows further important data to be collected such as, but not restricted to: extent of subject ambulation (time, distance, steps, speed, cadence), subject activity levels (frequency of activity, duration, intensity), exercise tolerance (work, calories, power, training effect), range of motion under various "real world" conditions.

F. Generation of Power from Sports Equipment or Areas of Play

Within certain aspects of the invention, a small electrical generation unit can be positioned along an outer, or alternatively an inner, surface of the sports equipment or area of play, or associated sports equipment or area of play. Briefly, a variety of techniques have been described for scavenging power from small mechanical movements or mechanical vibration. See, for example, the article entitled "Piezoelectric Power Scavenging of Mechanical Vibration Energy," by U. K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283,793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces within the body and movements within the body.

After the electricity is generated by one or more generators, the electricity can be transmitted to any one of the variety of sensors which is described herein. For example, it can be transmitted to any of the sensors shown in Figures. It may also be transmitted to the other sensors described herein. The transmission of the power can be carried out by any acceptable technique. For example, if a SM sensor is physically coupled to the sports equipment or area of play, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

G. Imaging and Self-Diagnosis of Assemblies Comprising Sports Equipment or Areas of Play; Predictive Analysis and Predictive Maintenance Within other aspects of the invention methods are provided for imaging the sports equipment or area of play as provided herein, comprising the steps of (a) detecting the location of one or more SM sensors in the sports equipment or area of play, and/or associated sports equipment or area of play; and (b) visually displaying the location of said one or more SM sensors, such that an image of the sports equipment or area of play and/or sports equipment or area of play is created. Within various embodiments, the step of detecting may be done over time, and the visual display may thus show positional movement over time. Within certain preferred embodiments the image which is displayed is a three-dimensional image. Within preferred embodiments the various images (e.g., 2D or 3D) may be collected and displayed in a time-sequence (e.g., as a moving image or 'movie-like' image).

The present invention provides sports equipment or areas of play and associated sports equipment or areas of play which are capable of imaging through the use of SM having sensors over a wide variety of conditions. For example, within various aspects of the invention methods are provided for imaging the sports equipment or area of play (or portion thereof) having an SM having sensors at a density of greater than 1, 2, 3, 4, 5, 6, 7, 8, 9, 10 or greater than 10 sensors per square centimeter. Within other aspects the sports equipment or area of play sports equipment or area of play comprises an SM having sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the sports equipment or area of play, sports equipment or area of play, as described herein. As noted above, a wide variety of sensors can be utilized therein, including for example, contact sensors, strain gauge sensors, pressure sensors, fluid pressure sensors, position sensors, tissue chemistry sensors, tissue metabolic sensors, mechanical stress sensors, and temperature sensors.

For example, the sports equipment or area of play, sports equipment or area of play, comprising sensors as described herein can be utilized to image anatomy through sensors which can detect positional movement. The sensors used can also include accelerometers and motion sensors to detect movement of the sports equipment or area of play due to a variety of physical changes. Changes in the position of the accelerometers and/or motion sensors over time can be used as a measurement of changes in the position of the sports equipment or area of play over time. Such positional changes can be used as a surrogate marker of sports equipment or area of play anatomy—i.e. they can form an "image' of the sports equipment or area of play to provide information on the size, shape, integrity, alignment and location of changes to the sports equipment or area of play, and/or sports equipment or area of play movement/migration. In particular, as noted above the image data can be collected over time, in order to visually show changes (e.g., a "movie" or 'moving images", which may be in 2D or 3D).

Certain exemplary embodiments will now be explained in more detail. One particular benefit is the live and in-situ monitoring of the subject's recovery with a sports equipment or area of play having an SM as described herein. The SM can, optionally, collect data on a constant basis, during normal daily activities and even during the night if desired. For example, contact sensors within an SM can obtain and report data once every 10 seconds, once a minute, or once a day. Other sensors can collect data more frequently, such as several times a second. For example, it would be expected that the temperature, contact, and/or position data could be collected and stored several times a second. Other types of data might only need to be collected by the minute or by the hour. Still other sensors may collect data only when signaled by the subject to do so (via an external signaling/triggering device) as part of "event recording"—i.e. when the subject experiences a particular event (e.g. pain, injury, instability, etc.)—and signals the device to obtain a reading at that time in order to allow the comparison of subjective/symptomatic data to objective/sensor data in an effort to better understand the underlying cause or triggers of the subject's symptoms. All activity can be continuously monitored post operation or post-procedure and the data collected and stored in the memory located inside the sports equipment or area of play.

The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the sports equipment or area of play to a computer or wireless device. The computer therefore analyzes the data for anomalies, unexpected changes over time, positive or negative trends, and other signs which may be indicative of the health of the subject and the operability of the sports equipment or area of play. Data can be collected and compared with respect to the ongoing and long term performance of the sports equipment or area of play from the strain gauges, the contact sensors, the surface wear sensors, or other sensors which may be present. Hence, within preferred embodiments the data can be collected over time, in order to visually show changes (e.g., a 2D or 3D "movie" or 'moving images").

In one alternative, the subject may also have such a reading device in their home which collates the data from the sports equipment on a periodic basis, such as once per day or once per week. As described above, the subject may also be able to "trigger" a device reading (via an external signaling/triggering device) as part of "event recording." Empowering the subject to see the positive (and negative) effects of various lifestyle and exercise choices. Furthermore, their experience can be shared via the web with other subjects to compare their progress versus expected "norms" for function. The performance of different sports equipment or areas of play can be compared in different subjects (different sexes, weights, activity levels, etc.) to help manufacturers design better sports equipment and areas of play.

H. Methods of Monitoring Assemblies Comprising Sports Equipment or Areas of Play with SMs As noted above, the present invention also provides methods for monitoring one or more of the sports equipment or areas of play or implants with SMs provided herein. For example, FIG. 50 illustrates a monitoring system usable with the sports equipment or area of play or SM 10 as of the type shown in any one of the Figures described herein.

Within other embodiments, the monitoring system may however be composed of passive sensors, which respond to an external signal. For example, according to one embodiment, sufficient signal strength is provided in the initial signal to provide power for the sensor and to carry out the sensing operation and output the signal back to an interrogation module. In other embodiments, two or more signals are sent, each signal providing additional power to the sensor to permit it to complete the sensing operation and then provide sufficient power to transfer the data via the signal path back to the interrogation module. For example, the signal can be sent continuously, with a sensing request component at the first part of the signal and then continued providing, either as a steady signal or pulses to provide power to operate the sensor. When the sensor is ready to output the data, it sends a signal alerting the interrogation module that data is coming and the signal can be turned off to avoid interference. Alternatively, the integration signal can be at a first frequency and the output signal at a second frequency separated sufficiently that they do not interfere with each other. In a preferred embodiment, they are both the same frequency so that the same antenna on the sensor can receive the signal and send signal.

The interrogation signal may contain data to select specific sensors on the sports equipment or area of play. For example, the signal may power up all sensors on the sports equipment or area of play at the same time and then send requests for data from each at different selected times so that with one interrogation signal provided for a set time, such as 1-2 seconds, results in each of the sensors on the sports equipment or area of play collecting data during this time period and then, at the end of the period, reporting the data out on respective signals at different times over the next 0.5 to 2 seconds so that with one interrogation signal, the data from all sensors is collected.

While the wireless signal can be in any frequency range, within certain embodiments an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

The interrogation module is operating under control of the control unit which has a microprocessor for the controller, a memory, an I/O circuit to interface with the interrogation module and a power supply. The control unit may output data to a computer or other device for display and use by, e.g., the subject, a coach or a trainer.

I. Collection, Transmission, Analysis, and Distribution of Data from Assemblies Comprising Sports Equipment or Areas of Play FIG. 50 illustrates one embodiment of an information and communication technology (ICT) system 800 arranged to process sensor data (e.g., data from the SM 10). In FIG. 50, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 50 include computing servers 802, and other devices that are not shown for simplicity.

In FIG. 50, one or more SMs 10 communicate with a remote data receiving device 82. The remote data receiving device can be a wearable device (e.g., a watch-like device, a wrist-band, or other device that may be carried or worn by the subject) can interrogate the SMs over a set (or random) period of time, collect the data, and forward the data on to one or more networks (804). Alternatively, the remote data receiving device 82 can be a stationary device in a hospital, home, or office. The remote data receiving device 82 may collect data of its own accord which can also be transmitted to the network. Representative examples of data that may be collected include location (e.g., a GPS), body or skin temperature, and other physiologic data (e.g., pulse). Within yet other embodiments, the remote data receiving device may notify the subject directly of any of a number of prescribed conditions, including but not limited to possible or actual failure of the device.

The information that is communicated between the SM 10 and the data receiving device 82 may be useful for many purposes as described herein. In some cases, for example, sensor data information is collected and analyzed expressly for the health of an individual subject. In other cases, sensor data is collected and transmitted to another computing device to be aggregated with other data (for example, the SM data may be collected and aggregated with other data collected from an additional data receiving device (e.g., a device that may, in certain embodiments, include GPS data and the like).

FIG. 50 illustrates aspects of a computing server 802 as a cooperative bank of servers further including computing servers 802*a*, 802*b*, and one or more other servers 802*n*. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802*a*, 802*b*, 802*n*, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 50 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., sports equipment or area of play sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, glasses, wrist bands, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 812*b*, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 50, sensor data from, e.g., SM 10 is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various SMs is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensors e.g., 22, may include any information that an associated party desires to keep from wide or easy dissemination. Sensitive information can stand alone or be combined with other non-sensitive information.

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806*a*, 806*b*) is optionally encrypted before being communicated to a computing device.

In one embodiment, the operation of the information and communication technology (ICT) system 800 of FIG. 50 includes one or more sensor data computer programs stored on a computer-readable medium. The computer program may optionally direct and/or receive data from one or more sports equipment or area of play sensors sports equipment or area of played in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of sports equipment or area of play sensor data is stored on a non-transitory computer-readable medium in storage module 814. The computer program is configured to identify a subject who has a wireless sports equipment or area of play inserted in his or her body. The wireless sports equipment or area of play may include one or more wireless sensors.

In some cases, the computer program identifies one subject, and in other cases, two or more subjects are identified. The subjects may each have one or more sports equipment or areas of play, and each sports equipment or area of play may have one or more SMs of the type described herein.

The computer program is arranged to direct the collection of sensor data from the SM containing sports equipment or area of play. Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 50:

```
Start
Open a secure socket layer (SSL)
Identify a subject
Communicate with a predetermined control unit
Request sensor data from the subject via the control unit
Receive sensor data
If the sensor data is encrypted
    THEN decrypt the sensor data
Store encrypted data in the selected storage locations
Aggregate the sensor data with other sensor data
Store encrypted data in the selected storage locations
Maintain a record of the storage transaction
Perform post storage actions
End
```

Other representative examples of systems for collecting data from sports equipment include U.S. Pat. Nos. 8,477,046, 8,289,213 and US Patent App. No. US20160204958, all of which are incorporated by reference in their entirety.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, ambulance, truck, locomotive, tank, armored personnel carrier, etc.), (c) a building (e.g., a home, hospital, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., AT&T, T-Mobile, Verizon), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, sports equipment or areas of play utilizing a variety of SMs can be utilized to serve a variety of important functions, such as safe, accurate placement and deployment of the sports equipment or area of play, "real time" imaging of the sports equipment or area of play, the early identification of the development of sports equipment or area of play complications, and the subject's overall health status.

In one alternative, the subject may have a reading device in their home, gym or sports facility which collates the data from the sports equipment or area of play on a periodic basis, such as once per day or once per week. For example, within certain embodiments the devices and systems provided herein can instruct or otherwise notify the subject, or a permitted third-party as to deviations (e.g., greater than 10%, 20%, 25%, 50%, 70%, and or 100%) from normal, and/or, set parameters. In addition to empowering the subject to track and follow their own ability—and enabling them to see the positive (and negative) effects of variations in their life and exercise (e.g., training regimens).

Conventions

In general, and unless otherwise specified, all technical and scientific terms used herein shall have the same meaning as those commonly understood by one of ordinary skill in the art to which the embodiment pertains. For convenience, the meanings of selected terms are provided below, where these meanings are provided in order to aid in describing embodiments identified herein. Unless stated otherwise, or unless implicit from the context in which the term is used, the meanings provided below are the meanings intended for the referenced term.

Embodiment examples or feature examples specifically provided are intended to be exemplary only, that is, those examples are non-limiting on an embodiment. The term "e.g." (Latin, exempli gratia) is used herein to refer to a non-limiting example, and effectively means "for example". In addition, the Figures, while being understood to generally show the subject matter being described, should not be seen as limiting. For example, while SMs can be shown as a block, linear, or rectangular symbolically, they can in practice look quite differently, and be attached differently than shown. For example, where SMs are shown diagrammatically on stents as relatively linear objects, they can follow the struts or tynes of a stent and in practice be non-linear on the stent.

"Subjects" or "Subjects" refers to an organism for which the sports equipment or area of play can be utilized. Representative organisms include horses, cows, sheep, pigs, dogs, cats, rats and mice. Within one embodiment a particularly preferred organisms are humans.

Singular terms shall include pluralities and plural terms shall include the singular, unless otherwise specified or required by context. For example, the singular terms "a", "an" and "the" include plural referents unless the context clearly indicates otherwise. Similarly, the term "or" is intended to include "and" unless the context clearly indicates otherwise.

Except in specific examples provided herein, or where otherwise indicated, all numbers expressing quantities of a component should be understood as modified in all instances by the term "about", where "about" means±5% of the stated value, e.g., 100 refers to any value within the range of 95-105.

The terms comprise, comprising and comprises are used to identify essential features of an embodiment, where the embodiment may be, for example, a composition, device, method or kit. The embodiment may optionally contain one or more additional unspecified features, and so the term comprises may be understood to mean includes.

The following are some specific numbered embodiments of the devices, methods, systems and processes disclosed herein. These embodiments are exemplary only. It will be understood that the invention is not limited to the embodiments set forth herein for illustration, but embraces all such forms thereof as come within the scope of the above disclosure.

The following are exemplary embodiments of the present disclosure:

1) Sports equipment having a sensor.
2) The sports equipment according to embodiment 1, wherein said sports equipment is selected from the group consisting of wearable garments, protective gear, competitive objects of the game, and instruments or implements of the game.
3) The sports equipment according to embodiments 1 or 2 wherein said wearable garments are selected from the group consisting of, shoes or cleats, socks, uniforms, gloves, hats, wristbands and headbands.
4) The sports equipment according to embodiments 1 or 2 wherein said protective gear is selected from the group consisting of helmets, torso pads, wrist guards, thigh pads, knee pads and braces, and shin guards.
5) The sports equipment according to embodiments 1 or 2 wherein said competitive objects of the game are selected from balls and pucks.

6) The sports equipment according to any one of embodiments 1, 2, or 5 wherein said balls are selected from the group consisting of footballs, soccer balls, baseballs, tennis balls, golf balls and volley balls.
7) The sports equipment according to any one of embodiments 1 or 2 wherein said instruments or implements of the game are selected from the group consisting of bats, sticks, and clubs.
8) An area of play having a sensor.
9) The area of play according to embodiment 8 wherein said area of play is a field, court, course or rink.
10) The area of play according to embodiments 8 or 9 wherein said field is a football field, a soccer field or baseball field.
11) The area of play according to embodiment 9 wherein said court is a basketball, tennis, squash or volleyball court.
12) The area of play according to embodiments 8 or 9 wherein said area of play has a plate, a base, a hoop, a net, or a goalpost.
13) The sports equipment or area of play according to anyone of embodiments 1 to 12 wherein said sensor is a fluid pressure sensor, fluid volume sensor, contact sensor, position sensor such as GPS (global positioning system) sensor, pulse pressure sensor, blood volume sensors, blood flow sensor, chemistry (chemical) sensor (e.g., for blood and/or other fluids), metabolic sensor including tissue metabolic sensors (e.g., for blood and/or other fluids), accelerometer (including acceleration, tilt, vibration, shock and rotation sensors), mechanical stress sensor, mechanical pressure sensor, gyroscope, strain gauges, auditory sensor, optical system and/or sensor, time sensor or temperature sensor.
14) The sports equipment or area of play according to any one of embodiments 1 to 13 wherein both the sports equipment and the area of play have one or more sensors.
15) The sports equipment or area of play according to any one of embodiments 1 to 14 wherein said sensor comprises a sensor module.
16) The sports equipment or area of play according to any one of embodiments 1 to 15 wherein said sensor module comprises: a sensor channel; and a communication interface coupled to the sensor channel.
17) The sports equipment or area of play according to any one of embodiments 1 to 16 wherein the sensor module has a sensor channel includes a sensor and a sensor channel coupled to the sensor and to the communication interface.
18) The sports equipment or area of play according to any one of embodiments 1 to 17 wherein the sensor includes one or more of the following sensors: a global-positioning-system (GPS), accelerometer, Hall-effect, electrical, magnetic, thermal, pressure, radiation, optical, quantity-differential, capacitive, and time.
19) The sports equipment or area of play according to any one of embodiments 1 to 18 wherein the sensor is a microelectromechanical sensor. (MEMS).
20) The sports equipment or area of play according to any one of embodiments 1 to 19 wherein said sensor includes one or more of the following sensors: fluid pressure sensors, fluid volume sensors, contact sensors, position sensors, pulse pressure sensors, blood volume sensors, blood flow sensors, chemistry sensors, metabolic sensors, accelerometers, mechanical stress sensors and temperature sensors.
21) The sports equipment or area of play according to any one of embodiments 1 to 20 further comprising a communication interface such as a wireless interface.
22) The sports equipment or area of play according to any one of embodiments 1 to 21 wherein the sensor module has a communication interface configured to communicate with another sensor module.
23) The sports equipment or area of play according to any one of embodiments 1 to 22 wherein the sensor module further comprises a power supply coupled to the sensor channel and the communication interface.
24) The sports equipment or area of play according to any one of embodiments 1 to 23 wherein the sensor module further comprises a power supply coupled to the sensor and the communication interface and configured to harvest energy from a subject.
25) The sports equipment or area of play according to any one of embodiments 1 to 24 further comprising a power supply coupled to the sensor channel and to the communication interface and configured to receive energy wirelessly.
26) The sports equipment or area of play according to any one of embodiments 1 to 25 wherein the sensor module further comprises a controller coupled to the sensor channel and the communication interface.
27) The sports equipment or area of play according to any one of embodiments 1 to 26, further comprising: a housing; and wherein the sensor channel and the communication interface are disposed within the housing.
28) The sports equipment or area of play according to any one of embodiments 1 to 27 wherein said sensor is a plurality of sensors which are positioned on or within said sports equipment or area of play at a density of greater than 1, 2, 3, 4, 5, 6, 7, 8, 9, 10 or 20 sensors per square centimeter.
29) The sports equipment or area of play according to any one of embodiments 1 to 28 wherein said sensor is a plurality of sensors which are positioned on or within said sports equipment or area of play at a density of greater than 1, 2, 3, 4, 5, 6, 7, 8, 9, 10 or 20 sensors per cubic centimeter.
30) The sports equipment or area of play according to any one of embodiments 1 to 29 further comprising one or more passive sensors.
31) A method, comprising: sensing a physical quantity; and generating a representation of the sensed quantity.
32) The method of embodiment 31 wherein the physical quantity relates to an organism.
33) The method of embodiment 31 wherein sensing the physical quantity includes sensing the physical quantity from inside of an organism.
34) The method of embodiment 31, further comprising storing the representation of the sensed quantity.
35) The method of embodiment 31, further comprising transmitting wirelessly the representation of the sensed quantity to a device.
36) The method of embodiment 31, further comprising receiving wirelessly data from a device.
37) The method of embodiment 31, further comprising: wherein the sensing and generating are performed by a first sensor module; and transmitting wirelessly the representation of the sensed quantity to a second sensor module that is remote from the first sensor module.
38) The method of embodiment 31, further comprising: wherein the sensing and generating are performed by a first sensor module; and receiving with the first sensor module data from a second sensor module that is remote from the first sensor module.

39) The method of embodiment 31 wherein sensing is performed by at least a first sensor module which is attached to sports equipment or area of play according to any one of embodiments 1 to 12.

40) A system, comprising: a sensor module including a battery; and a battery charger configured to charge the battery wirelessly.

41) The system according to embodiment 40 wherein said sensor module is a sensor module attached to sports equipment or area of play according to any one of embodiments 1 to 12.

42) A system, comprising: a first sensor module; and a second sensor module configured to communicate with the first sensor module.

43) The system according to embodiment 42 wherein said first and/or second sensor module is a sensor module attached to sports equipment or area of play according to any one of embodiments 1 to 12.

44) The system of embodiment 42 wherein at least one of the first and second sensor modules is configured to be attached to an organism.

45) The system of embodiment 42 wherein at least one of the first and second sensor modules is configured to be inserted into sports equipment or an area of play.

46) The system of embodiment 42 wherein one of the first and second sensor modules is configured to power the other of the first and second sensor modules.

47) The sports equipment or area of play according to any one of embodiments 1-30 wherein said sensor is a plurality of sensors which are positioned on or within said sports equipment or area of play at a density of greater than 1, 2, 3, 4, 5, 6, 7, 8, 9, 10 or 20 sensors per square centimeter.

48) The sports equipment or area of play according to any one of embodiments 1-30 wherein said sensor is a plurality of sensors which are positioned on or within said sports equipment or area of play at a density of greater than 1, 2, 3, 4, 5, 6, 7, 8, 9, 10 or 20 sensors per cubic centimeter.

49) A method comprising:
  a. obtaining data from sensors positioned at a plurality of locations between on and/or within the sports equipment or area of play according to any one of embodiments 1-30;
  b. storing the data in a memory device located on or within the sports equipment or area of play; and
  c. transferring the data from the memory to a location outside the sports equipment or area of play.

50) The method according to embodiment 49 further comprising the step of analyzing said data.

51) A method for detecting and/or recording an event in a subject associated with the sports equipment or area of play according to any one of embodiments 1-30, comprising the step of interrogating at a desired point in time the activity of one or more sensors within the sports equipment or area of play, and recording said activity.

52) The method according to embodiment 51 wherein the step of interrogating is performed by a subject associated with said sports equipment or area of play.

53) The method according to embodiment 51 or 52 wherein said recording is performed on a wearable device.

54) The method according to any one of embodiments 51-53 wherein said recording, or a portion thereof, is provided to a health care provider.

55) A method for imaging the sports equipment or area of play, comprising the steps of
  (a) detecting the location of one or more sensors in the sports equipment or area of play according to any one of embodiments 1-30; and
  (b) visually displaying the location of said one or more sensors, such that an image of the sports equipment or area of play, or a portion thereof, is created.

56) The method according to embodiment 55 wherein the step of detecting occurs over time.

57) The method according to embodiment 55 or 56 wherein said visual display shows changes in the positions of said sensors over time, and/or changes in temperature of the sensors or surrounding tissue over time.

58) The method according to any one of embodiments 55-57 wherein said visual display is a three-dimensional image of said sports equipment or area of play.

59) A method for inspecting the sports equipment or area of play according to any one of embodiments 1-30, comprising the steps of (a) associating a sensor with the sports equipment or area of play according to any one of embodiments 1-30 into a subject; and (b) imaging the placement of said sensor according to the method of an one of embodiments 47 to 50.

60) A method for examining the sports equipment or area of play according to any one of embodiments 1-30 which has been previously associated with a subject, comprising the step of imaging the sports equipment or area of play according to the method of any one of embodiments 47 to 50.

61) A method of monitoring a sports equipment or area of play, comprising:
  a. transmitting a wireless electrical signal from a location on or within sports equipment or an area of play according to any one of embodiments 1-30;
  b. receiving the signal;
  c. powering the sensor using the received signal;
  d. sensing data at the sensor; and
  e. outputting the sensed data from the sensor to a receiving unit.

62) The method according to embodiment 61 wherein said receiving unit is a watch, wrist band, cell phone or glasses.

63) The method according to embodiments 61 or 62 wherein said receiving unit is located within a subject's residence or office.

64) The method according to embodiments any one of embodiments 61-63 wherein said sensed data is provided to a health care provider.

65) The method according to any one of embodiments 61-64 wherein said sensed data is posted to one or more websites.

66) A non-transitory computer-readable storage medium whose stored contents configure a computing system to perform a method, the method comprising:
  a. identifying a subject, the identified subject having at least one wireless sports equipment or area of play according to any one of embodiments 1-30, each wireless sports equipment or area of play having one or more wireless sensors;
  b. directing a wireless interrogation unit to collect sensor data from at least one of the respective one or more wireless sensors; and
  c. receiving the collected sensor data.

67) The non-transitory computer-readable storage medium of embodiment 66 whose stored contents configure a computing system to perform a method, the method further comprising:
   a. identifying a plurality of subjects, each identified subject associated with at least one sports equipment or area of play, each sports equipment or area of play having one or more wireless sensors;
   b. directing a wireless interrogation unit associated with each identified subject to collect sensor data from at least one of the respective one or more wireless sensors;
   c. receiving the collected sensor data; and
   d. aggregating the collected sensor data.
68) The non-transitory computer-readable storage medium of embodiment 66 whose stored contents configure a computing system to perform a method, the method further comprising:
   a. removing sensitive subject data from the collected sensor data; and
   b. parsing the aggregated data according to a type of sensor.
69) The non-transitory computer-readable storage medium of embodiment 66 whose stored contents configure a computing system to perform a method, wherein directing the wireless interrogation unit includes directing a control unit associated with the wireless interrogation unit.
70) The non-transitory computer readable storage medium according to any one of embodiments 66 to 69, wherein said sports equipment or area of play is according to any one of embodiments 1-30.
71) The storage medium according to any one of embodiments 66-70 wherein said collected sensor data is received on a watch, wrist band, cell phone or glasses.
72) The storage medium according to any one of embodiments 66-71 wherein said collected sensor data is received within a subject's residence or office.
73) The storage medium according to any one of embodiments 66-72 wherein said collected sensed data is provided to a health care provider.
74) The storage medium according to any one of embodiments 66-73 wherein said sensed data is posted to one or more websites.
75) The method according to any one of embodiments 49-65, or storage medium according to any one of embodiments 66-74, wherein said data is analyzed.
76) The method or storage medium according to embodiment 75 wherein said data is plotted to enable visualization of change over time.
77) The method or storage medium according to embodiments 75 or 76 wherein said data is plotted to provide a three-dimensional image.
78) A method for determining degradation of a sports equipment or area of play, comprising the steps of a) providing to a subject a sports equipment or area of play according to any one of embodiments 1-30, and b) detecting a change in a sensor, and thus determining degradation of the sports equipment or area of play.
79) The method according to embodiment 78 wherein said sensor is capable of detecting one or more physiological and/or locational parameters.
80) The method according to embodiments 78 or 79 wherein said sensor detects a location within the subject.
81) The method according to any one of embodiments 78-80 wherein said sensor moves from its original location, thereby indicating degradation of the sports equipment or area of play.
82) The method according to any one of embodiments 78-81 wherein the step of detecting is a series of detections over time.
83) A method for determining an infection associated with a sports equipment or area of play, comprising the steps of a) providing to a subject a sports equipment or area of play according to any one of embodiments 1-30, wherein said sports equipment or area of play comprises at least one temperature sensor and/or metabolic sensor, and b) detecting a change in said temperature sensor and/or metabolic sensor, and thus determining the presence of an infection.
84) The method according to embodiment 83 wherein the step of detecting is a series of detections over time.
85) The method according to embodiments 83 or 84 wherein said change is greater than a 1% change over the period of one hour.
86) The method according to any one of embodiments 83-85 wherein said change is a continually increasing temperature and/or metabolic activity over the course of 4 hours.

All of the U.S. patents, U.S. patent application publications, U.S. patent applications, foreign patents, foreign patent applications and non-patent publications referred to in this specification are incorporated herein by reference, in their entirety. These documents are incorporated herein by reference for all purposes. For example, those documents may describe transmitting a wireless electrical signal from a location on or within a specified place; receiving the signal; using an antenna for data and/or power transmission; powering the sensor using the received signal; using a battery to provide power and power management; sensing data at the sensor; and outputting the sensed data from the sensor to a receiving unit; assessing the data; processing the data; providing a visual output based on the data, software to achieve desired results, etc., any or all of which may be adapted for use in the present invention. In addition to the documents already identified in the preceding paragraphs, the following documents are incorporated herein by reference in their entireties for all purposes: U.S. patent application Nos. 62/312,072; 62/312,079; 62/312,095; 62/312,108; 62/312,114; 62/312,120; 62/312,131; 62/312,180; 62/312,188; 62/312,193; 62/312,197; and 62/312,205.

The various embodiments described above can be combined to provide further embodiments. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An item of sports equipment worn by a player and having a structure arranged to be located between a body part of a player and a playing environment, the structure configured to be subjected to impact forces during a playing of a sport, the item of sports equipment comprising:
   a plurality of first sensor modules, each first sensor module attached to the item of sports equipment and including a communication interface, a controller, a battery, and a battery charger configured to charge the battery wirelessly, the plurality of first sensor modules including:
  a first set of first sensor modules distributed on an inside surface of the structure configured to face the body part, each respective first sensor module in the first set of first sensor modules comprising a temperature sensor channel that includes a temperature sensor configured to sense temperature and to generate data corresponding to the sensed temperature, and a sensor interface configured to provide the data to the controller of the respective first sensor module, wherein the controller is configured to store the data in a memory of the controller and the communication interface of the respective first sensor module is configured to transmit the data, and
  a second set of first sensor modules distributed on an outside surface of the structure configured to face the playing environment, each respective first sensor module in the second set of first sensor modules comprising a pressure sensor channel that includes a first pressure sensor configured to sense impact force and to generate data corresponding to the impact force, and a sensor interface configured to provide the data to the controller of the respective first sensor module, wherein the controller is configured to store the data in a memory of the controller and the communication interface of the respective first sensor module is configured to transmit the data; and
a second sensor module attached to the item of sports equipment and including a communication interface, a controller, and at least one sensor channel, the second sensor module configured to communicate with at least one of the plurality of first sensor modules via the communication interface, the at least one sensor channel including a passive sensor configured to receive power wirelessly from the first sensor module and to sense a quantity and to generate data corresponding to the sensed quantity, and a sensor interface configured to provide the data to the controller of the second sensor module, wherein the passive sensor comprises one of an accelerometer, a second pressure sensor, a contact sensor, a position sensor, a chemical sensor, a tissue metabolic sensor, a mechanical stress sensor, an auditory sensor, and a temperature sensor.

2. The item of sports equipment of claim 1, wherein the item of sports equipment corresponds to one of wearable garments and protective gear.

3. The item of sports equipment of claim 1, wherein each of the plurality of first sensor modules is remote from the second sensor module.

4. The item of sports equipment of claim 1, wherein the second sensing module is configured to transmit the data generated by the at least one sensor channel to at least one of the plurality of first sensing modules.

5. The item of sports equipment of claim 1, wherein the size of each of the plurality of first sensor modules distributed on one or more of the inside surface and the outside surface is less than one cubic centimeter.

6. The item of sports equipment of claim 1, wherein at least one of the first sensing modules in the first set of first sensing modules further comprises a chemical sensor channel that includes a chemical sensor configured to sense a chemical and to generate data corresponding to the sensed chemical, and a sensor interface configured to provide the data to the controller of the at least one first sensor module.

7. The item of sports equipment of claim 1, wherein at least one of the first sensing modules in the first set of first sensing modules further comprises a tissue metabolic sensor channel that includes a tissue metabolic sensor configured to sense a quantity of metabolism and to generate data corresponding to the sensed quantity, and a sensor interface configured to provide the data to the controller of the at least one first sensor module.

8. The item of sports equipment of claim 1, wherein at least one of the first sensing modules in the second set of first sensing modules further comprises a motion sensor channel that includes an accelerometer configured to sense motion and to generate data corresponding to the sensed motion, and a sensor interface configured to provide the data to the controller of the at least one first sensor module.

9. The item of sports equipment of claim 1, wherein at least one of the first sensing modules in the second set of first sensing modules further comprises a mechanical stress sensor channel that includes a mechanical stress sensor configured to sense mechanical stress and to generate data corresponding to the sensed mechanical stress, and a sensor interface configured to provide the data to the controller of the at least one first sensor module.

10. The item of sports equipment of claim 1, wherein at least one of the first sensing modules in the second set of first sensing modules further comprise a position sensor channel that includes a position sensor configured to sense position and to generate data corresponding to the sensed position, and a sensor interface configured to provide the data to the controller of the at least one first sensor module.

11. The item of sports equipment of claim 1, wherein at least one of the first sensing modules in the second set of first sensing modules further comprise an environmental sensor channel that includes an environmental sensor configured to sense an environmental condition and to generate data corresponding to the sensed condition, and a sensor interface configured to provide the data to the controller of the at least one first sensor module.

* * * * *